US006940065B2

(12) United States Patent
Graber et al.

(10) Patent No.: US 6,940,065 B2
(45) Date of Patent: Sep. 6, 2005

(54) METHOD FOR CHARACTERIZING BIOMOLECULES UTILIZING A RESULT DRIVEN STRATEGY

(75) Inventors: Armin Graber, Marlboro, MA (US); Dale H. Patterson, Hudson, MA (US); Peter Juhasz, Natick, MA (US); Stephen A. Martin, Belmont, MA (US)

(73) Assignee: Applera Corporation, Norwalk, CT (US)

( * ) Notice: Subject to any disclaimer, the term of this patent is extended or adjusted under 35 U.S.C. 154(b) by 43 days.

(21) Appl. No.: 10/646,371

(22) Filed: Aug. 22, 2003

(65) Prior Publication Data

US 2004/0108452 A1 Jun. 10, 2004

Related U.S. Application Data

(60) Provisional application No. 60/405,578, filed on Aug. 22, 2002.

(51) Int. Cl.[7] .......................... H01J 49/00; B01D 59/44
(52) U.S. Cl. ....................... 250/282; 290/281; 290/287; 290/288; 382/128; 382/129
(58) Field of Search ................................ 250/281, 282, 250/287, 288; 382/128, 129

(56) References Cited

U.S. PATENT DOCUMENTS

| 5,625,184 | A | * | 4/1997 | Vestal et al. ................. 250/287 |
| 6,064,754 | A | * | 5/2000 | Parekh et al. ................ 382/129 |
| 6,278,794 | B1 | * | 8/2001 | Parekh et al. ................ 382/129 |
| 6,329,146 | B1 | * | 12/2001 | Crooke et al. .................. 435/6 |
| 2002/0001814 | A1 | | 1/2002 | Chu et al. |

FOREIGN PATENT DOCUMENTS

| EP | 1 006 559 A2 | 7/2000 |
| WO | WO 02/21139 A2 | 3/2002 |
| WO | WO 02/061047 A3 | 8/2002 |
| WO | WO 02/061047 A2 | 8/2002 |

OTHER PUBLICATIONS

Aebersold R, Goodlett DR, Mass spectrometry in proteomics, *Chem. Rev.* Feb. 2001; 101:269–295.
Berger S.J., Lee S.W., Anderson G.A., Pasa–Tolic L., et al., *Anal. Chem.* 2002, 74: 4994–5000.
Bergholz A., Heymann S., Schenk J. A, Freytag J. C., *Acta Biotheor.* 2001, 49: 145–159.
Bhattacharya A., Czaplinski K., Trifillis P., He F., et al.,*RNA* *2000*, 6: 1226–1235.
Bienvenut W.V., Deon C., Pasquarello C., Campbell J.M., et al., *Proteomics* 2002, 2: 868–876.
Chakravarti D. N., Chakravarti B., Moutsatsos I., *Biotechniques.* 2002, *Computational Proteomics Supplement* 32: S4–S15.
Coghlan A., Wolfe K.H., *Yeast* 2000, 16: 1131–1145.
Creasy D.M., and Cottrell J.S., *Proteomics* 2002, 2: 1426–1434.
Dongre A.R., Eng J.K., Yates J.R. 3rd., *Trends Biotechnol.* 1997, 15: 418–445.
Ducret A, Van Oostveen I, Eng JK, Yates JR 3rd, Aebersold R. Links: *Protein Sci.* 1998; 7: 706–719.
Dwight S.S., Harris M.A., Dolinski K., Ball C.A., et al., *Nucleic Acids Research* 2002, 30: 69–72.
Foret F, Muller O, Thorne J, Gotzinger W, et al., *J. Chromatogr A* 1995, 716: 157–166.
Forster J., Gombert A.K., Nielsen J., *Biotechnol. Bioeng.* 2002, 79: 703–712.

(Continued)

*Primary Examiner*—Nikita Wells
(74) *Attorney, Agent, or Firm*—Lahive & Cockfield, LLP

(57) ABSTRACT

In various embodiments, the methods for analyzing a sample are provided utilizing a result dependent acquisition strategy. In various embodiments, methods for analyzing a sample are provided wherein the sample is first analyzed by MALDI and MS to produce a first result that is then used to determine a second analysis that is used to analyze the sample again by MALDI and MS/MS or MS[n] to produce a second result.

30 Claims, 36 Drawing Sheets

OTHER PUBLICATIONS

Futcher B, Latter GI, Monardo P, McLaughlin CS, et. al., *Mol. Cell Biol.* 1999, 19: 7357–7368.

Griffin T.J., Gygi S.P., Ideker T., Rist B., et al., *Mol. Cell. Proteomics* 2002, 1: 323–333.

Griffin T.J., Han D.K., Gygi S.P., Rist B., et al., *J. Am. Soc. Mass Spectrom.* 2001, 12: 1238–1246.

Griffin TJ, Goodlett DR, Aebersold R, *Curr. Opin. Biotechnol.* 2001, 12: 607–612.

Gygi S.P., Rist B., Gerber S.A., Turecek F., et al., *Nat. Biotechnol.* 1999, 17: 994–999.

Gygi SP, Rist B, Griffin TJ, Eng J, et al., *J. Proteome Res.* 2002, 1: 47–54.

Han D.K., Eng J., Zhou H., and Aebersold R., *Nat Biotechnol.* 2002, 19: 946–951.

Hansen KC, Schmitt–Ulms G, Chalkley RJ, Hirsch J, Baldwin MA, et. al., *Mol. Cell. Proteomics* 2003, 2.5: 299–314.

He F., Brown A.H., and Jacobson A., *Mol. Cell. Biol.* 1997, 17: 1580–1594.

Ideker T., Thorsson V., Ranish J.A., Christmas R., et al., *Science.* 2001, 292: 929–934.

Johnson RS, Taylor JA. *Mol. Biotechnol.* 2002, 22: 301–315.

Keller A, Nesvizhskii Al, Kolker E, Aebersold R, *Anal. Chem.* 2002; 74:5383–5392.

Kinney D.M., Lusty C.J., *Mol. Cell. Biol.* 1989, 9: 4882–4888.

Liu H., Lin D., Yates J.R. 3rd., *Biotechniques* 2002, 32: 898–902.

Mann M., and Wilm M., *Anal. Chem.* 1994, 66: 4390–4399.

Maquat L.E. *Curr. Biol.* 2002, 12: R196–R197.

Messenguy F., Vierendeels F., Pierard A., Delbecq P., *Curr. Gnet.* 2002, 41: 224–231.

Mortz E., Vorm O., Mann M., Roepstorff P., *Biol. Mass Spectrom.* 1994, 23: 249–261.

Parker K.C., *J Am Soc Mass Spectrom.* 2002; 13:22–39.

Paton N.W., Khan S.A., Hayes A., Moussouni F., et al., *Bioinformatics* 16: 548–557.

Perkins D.N., Pappin D.J., Creasy D.M., and Cottrell J.S., *Electrophoresis* 1999, 20: 3551–3567.

Sharp P.M, Li W.H., *Nucleic Acids Res.* 1987; 15: 1281–1295.

Shevchenko A, Chernushevich I, Ens W, Standing KG, et al., *Rapid Commun. Mass Spectrom.* 1997;11: 1015–1024.

Shevchenko A., Sunyaev S., Loboda A., Shevchenko A., et al., *Anal. Chem.* 2001, 73: 1917–1926.

Takao T, Gonzalez J, Yoshidome K, Sato K, et. al., *Anal. Chem.* 1993, 65: 2394–2399.

Wait R., Miller I., Eberini I., Cairoli F., et al., *Electrophoresis* 2002, 23: 3418–3427.

Wattenberg A, Organ AJ, Schneider K, Tyldesley R, et al., *J. Am. Soc. Mass Spectrom.* 2002, 13: 772–783.

Wolters D.A., Washburn M.P., and Yates J.R. 3rd, *Anal Chem.* 2001, 73: 5683–5690.

Wool A., Smilansky Z., *Proteomics 2000*, 2: 1365–1373.

Yergey A.L., Coorssen J.R., Backlund P.S. Jr, Blank P.S., et al., *J. Am. Soc. Mass Spectrom.* 2002, 13: 784–791.

Zhang N, Aebersold R, Schwikowski B., *Proteomics* 2002 2: 1406–1412.

Zhang R., Regnier F.E., *J. Proteome Res*, 2002, 1: 139–147.

Zhu X, Graber A., Hatten S., Juhasz P.S., et al., *50th ASMS Conference*, 2002, Jun. 2–6, Orlando, FL.

Gras R., et al. Improving protein identification from peptide mass fingerprinting through a parameterized multi–level scoring algorithm and an optimized peak detection. Electrophoresis. 1999; vol. 20:3535–3550.

Papayannopoulos, I.A., The Interpretation of Collision–induced Dissociation Tandem Mass Spectra of Peptides, Mass Spectrometry Reviews, 1995; vol. 14:49–73.

Partial International Search Report for PCT/US03/26471 as an annex to an Invitation to Pay Additional Fees.

Jensen, O.N., et al. "Delayed extraction improves specificity in database searches by matrix–assisted laser desorption/ionization peptide maps" *Rapid Communications in Mass Spectrometry* 1996 (10);1371–1378.

International Search Report for PCT/US03/26471.

* cited by examiner

```
SELECT   Protein_Experiment.Accession_Nr, ORF, Protein_Experiment.Expression,
         m_RNA_Experiment.Expression, Codon_Bias
FROM     Protein_Experiment, Protein_Gene_Reference, mRNA_Experiment, Codon_Bias, Gene_Ontology
WHERE    Protein_Experiment.Accession_Nr       =   Protein_Gene_Reference.Accession_Nr
AND      Protein_Gene_Reference.ORF            =   mRNA_Experiment.ORF
AND      Protein_Gene_Reference.ORF            =   Codon_Bias.ORF
AND      Protein_Gene_Reference.ORF            =   Gene_Ontology.ORF
AND      Gene_Ontology.Biological_Function     =   'arginine biosynthesis'
```

FIG. 7

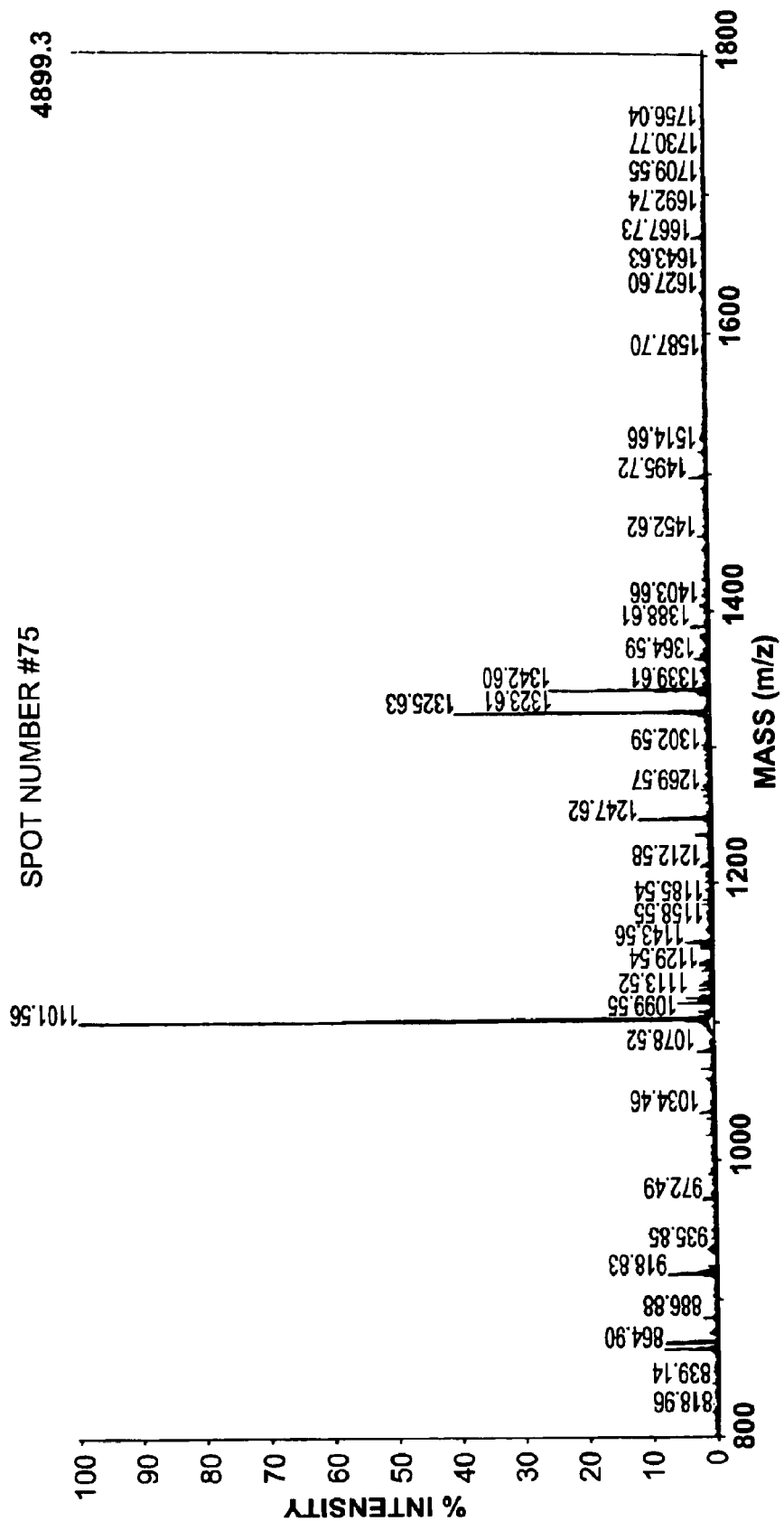

METHOD FOR CHARACTERIZING BIOMOLECULES UTILIZING A RESULT DRIVEN STRATEGY

CROSS REFERENCES TO RELATED APPLICATIONS

The present application claims the benefit of U.S. Provisional Application No. 60/405,578, filed Aug. 22, 2002. The entire contents of the above application is incorporated herein by reference in its entirety.

BACKGROUND

Mass spectrometry (MS) is an analytical technique for determining the presence of molecules in a sample. A sample in the mass spectrometer is vaporized and ionized in an ion source and the mass-to-charge ratio of the resulting ions is determined. A time-of-flight mass spectrometer (TOF MS) determines the mass-to-charge ratio of an ion by measuring the amount of time it takes a given ion in the sample to travel from the ion source to a detector with the assistance of electric fields. The time required for an ion to reach the detector is a direct function of its mass and an inverse function of its charge. A sample may contain a single constituent molecule or an almost infinite number of molecules. The presence of a molecule in the sample may be determined by correlating the information contained in the sample mass spectrum with known or theoretical mass spectra for the molecule or by determining the molecule's structure de novo.

Mass spectroscopy is of particular importance in the area of proteome analysis, which includes the measurement of protein expression in a biological sample to characterize biological processes, such as disease or mechanisms of gene expression. Understanding protein expression is crucial to a complete understanding of biological systems. Used in conjunction with gene expression and metabolic studies, protein expression studies are a key tool in understanding biological systems and developing new diagnostics and treatments.

Unlike mRNA, which only acts as a disposable messenger, proteins implement almost all controlled biological functions and, as a result, are integral to such functions as normal cell activity, disease processes, and drug responses. However, protein expression is not reliably predictable. First, protein expression is not predictable from mRNA expression maps because mRNA transcript levels are not strongly correlated with protein levels. Second, proteins are dynamically modified in biological systems by environmental factors in ways which are not predictable from genetic information. Accordingly, knowledge of a biological system's response to a stimulus such as a drug or a condition such as a disease typically requires a comparison of many "normal" with corresponding "abnormal" samples. Thus, proteome analysis requires the determination of the proteins present in a variety of samples.

Presently, the majority of MS processes utilize an electrospray ionization (ESI) ion source as a means for introducing an ionized sample that originates from a high performance liquid chromatograph (HPLC) into a MS apparatus. One of several desirable features of ESI is that fractions from the chromatography column can proceed directly from the HPLC to the ESI ion source. This desirable feature of ESI, however, means that re-sampling a given portion of the sample (e.g. a certain fraction from the column) is generally not possible because it is difficult to stop the flow of effluent from the HPLC and monitor chromatographic resolution. The operator is thus typically constrained to subjecting to MS analysis only that portion of a composition that is currently exiting the ESI nozzle as an ionized spray. Thus, the operator can not stop information acquisition of a sample and ask for additional information acquisition on the previously eluded portion of the sample based upon knowledge of sample characterization obtained during or after an analysis cycle. In such a case, the operator would have to re-inject the HPLC with the composition assuming some remains. However, each injection of a composition into an HPLC can be considered as different samples because of HPLC reproducibility issues such as, for example, difficulties in maintaining the same retention speed.

SUMMARY

In many samples of interest to the life sciences, the mass spectrum generated by a single dimension of mass spectrometry has so many peaks that deriving useful information from the spectrum is difficult. Accordingly, approaches that use multiple dimensions of mass spectrometry, such as, for example, tandem mass spectrometry (MS/MS) or, more generally, multidimensional mass spectrometry ($MS^n$), are often used. Analysis in the MS/MS mode is typically achieved by selecting a molecular ion (often referred to as "the parent ion" or "the precursor ion") with a first mass spectrometer (often referred to as the first dimension of mass spectrometry) and directing the parent ion into an ion fragmentor (e.g., collision cell where it collides with an inert gas). The parent ion is fragmented in the fragmentor to a series of fragment ions (often referred to as "daughter ions"). The daughter ions are then typically directed into a second mass spectrometer (often referred to as the second dimension of mass spectrometry) to resolve the fragmentation pattern of the parent ion, which is often referred to as the fragmentation spectrum.

In various aspects, provided are methods for analyzing a sample containing biomolecules. In various embodiments, the methods facilitate the identification of biomolecules in a sample containing biomolecules. In various embodiments, the methods facilitate identifying and/or characterizing the biomolecules in a biological sample utilizing a result driven acquisition strategy. In various embodiments, an acquisition strategy for selecting masses of a sample for further analysis by MS/MS or $MS^n$ is driven by the results of an expression based analysis, a mass spectrometric data analysis, a search result based analysis, or combinations thereof, of one or more initial mass spectra of one or more portions of the sample. For example, the one or more initial mass spectra can be mass spectra obtained of one or more sample spots on one or more MALDI sample plates.

A result driven acquisition strategy can be implemented in a variety and combination of workflows, for example, in various embodiments: a workflow based on analysis of expression dependent results can be used; a workflow based on mass spectrometric data dependent results driven strategies can be used; in various embodiments, search result-dependent results can be used; and two or more of expression dependent, mass spectrometric data dependent, and search result-dependent results can be used.

In various embodiments, the methods utilize result dependent workflows that store and consolidate results from several acquisitions in a relational database or an object oriented database, including one or more of the process parameters used for MS operation and for MS/MS identification. The methods can utilize off-line coupling of $\mu LC$ with MS quantitation, MS/MS identification, and a relational database to store and consolidate results from several acquisitions, including the process parameters used for identification and quantitation.

In another aspect, provided are articles of manufacture where the functionality of a method of the invention is embedded on a computer-readable medium, such as, but not limited to, a floppy disk, a hard disk, an optical disk, a magnetic tape, a PROM, an EPROM, CD-ROM, DVD-ROM, or resident in computer or processor memory. The functionality of the method can be embedded on the computer-readable medium in any number of computer readable instructions, or languages such as, for example; FORTRAN, PASCAL, C, C++, BASIC and, assembly language. Further, the computer-readable instructions can, for example, be written in a, script, macro, or functionally embedded in commercially available software, (e.g. EXCEL or VISUAL BASIC).

The foregoing and other aspects, embodiments, and features of the invention can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the invention.

BRIEF DESCRIPTION OF VARIOUS EMBODIMENTS

FIG. 7 illustrates various embodiments of relationships used in various embodiments of the relational database of FIG. 6.

FIGS. 10A–10F are examples of mass spectra obtained in Example 1.

DETAILED DESCRIPTION OF THE INVENTION

Figure 1:
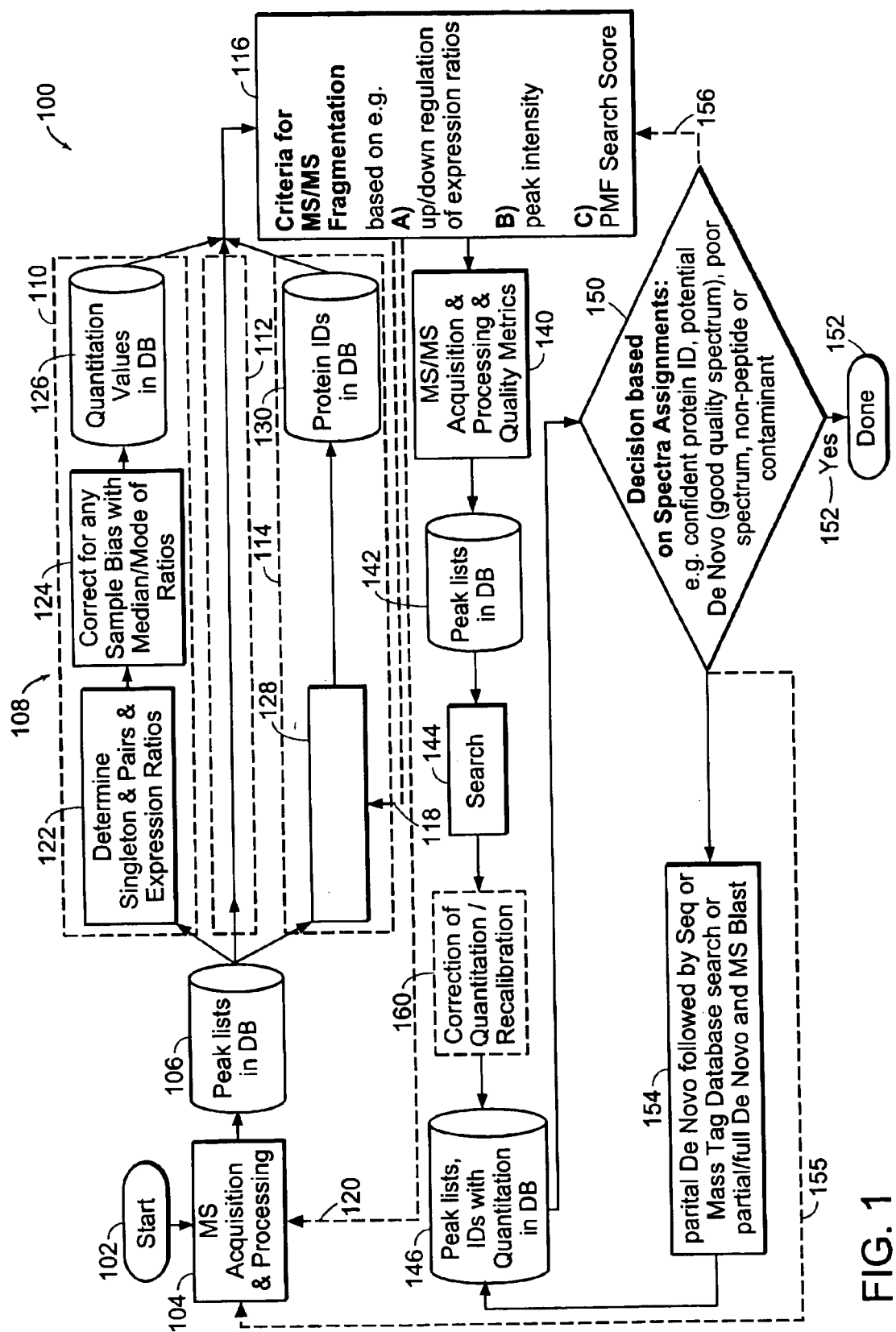
FIG. 1 is a flow diagram illustrating various embodiments of methods for analyzing a sample containing biomolecules.

In various aspects, the present teachings facilitate the identification and/or analysis of biomolecules in biological samples. The biological sample can be subjected to preliminary processing, including preliminary separation techniques. For example, cells or tissues can be extracted and subjected to subcellular fractionation for separate analysis of biomolecules in distinct subcellular fractions, e.g., proteins or drugs found in different parts of the cell. Immunoprecipitation can be performed to identify antigenically related biomolecules such as proteins.

As used herein, the term "biomolecule" refers to any organic molecule that is present in a biological sample, and includes, but is not limited to, peptides, polypeptides, proteins, oligosaccharides, lipids, steroids, prostaglandins, prostacyclines, and nucleic acids (including DNA and RNA). Accordingly, in various embodiments, the methods facilitate identifying and/or characterizing the proteins in a biological sample utilizing a result driven acquisition strategy. As used herein, the term "protein" includes, but is not limited to, both unmodified and modified proteins (e.g., glycosylated and unglycosylated proteins).

As used herein, the term "biological sample" refers to any solid or fluid sample obtained from, excreted by or secreted by any living organism, including, but not limited to, single-celled microorganisms (such as bacteria and yeasts) and multicellular organisms (such as plants and animals, including samples from a healthy or apparently healthy human subject or a human patient affected by a condition or disease to be diagnosed or investigated). For example, a biological sample can be a biological fluid obtained from, e.g., blood, plasma, serum, urine, bile, cerebrospinal fluid, aqueous or vitreous humor, or any bodily secretion, a transudate, an exudate (e.g., fluid obtained from an abscess or any other site of infection or inflammation), or fluid obtained from a joint (e.g., a normal joint or a joint affected by disease such as a rheumatoid arthritis, osteoarthritis, gout or septic arthritis). A biological sample can also be a sample obtained from any organ or tissue (including a biopsy or autopsy specimen) or can comprise cells (whether primary cells or cultured cells) or medium conditioned by any cell, tissue or organ.

Suitable sample preparation procedures, include, but are not limited to, procedures that produce a sample array capable of being processed by a MALDI method. For example, one or more of liquid chromatography, 1D electrophoresis, 2D electrophoresis, protein separation, tissue laser micro-dissection, and proteolysis can be utilized to separate a biological sample into its constituent components to produce a sample for deposition as a continuous sample or as discrete sample portions on a MALDI plate, such that MALDI MS analysis can be effected. For example, MALDI MS analysis can be conducted on substantially whole proteins, peptides (e.g., produced by proteolysis of proteins in the biological sample), or combinations thereof.

For example, one suitable approach to forming samples for use in a continuous or on-line MALDI MS system is disclosed in U.S. Pat. No. 6,175,112, issued Jan. 16, 2001, the entire disclosure of which is hereby incorporated by reference. A liquid sample is deposited from an infusion device, such as a capillary liquid chromatographic device continuously onto a substrate to form a solid trace having a narrow width to provide a sample, where, for example, a portion of which can then be desorbed, such as with a pulsed laser beam, to form an ionized vapor sample that can be analyzed by MS.

In various embodiments, the methods provide a sample containing biomolecules as a plurality of sample portions suitable for ionization by MALDI. The plurality of sample portions can be discrete portions (e.g., a series of spots), substantially contiguous portions (e.g., a continuous band of sample), or a combination of both. The sample portions are provided on a substrate suitable for use with a MALDI mass spectrometer. The methods acquire one or more mass spectra of one or more sample portions to generate a first data set comprising a list of mass signals (also referred to as mass peaks). Each mass signal has an associated intensity (related to the abundance of the ion) and an associated mass (related to the mass-to-charge (m/z) ratio of the ion). The first data set is analyzed using one or more of an expression based analysis, a mass spectrometric data analysis, and a search result based analysis, to generate a first set of precursor selection criteria. One or more m/z ranges are then selected for further analysis by MS/MS or $MS^n$ based on the first set of precursor selection criteria. The methods acquire one or more fragmentation spectra for the one or more m/z ranges selected for further analysis based on the first set of precursor selection criteria. In various embodiments, one or more of the fragmentation spectra are analyzed to identify one or more biomolecules in the sample. In various embodiments, the methods include compensating for sample bias in expression dependent data.

As used herein, an "expression based analysis" refers to an analysis that is based, for example, on the differential expression of biomolecules in a sample under investigation, between a sample under investigation and a control sample, or both.

In various embodiments using an expression based analysis, selection of mass signals for further MS/MS or $MS^n$ analyses mass signals is based on expression ratios. In various embodiments of analysis of peptides and proteins using an expression based analysis, the methods use a quantitation methodology involving isotope coded affinity tags (ICAT) to provide quantitation information (i.e., the relative abundances of differentially labeled pairs). In various embodiments, mass signals are selected for additional MS processing by MS/MS or $MS^n$ based the relative difference in expression between the isotopic mass signals. For example, in various embodiments, isotopic mass signals having greater than three-fold difference in relative expression ratio are selected to undergo additional MS processing by MS/MS or $MS^n$. In various embodiments, mass signals are selected based on whether they are up-regulated or down-regulated.

In various embodiments utilizing an experimental sample and a control sample, the median expression ratio, representing the majority of the proteins in a biological sample that do not change between the experimental sample (sample under investigation) and the control sample can be calculated. In various embodiments, the median or mean expression ratio can be used to correct for systematic bias affecting the expression levels in a study that is due, for example, to unequal amounts of starting material or sample handling errors. For example, in various embodiments using an expression based analysis the most intense peaks from each heavy light (HL) pair with expression ratios greater than 2 standard deviations from the median expression ratio are selected to undergo additional MS/MS or $MS^n$ processing.

As used herein, a "mass spectrometric data based analysis" refers to an analysis that is based, for example, on the signal intensity of a mass signal. Herein, the term "signal intensity" is meant to refer to the intensity associated with a mass signal regardless of whether the intensity is an absolute signal intensity, a corrected signal intensity, a relative signal intensity, or a signal-to-noise (S/N) parameter. In various embodiments, a mass spectrometric data based analysis selects mass-to-charge ratio ranges for further MS/MS or $MS^n$ analysis based on one or more of: (1) the absolute mass signal intensity; (2) the relative mass signal intensity; (3) the mass signal intensity relative to a S/N threshold; and (4) the mass signal peak area.

In various embodiments, mass spectrometric data based analysis involves selecting mass peaks for further MS/MS or $MS^n$ analysis which are detected with lower intensities. For example, the identification of the minor components in each sample portion first, which are detected with lower intensities, facilitates their identification before much of the sample is consumed. Since it will become more difficult to detect the biomolecules with lower intensities upon further sample consumption, it can be desirable to prioritize the subsequent MS/MS or $MS^n$ analysis of mass signals detected with lower intensities. In various embodiments, the n most intense peaks per mass spectrum are selected for MS/MS or $MS^n$ analysis. Examples of values for n include, but are not limited to; values of n in the range from about 1 to about 6. Values for n can be chosen, for example, based on computational resources. For example where a mass spectrum is taken for each sample spot on a 96 well MALDI sample plate using n=4 could result in 384 peaks being selected; and, where a mass spectrum is taken for each sample spot on ten 96-well MALDI plates over 3000 peaks could be selected. In various embodiments, peaks already selected from one mass spectrum are removed from consideration as one of the n most intense peaks in other mass spectra. In various embodiments, a list of selected m/z ratio ranges for MS/MS or $MS^n$ analysis is revised to exclude duplicate m/z ratio ranges.

For example, a first mass signal having a corresponding first mass-to-charge ratio range meets the n most intense criteria in two or more mass spectra. In various embodiments, the first mass signal is considered as one of the n most intense peaks "only" in the mass spectrum where; (1) it is the weakest of the n most intense peaks in the mass spectrum; (2) it is the strongest of the n most intense peaks in the mass spectrum; (3) where it has the highest absolute signal intensity and is one of the n most intense peaks in the mass spectrum; or (4) where it has the lowest absolute signal intensity and is one of the n most intense peaks in the mass spectrum.

In various embodiments, the n most intense peaks per mass spectrum are initially selected and MS/MS or $MS^n$ analysis is begun on the corresponding mass-to-charge ration ranges from the weakest initially selected peak to the strongest, or, from the strongest initially selected peak to the weakest. In various embodiments, the results of the MS/MS or $MS^n$ analysis are used to assign biomolecule identities to one or more mass signals and to revise which mass-to-charge ratio ranges are subjected to MS/MS or $MS^n$ analysis.

For example, one or more fragmentation spectra can be obtained for a first mass-to-charge ration range from one or more sample portions and based on the one or more fragmentation spectra a biomolecule identity is assigned to the corresponding mass signal and a biomolecule source (e.g., parent protein for a peptide biomolecule identification) assigned to the mass signal corresponding to the first mass-to-charge ratio range. Based on the biomolecule source assignment, the identity of one or more other initially selected peaks may also be assigned without MS/MS or $MS^n$ analysis of the mass-to-charge ratios ranges of these other peaks. In various embodiments, the mass-to-charge ratio ranges corresponding to one or more of these other peaks are not subjected to further MS/MS or $MS^n$ analysis.

In various embodiments, one or more mass peaks with an intensity less than about 80% of the most intense mass peak are selected. In various embodiments, one or more mass peaks with an intensity less than about 70% of the most intense mass peak are selected. In various embodiments, one or more mass peaks with an intensity less than about 80% of the median mass peak intensity are selected. In various embodiments, one or more mass peaks with an intensity less than about 70% of the median mass peak intensity are selected. In various embodiments, mass peaks with an intensity less than about 80% of the mean mass peak intensity are selected. In various embodiments, mass peaks with an intensity less than about 70% of the mean mass peak intensity are selected. In various embodiments, one or more mass peaks with an intensity that is lower than the median mass peak intensity by more than about 1 standard deviation are selected. In various embodiments, one or more mass peaks with an intensity that is lower than the median mass peak intensity by more than about 2 standard deviation are selected. In various embodiments, one or more mass peaks with an intensity that is lower than the median mass peak intensity by more than about 3 standard deviation are selected. In various embodiments, one or more mass peaks with an intensity that is lower than the median mass peak intensity by more than about 4 standard deviation are selected. In various embodiments, one or more mass peaks with an intensity that is lower than the mean mass peak intensity by more than about 1 standard deviation are selected. In various embodiments, one or more mass peaks with an intensity that is lower than the mean mass peak intensity by more than about 2 standard deviation are selected. In various embodiments, one or more mass peaks with an intensity that is lower than the mean mass peak intensity by more than about 3 standard deviation are selected. In various embodiments, one or more mass peaks with an intensity that is lower than the mean mass peak intensity by more than about 4 standard deviation are selected.

In various embodiments, mass spectrometric data based analysis involves selecting mass peaks for further MS/MS or $MS^n$ analysis which are detected with higher intensities. For example, in various investigations in can be desirable to identify the predominant biomolecules present in a sample. In various embodiments, one or more mass peaks with an intensity greater than about 90% of the most intense mass peak are selected. In various embodiments, one or more mass peaks with an intensity greater than about 80% of the most intense mass peak are selected. In various embodiments, one or more mass peaks with an intensity greater than about 90% of the median mass peak intensity are selected. In various embodiments, one or more mass peaks with an intensity greater than about 80% of the median mass peak intensity are selected. In various embodiments, mass peaks with an intensity greater than about 90% of the mean mass peak intensity are selected. In various embodiments, mass peaks with an intensity greater than about 80% of the mean mass peak intensity are selected. In various embodiments, one or more mass peaks with an intensity that is greater than the median mass peak intensity by more than about 1 standard deviation are selected. In various embodiments, one or more mass peaks with an intensity that is greater than the median mass peak intensity by more than about 2 standard deviation are selected. In various embodiments, one or more mass peaks with an intensity that is greater than the median mass peak intensity by more than about 3 standard deviation are selected. In various embodiments, one or more mass peaks with an intensity that is greater than the median mass peak intensity by more than about 4 standard deviation are selected. In various embodiments, one or more mass peaks with an intensity that is greater than the mean mass peak intensity by more than about 1 standard deviation are selected. In various embodiments, one or more mass peaks with an intensity that is greater than the mean mass peak intensity by more than about 2 standard deviation are selected. In various embodiments, one or more mass peaks with an intensity that is greater than the mean mass peak intensity by more than about 3 standard deviations are selected. In various embodiments, one or more mass peaks with an intensity that is greater than the mean mass peak intensity by more than about 4 standard deviations are selected.

As used herein, a "search result based analysis" refers to an analysis that is based, for example, on the putative identification of one or more biomolecules in the sample based on a comparison of at least a portion of one or more of the one or more mass spectra generated by the MS analysis to known or predicted mass spectra. In various embodiments, the measured masses are compared to a reference database of known or predicted mass spectra. For example, a peptide mass fingerprinting (PMF) technique can be used to provide putative identifications. In various embodiments, one or more mass signals associated with a match (within a certain confidence interval) to a mass spectrum in the database are selected for further MS/MS or $MS^n$ analysis. For example, matched peaks can be selected and further analyzed by MS/MS or $MS^n$ to confirm the putative identification determined by the database. In various embodiments, if the initial search results are inconclusive, for example, the higher intensity mass signals corresponding to the inconclusive match, the lower intensity mass signals corresponding to the inconclusive match, or combinations of both, are selected for further analysis by MS/MS or $MS^n$. In various embodiments, one or more mass signals associated with a match (within a certain confidence interval) to a mass spectrum in the database are removed from consideration for further MS/MS or $MS^n$ analysis. For example, matched peaks can be removed from consideration and one or more of the m/z ratio ranges associated remaining unmatched peaks can be selected for MS/MS or $MS^n$ analysis.

In various embodiments, the n most intense mass peaks corresponding to an inconclusive match or no match are selected further analysis by MS/MS or MS$^n$. Examples of values for n include, but are not limited to; values of n in the range from about 1 to about 6. Values for n can be chosen, for example, based on computational resources. In various embodiments, peaks already selected from one mass spectrum are removed from consideration as one of the n most intense peaks in other mass spectra.

For example, consider a first mass signal having a corresponding first mass-to-charge ratio range meets the n most intense criteria in two or more mass spectra. In various embodiments, the first mass signal is considered as one of the n most intense peaks "only" in the mass spectrum where; (1) it is the weakest of the n most intense peaks in the mass spectrum; (2) it is the strongest of the n most intense peaks in the mass spectrum; (3) where it has the highest absolute signal intensity and is one of the n most intense peaks in the mass spectrum; or (4) where it has the lowest absolute signal intensity and is one of the n most intense peaks in the mass spectrum.

In various embodiments, one or more mass peaks corresponding to an inconclusive match or no match with an intensity greater than about 90% of the most intense mass peak corresponding to an inconclusive match or no match are selected. In various embodiments, one or more mass peaks corresponding to an inconclusive match or no match with an intensity greater than about 80% of the most intense mass peak corresponding to an inconclusive match or no match are selected. In various embodiments, one or more mass peaks corresponding to an inconclusive match or no match with an intensity greater than about 90% of the median intensity, of the mass peaks corresponding to an inconclusive match or no match, are selected. In various embodiments, one or more mass peaks corresponding to an inconclusive match or no match with an intensity greater than about 80% of the median intensity, of the mass peaks corresponding to an inconclusive match or no match, are selected. In various embodiments, mass peaks corresponding to an inconclusive match or no match with an intensity greater than about 90% of the mean intensity, of the mass peaks corresponding to an inconclusive match or no match, are selected. In various embodiments, mass peaks corresponding to an inconclusive match or no match with an intensity greater than about 80% of the mean intensity, of the mass peaks corresponding to an inconclusive match or no match, are selected. In various embodiments, one or more mass peaks corresponding to an inconclusive match or no match with an intensity that is greater than the median intensity, of the mass peaks corresponding to an inconclusive match or no match, by more than about 1 standard deviation are selected. In various embodiments, one or more mass peaks corresponding to an inconclusive match or no match with an intensity that is greater than the median intensity, of the mass peaks corresponding to an inconclusive match or no match, by more than about 2 standard deviation are selected. In various embodiments, one or more mass peaks corresponding to an inconclusive match or no match with an intensity that is greater than the median intensity, of the mass peaks corresponding to an inconclusive match or no match, by more than about 3 standard deviation are selected. In various embodiments, one or more mass peaks corresponding to an inconclusive match or no match with an intensity that is greater than the median intensity, of the mass peaks corresponding to an inconclusive match or no match, by more than about 4 standard deviation are selected. In various embodiments, one or more mass peaks corresponding to an inconclusive match or no match with an intensity that is greater than the mean intensity, of the mass peaks corresponding to an inconclusive match or no match, by more than about 1 standard deviation are selected. In various embodiments, one or more mass peaks corresponding to an inconclusive match or no match with an intensity that is greater than the mean intensity, of the mass peaks corresponding to an inconclusive match or no match, by more than about 2 standard deviation are selected. In various embodiments, one or more mass peaks corresponding to an inconclusive match or no match with an intensity that is greater than the mean intensity, of the mass peaks corresponding to an inconclusive match or no match, by more than about 3 standard deviation are selected. In various embodiments, one or more mass peaks corresponding to an inconclusive match or no match with an intensity that is greater than the mean intensity, of the mass peaks corresponding to an inconclusive match or no match, by more than about 4 standard deviation are selected.

In various embodiments, the n least intense mass peaks corresponding to an inconclusive match or match are selected further analysis by MS/MS or MS$^n$. Examples of values for n includes, but are not limited to; values of n in the range from about 1 to about 6. Values for n can be chosen, for example, based on computational resources. In various embodiments, peaks already selected from one mass spectrum are removed from consideration is one of the n most intense peaks in other mass spectra. For example, consider a first mass signal having a corresponding first mass-to-charge ratio range meets the n most intense criteria in two or more mass spectra. In various embodiments, the first mass signal is considered as one of the n most intense peaks "only" in the mass spectrum where; (1) it is the weakest of the n most intense peaks in the mass spectrum; (2) it is the strongest of the n most intense peaks in the mass spectrum; (3) where it has the highest absolute signal intensity and is one of the n most intense peaks in the mass spectrum; or (4) where it has the lowest absolute signal intensity and is one of the n most intense peaks in the mass spectrum.

In various embodiments, one or more mass peaks corresponding to an inconclusive match or no match with an intensity less than about 80% of the most intense mass peak corresponding to an inconclusive match or no match are selected. In various embodiments, one or more mass peaks corresponding to an inconclusive match or no match with an intensity less than about 70% of the most intense mass peak corresponding to an inconclusive match or no match are selected. In various embodiments, one or more mass peaks corresponding to an inconclusive match or no match with an intensity less than about 80% of the median intensity, of the mass peaks corresponding to an inconclusive match or no match, are selected. In various embodiments, one or more mass peaks corresponding to an inconclusive match or no match with an intensity less than about 70% of the median intensity, of the mass peaks corresponding to an inconclusive match or no match, are selected. In various embodiments, mass peaks corresponding to an inconclusive match or no match with an intensity less than about 80% of the mean intensity, of the mass peaks corresponding to an inconclusive match or no match, are selected. In various embodiments, mass peaks corresponding to an inconclusive match or no match with an intensity less than about 70% of the mean intensity, of the mass peaks corresponding to an inconclusive match or no match, are selected. In various embodiments, one or more mass peaks corresponding to an inconclusive match or no match with an intensity that is lower than the median intensity, of the mass peaks corresponding to an inconclusive match or no match, by more than about 1 standard deviation are selected. In various embodiments, one or more mass peaks corresponding to an inconclusive match or no match with an intensity that is lower than the median intensity, of the mass peaks corresponding to an inconclusive match or no match, by more than about 2 standard deviation are selected. In various embodiments, one or more mass peaks corresponding to an inconclusive match or no match with an intensity that is lower than the median intensity, of the mass peaks corresponding to an inconclusive match or no match, by more than about 3 standard deviation are selected. In various embodiments, one or more mass peaks corresponding to an inconclusive match or no match with an intensity that is lower than the median intensity, of the mass peaks corresponding to an inconclusive match or no match, by more than about 4 standard deviation are selected. In various embodiments, one or more mass peaks corresponding to an inconclusive match or no match with an intensity that is lower than the mean intensity, of the mass peaks corresponding to an inconclusive match or no match, by more than about 1 standard deviation are selected. In various embodiments, one or more mass peaks corresponding to an inconclusive match or no match with an intensity that is lower than the mean intensity, of the mass peaks corresponding to an inconclusive match or no match, by more than about 2 standard deviation are selected. In various embodiments, one or more mass peaks corresponding to an inconclusive match or no match with an intensity that is lower than the mean intensity, of the mass peaks corresponding to an inconclusive match or no match, by more than about 3 standard deviation are selected. In various embodiments, one or more mass peaks corresponding to an inconclusive match or no match with an intensity that is lower than the mean intensity, of the mass peaks corresponding to an inconclusive match or no match, by more than about 4 standard deviation are selected.

In various embodiments, fractions of a biological sample eluting from a liquid chromatographic (LC) column are processed and deposited, as discrete samples or as a continuous sample, on a substrate for introduction into an MS apparatus by a MALDI procedure. The sample can be analyzed by a time-of-flight mass spectrometer (TOF-MS) to produce one or more spectra of mass peaks representing the identity and relative abundance of a plurality of biomolecules. Based upon the one or more spectra generated by the MS process, a decision can be made as to which generated peaks warrant further analysis by a subsequent MS/MS process. In various embodiments of a search result based analysis, the peak list of the mass spectra can be stored in a computer and the biomolecules corresponding to one or more peaks can be identified by correlating the information contained in the sample mass spectra with known or theoretical mass spectra. Based on the identification result, the biomolecules associated with one or more peaks can be selected for further MS/MS analysis and identification. In various embodiments of an expression based analysis and various embodiments of a mass spectrometric based analysis, the MS process can be exploited to produce one or more spectra of mass peaks representing the relative abundance of those biomolecules which can be selected for further MS/MS analysis and identification. Since multiple portions of a sample are deposited on the substrate (e.g., as discrete samples or as an extended sample), another portion of a sample can be reanalyzed by a MALDI MS/MS process in the same manner that the initial portion of the sample was analyzed. For example a single spot or a MALDI sample plate can contain sufficient material for multiple reanalysis. Based on knowledge gained in the initial analysis, adjustments can be made during a subsequent analysis, such as, for example, adjusting the number of laser shots for acquisition or peak detection, or deisotoping settings for reprocessing or subsequent analysis. Thus, analysis of a given sample can be repeated based on results obtained from an initial analysis.

Suitable instruments for practicing the methods of the invention include, but are not limited to, MALDI MS/MS instruments and MALDI MS$^n$ instruments. Suitable instruments can include a relational database or object oriented database to manage and store MS related data. Suitable instruments can include a LC device where liquid fractions from the LC device can be directly deposited from an infusion device, such as uni- or multidimensional microcapillary liquid chromatography ($\mu$LC), and mixed with a suitable matrix, onto a MALDI plate so that discrete spots, or sets of discrete spots, correspond to traditional chromatography fractions. In various embodiments, the traditional chromatography fractions correspond to different samples of biomolecules.

Subsequent to loading with samples, the MALDI plate can be placed in the ion source chamber of a mass spectrometer and a portion of the sample can be desorbed, such as with a pulsed laser beam, to form an ionized vapor sample that can be analyzed by MS to generate a mass spectrum. The process can be repeated for the other sample portions on the MALDI plate and other MALDI plates to generate further mass spectra. Based on one or more of these mass spectra, one or more m/z ranges are then selected for further analysis by MS/MS or MS$^n$. The process of MS and MS/MS runs, quantitation, and identification can be iterated using other portions of the sample with modified process parameters until reliable results can be derived for identification of one or more biomolecules in the sample.

In various embodiments, sample preparation uses a standard which is differentially labeled with detectable labels (such as, e.g., isotopic labels) with respect to the sample so that constituents of the sample can be compared with constituents of the standard thereby to provide a determination as to how the sample differentiates from the standard. The standard can be an internal standard (for example, mixed with the sample or co-deposited in the matrix with sample), an external standard (for example, prepared under substantially the same conditions as the sample and deposited on a MALDI plate in one or more portions discrete from the sample portions), or a combination of both.

In various embodiments, the determination of how the sample under investigation differentiates from a standard sample or control sample can provide, for example, information on one or more of: (1) whether the sample is indicative of, for example, a disease state; (2) how the sample reacts to a stimulus such as a drug, an environmental change or the like; (3) information for calibration of the mass scale of a mass spectrum; (4) information for calibration of the intensity scale of a mass spectrum; and (5) information for assessing the reliability or setting reliability thresholds for biomolecule identification based on one or more mass spectra or fragmentation spectra.

In various aspects, the present teachings provide methods for analyzing a sample containing biomolecules which, in various embodiments, facilitate the identification of biomolecules in a sample containing biomolecules. Referring to FIG. 1, a flow diagram 100 illustrating various embodiments of methods for analyzing a sample containing biomolecules is shown. In various embodiments, the methods start by providing a plurality of sample portions of a sample containing biomolecules 102. In various embodiments, mass spectra of one or more sample portions for one or more samples are acquired 104 and, in various embodiments, to generate a data set comprising a list of mass signals 106.

The data set can be stored in a database (e.g., in the mass spectrometry instrument's computer system, on a computer-readable medium). The database can also be used to store process information such as, for example, location information of the sample portion from which the spectrum was obtained, and experimental parameters used in obtaining the mass spectrum. For example, a mass spectrum is typically the average of a number of laser shots directed at the same sample location on the sample plate. In various embodiments, each sample plate can be coded, such as by bar code, and each sample on a plate can be addressed by unique x and y coordinates to define unique locations for the samples across a plate that can be correlated to the peak lists stored in the database. The storing of location information, for example, facilitates subsequent MS/MS or $MS^n$ analysis, or MS reanalysis, of certain samples by unique addressable locations.

Referring again to FIG. 1, one or more mass spectra are analyzed 108 using one or more of an expression based analysis 110, a mass spectrometric data based analysis 112, and a search results based analysis 114 to select one or more mass-to-charge ratio (m/z) ranges for analysis by MS/MS or $MS^n$ 116. In various embodiments, the analysis of the one or more mass spectra 108 generates a first set of selection criteria for selecting the m/z ranges of the precursor ions based on the data generated in the analysis of the one or more mass spectra 108. The analysis of the mass spectrum 108 by two or more of an expression based analysis 110, a mass spectrometric data based analysis 112, and a search results based analysis 114 can be conducted substantially in parallel, in series, or combinations thereof. For example, electronic copies of the mass spectra, and/or a corresponding data set of mass signals, can be submitted substantially in parallel for analysis. The results of one analysis can be the basis for initiating or refining another analysis. For example, the results of a mass spectrometric data based analysis 112 can be used to initiate or refine 118 (e.g., by reanalysis with different parameters) a search results based analysis 114. For example, the results of a search results based analysis 114 can be used to initiate or refine (e.g. by removing certain peaks from consideration for MS/MS or $MS^n$ analysis) a mass spectrometric data based analysis 112 and/or an expression based analysis 110. In various embodiments, the results of the analysis of the one or more mass spectra 108 can be the basis for initiating acquisition of additional mass spectra 120. For example, additional mass spectra can be acquired and added to the initial mass spectrum to improve signal-to-noise (S/N).

In various embodiments, the initial one or more mass spectrums can be spectrums generated by a single laser pulse and additional mass spectra can be added to the one or more initial mass spectrums until a certain quality metric for the resultant mass spectrums is reached. A quality metric can be generated for each mass spectrum based on criteria such as, for example, the number of peaks over a given signal to noise ratio, or the fraction of the spectrum exceeding a given total ion count.

Referring again to FIG. 1, in various embodiments, the expression based analysis 110 comprises determining the expression ratios of differentially labeled samples 122, and can include compensating for sample bias 124. Sample bias can arise from systematic errors, which include, but are not limited to, unequal amounts of starting material or sample handling errors. The expression ratios can be corrected for bias by adjusting the expression ratios using the median expression ratio or the mean expression ratio. In various embodiments, the expression based analysis 110 generates a data set of quantitation information (i.e., the relative abundances of differentially labeled pairs) 126 for the one or more mass spectra.

In various embodiments, the expression based analysis generates precursor selection criteria, that is, criteria for selecting mass-to-charge ratio ranges for further MS/MS or $MS^n$ analysis, that requires one or more of the following criteria to be met by a mass signal (of the MS mass spectrum) associated with the mass-to-charge ratio range: (1) the mass signal shows a greater than 2-fold change in expression level relative to its differentially labeled partner; (2) the expression level ratio of the mass signal and its partner is more than 2 standard deviations away from the mean expression level ratio distribution; (3) the mass signal expression level (e.g., signal intensity) is greater than a certain signal-to-noise (S/N) threshold; (4) the mass signal is the most intense peak of its differentially labeled pair; (5) the mass signal is up-regulated; and (6) the mass signal is down-regulated.

In various embodiments, the mass spectrometric data based analysis generates precursor selection criteria that based on one or more of the following criteria for a mass signal (of the one or more MS mass spectra) associated with the mass-to-charge ratio range: (1) the absolute mass signal intensity; (2) the relative mass signal intensity; (3) the mass signal intensity relative to a S/N threshold; and (4) the mass signal peak area.

In various embodiments, a mass spectrometric based analysis can include a mass exclusion list to exclude, for example, mass ranges not of interest, masses below or above a mass cut-off, masses associated with known contaminants, adducts and mass signals identified (within a certain confidence interval) by a search result based analysis. In various embodiments, a mass spectrometric based analysis selects mass signals for further analysis by MS/MS or $MS^n$ based on the intensity of the peak cluster area over a series of mass spectra determined by a LC elution profile of the corresponding peak that can be generated from peak masses within a specified mass tolerance window in successively deposited MALDI spots.

Referring again to FIG. 1, the search result based analysis 114 comprises comparing of at least a portion of the one or more mass spectra to known or predicted mass spectra to assign potential identities to one or more mass signals in the one or more mass spectra 128. More than one potential identity can be assigned per mass signal. For example, a peptide mass fingerprinting (PMF) technique can be used to assign potential identities to mass signals in the one or more mass spectra. In various embodiments, the identity assignments are ranked, assigned a confidence level, or both. In various embodiments, the search result based analysis 114 generates a data set comprising a list of mass signals and their identity assignments 130. The data set comprising a list of mass signals and their identity assignments 130 can further comprise information on the rank and/or confidence level of the assignment.

In various embodiments, the search result based analysis generates precursor selection criteria that requires one or more of the following criteria to be met by a mass signal (of the MS one or more mass spectra) associated with the mass-to-charge ratio range: (1) identified with a level of confidence greater than about 95%; (2) identified with a level of confidence greater than about 90%; (3) identified with a level of confidence less than about 90%; (4) identified with a level of confidence less than about 80%; (5) identified with a level of confidence less than about 90% and greater than about 80%; (6) identified with two or more biomolecules; (7) identified with one or more biomolecules of interest; and (8) not identified or matched with a biomolecule.

Referring again to FIG. 1, one or more criteria generated by one or more of the expression based, mass spectrometric data based, and search result based analyses can be used to select precursor ions (m/z ranges) for further analysis by MS/MS or $MS^n$. For example, the m/z ranges of mass signals that have PMF search result scores above a confidence threshold of 95% in a search result based analysis and that have a signal-to-noise above 10 and a cluster area above 1000, were selected as precursor ions.

Referring again to FIG. 1, a fragmentation spectrum of at least one of the sample portions at one or more of the selected precursor ion m/z ranges is acquired 140. MS/MS acquisition and processing can be performed on a MALDI tandem TOF. Various other suitable mass spectrometry systems for performing MS/MS and/or $MS^n$ are also described below.

In various embodiments, fragmentation spectra representing mass peak lists of fragment (daughter) ions are linked with the spectra of the parent ions and stored in the database 142. A quality metric can be generated for each fragmentation spectrum based on criteria such as the number of peaks over a given signal to noise ratio, the fraction of the spectrum exceeding a given total ion count, the presence of immonium ions at given mass values, or the presence of y1 ions indicating that lysine or arginine is at the peptide carboxy-terminus, or the presence of ICAT reagent derived masses.

At least a portion of one or more fragmentation spectra are compared to known or predicted mass spectra to assign potential identities to one or more biomolecules in the sample 144. In various embodiments, fragmentation spectra peak lists are generated from one or more fragmentation spectra and compared to a MS/MS ion and sequence database to assign potential biomolecule identities to one or more mass signals. A list of the assigned biomolecule identifications of one or more mass signals can be generated 146, which can include, for example, quantitation information.

Various decisions can be made based on the assigned biomolecule identifications 150. In various embodiments, the assigned biomolecule identifications can be used to determine whether a biomolecule is present in the sample 150. In various embodiments, the analysis of the sample containing biomolecules can be complete if enough confidence in the identification is obtained 152. For example, database search 144 or MALDI re-analysis can be initiated with modified parameters, which can be performed either immediately or at a later time. Sequence determination algorithms, taking into account, for example, amino acid composition, mass tags or sequence tags, can be used to confirm results 154. Spectra that are still not confidently identified or are unidentified can be submitted, for example, to a de novo sequence determination algorithm 154 followed by a MS-BLAST search to identify similar protein sequences.

In various embodiments, iteration MS acquisition 155, MS/MS or $MS^n$ acquisition 156 and/or MS/MS or $MS^n$ identifications are also possible. Iterative database searches can be performed by selecting high confidence identified proteins in a first pass, followed by a search 144 against the subset of proteins already identified, with a new set of search parameters. In various embodiments, the search parameter iteration is conducted to facilitate explaining more peaks in the data set and/or to gain confidence in results. For example, missed or non-specific enzyme cleavages, or unexpected chemical and post-translational modifications can cause some spectra to be unidentified in the first pass. A second pass database search can be performed against a relative small set of proteins, already identified, but with consideration of more chemical and post-translational modifications or even amino acid substitutions. A difference between a database sequence and the observed sequence may be due to a DNA sequencing error, a mutation or polymorphism, an alternative splice form, or more extensive evolutionary changes, that, the database entry may not be the authentic protein, but a related sequence from a different species.

In various embodiments, the quantitation information can be compared to the assigned biomolecule identifications to evaluate whether there are discrepancies with the search results. The quantitation information can be corrected 160 when there are discrepancies between the quantitation information and the search results that assign potential biomolecules.

In various embodiments, the theoretical masses of biomolecules (e.g., peptides) that are identified with high confidence in those first rounds of MS/MS or $MS^n$ acquisition and analysis can be used to recalibrate the MS data 160. In various embodiments, the number of reference masses for recalibration across MALDI plate wells can be increased, for each theoretical mass, by identifying peak masses within a specified tolerance window in successively deposited MALDI spots along the $\mu$LC peptide elution profile. The fragment spectrum search 144 can be repeated by setting tighter search tolerances for recalibrated precursors and by retaining the original search tolerance for the non-recalibrated ones, to facilitate obtaining additional or higher confidence hits, but also fewer false positive identifications. Recalibrated MS masses can be further investigated by increasing the database search space to include peptide variations derived in-silico from those proteins, and, in various embodiments, putatively identified peptides and modifications could then be verified by subsequent MS/MS or $MS^n$ analysis.

In various embodiments, labeling of biomolecules with isotopically coded affinity reagents such as, for example, the ICAT™ reagent method can be used to provide expression dependent data for expression based analysis of mass spectra. In various embodiments, a MALDI mass spectrometric method (e.g., MS, MS/MS, $MS^n$) can be used to provide mass spectra for identification and quantitation of one or more proteins in a sample using isotopically labeled protein reactive reagents (such as, e.g., isotope coded affinity tags) to provide expression dependent data for expression based analysis. In various embodiments, the expression based analysis facilitates the quantitative analysis of proteomes.

In various embodiments, sample preparation employs differentially isotopically labeled protein reactive reagents that allow for the selective isolation of peptide fragments or the products of reaction with a given protein (e.g., products of enzymatic reaction) from complex mixtures as described in published PCT patent application WO 00/112084, the entire contents of which are incorporated herein by reference. In various embodiments, the isolated peptide fragments or reaction products can be characteristic of the presence of a protein or the presence of a protein function, e.g., an enzymatic activity, respectively, in those mixtures. Isolated peptides, reaction products, or both, can be characterized by mass spectrometric techniques to provide for quantitative analysis of protein expression profiles in cells and tissues. The sequence of isolated peptides can be determined using tandem mass spectrometry (MS/MS) techniques or multidimensional (MS$^n$) techniques. For example, by searching a database containing fragmentation spectra for various precursor ions (e.g., MS/MS ion and sequence databases) to identify the protein from which the sequenced peptide originated. In various embodiments, the differentially isotopically labeled protein reactive reagents provide for differential isotopic labeling of the isolated peptides or reaction products which facilitates quantitative determination of the relative amounts of proteins in different samples by mass spectrometry. In various embodiments, differentially isotopically labeled reagents can serve as internal standards that facilitate the quantitative determination of the absolute amounts of one or more proteins or reaction products present in the sample.

In various embodiments, the isotope coded affinity labeled protein reactive reagents have three portions: an affinity label (A) covalently linked to a protein reactive group (PRG) through a cleavable linker group (L) that includes an isotopically labeled linker. The linker can be directly bonded to the protein reactive group (PRG). The affinity labeled protein reactive reagents can have the formula:

The linker can be differentially isotopically labeled, e.g., by substitution of one or more atoms in the linker with a stable isotope thereof. For example, hydrogens can be substituted with deuteriums ($^2$H) and/or $^{12}$C substituted with $^{13}$C. Utilization of $^{13}$C promotes co-elution of the heavy and light isotopes in reversed phase chromatography.

The affinity label (A) functions as a means for separating reacted protein from unreacted protein in a sample, such as by multidimensional liquid chromatography (MDLC). In various embodiments, the affinity label comprises biotin. After reaction of the PRG portion of the reagent with protein, MDLC can be used to separate unlabeled components of the sample from the reacted protein bound to the PRG moiety. Thereafter, the cleavage of the cleavable linker (L) can be effected such as, for example, chemically, enzymatically, thermally or photochemically to release the isolated materials for MS analysis. In various embodiments, the linker can be acid-cleavable. Prior to MS analysis, the bound protein can be digested to form peptides including bound peptides which can be analyzed by MS. The protein digestion step can precede or follow cleavage of the cleavable linker.

In various embodiments, the insertion of an acid cleavable linker can result in a smaller and more stable label. A smaller and more stable linker can afford enhanced MS/MS fragmentation which can result in more confident protein identification and greater depth of proteome coverage.

In various embodiments, using a biotin affinity label can significantly reduce the complexity of a peptide mixture because biotinylated cysteine-containing peptides are selectively isolated. For example, the NCBInr Database (v02.13.2003) contains 9821 *S. Cerevisiae* sequences, but only 30,095 unique cysteine containing tryptic peptides. This number is consistent with the predicted 30,619 peptides containing a cysteine residue (out of 344,855 peptides), produced by a theoretical tryptic digest of the entire *S. Cerevisiae* yeast proteome (6,113 proteins).

Examples of PRG groups include, but are not limited to: (a) those groups that selectively react with a protein functional group to form a covalent or non-covalent bond tagging the protein at specific sites, and (b) those that are transformed by action of the protein, e.g., that are substrates for an enzyme. In various embodiments, a PRG can be a group having specific reactivity for certain protein groups, such as specificity for sulfhydryl groups. Such a PRG can be useful, for example, in general for selectively tagging proteins in complex mixtures. For example, a sulfhydryl specific reagent tags proteins containing cysteine. Additional embodiments of isotope coded affinity labeled protein reactive reagents are described in the aforementioned PCT patent application which can be referred to if further details are desired.

In various embodiments, a PRG group that selectively reacts with certain groups that are typically found in peptides (e.g., sulfhydryl, amino, carboxy, homoserine, lactone groups) can be introduced into a mixture containing proteins. In various embodiments, after reaction with the PRG, proteins in the complex mixture are cleaved, e.g, enzymatically, into a number of peptides. In various embodiments, the resultant peptides are isolated by MDLC and are analyzed such as by liquid chromatography/mass spectrometry (LC/MALDI). In various embodiments, the sequence of one or more tagged peptides can then be determined by MS/MS or MS$^n$ techniques, to identify one or more proteins present in a mixture by searching databases of MS/MS or MS$^n$ data. In some embodiments, a digestion step (e.g., enzymatic cleavage) may not be necessary, where, for example, the proteins are relatively small.

In various embodiments, quantitative relative amounts of proteins in one or more different samples containing protein mixtures (e.g., biological fluids, cell or tissue lysates, etc.) are labeled with chemically identical, and differentially isotopically labeled reagents comprising an affinity label cleavably linked to a protein reactive group with an isotopically labeled linker group. Labeled peptides originating from different samples are differentially isotopically labeled. The different samples can be, for example, control vs. experimental, samples from different points in time (e.g., to form a histological sequence), disease vs. normal, experimental vs. disease, etc. In various embodiments, the treated samples are then combined and the proteins in the combined sample are enzymatically digested, if necessary, to generate peptides. In various embodiments, the different samples are combined in substantially equal amounts. In various embodiments, labeled peptides are isolated by MDLC using affinity chromatography, cleaved from the linker and analyzed by LC/MALDI MS. Peptides characteristic of their protein origin can be sequenced using MS/MS or MS$^n$ techniques to identify of proteins contained in the samples. In various embodiments, the expression based analysis determines the relative amounts of a given protein in each sample by comparing the relative abundances of the ions generated from differentially labeled peptides originating from that protein. In various embodiments, expression based analysis assesses the relative amounts of known proteins in different samples that can be indicative of protein expression levels.

In various embodiments, isotope coded affinity labeled protein reactive reagents can be used which focus on subclasses of peptides (e.g. phosphorylation) and/or multiplexing, so that within one experimental run, for example, multiple mutant strains can be compared with a wild type; or in a time course scenario, multiple dosage levels can be assessed against a baseline; or different isolates of cancer tissue can be evaluated against normal tissue.

In various embodiments, expression based analysis using isotope coded affinity labeled protein reactive reagents can be used, for example, to uncover post-translational modifications (PTM's), and to identify additional (relatively) low abundant protein by, for example, determining precursor selection criteria, that facilitate selecting proteins with PTM's, low abundant proteins, or both, for further analysis by MS/MS or $MS^n$. In various embodiments, the determination of precursor selection criteria using a expression based analysis focuses analytical instrument resources and time on studying the proteins of interest. In various embodiments, such a selective approach versus a shotgun approach (e.g., perform MS/MS on all mass peaks) can increase sample throughput.

In various embodiments, expression dependent analysis can be applied to screen for and identify proteins which exhibit differential expression in cells, tissue or biological fluids. In various embodiments, an expression dependent analysis determines precursor selection criteria based on the differential expression data. In various embodiments, differences in intensities for a set of corresponding mass peaks in a mass spectrum acquired by a MS analysis can reveal differences from the expected constant biological expression profile of the majority of the proteins in the sample.

Figure 2A:
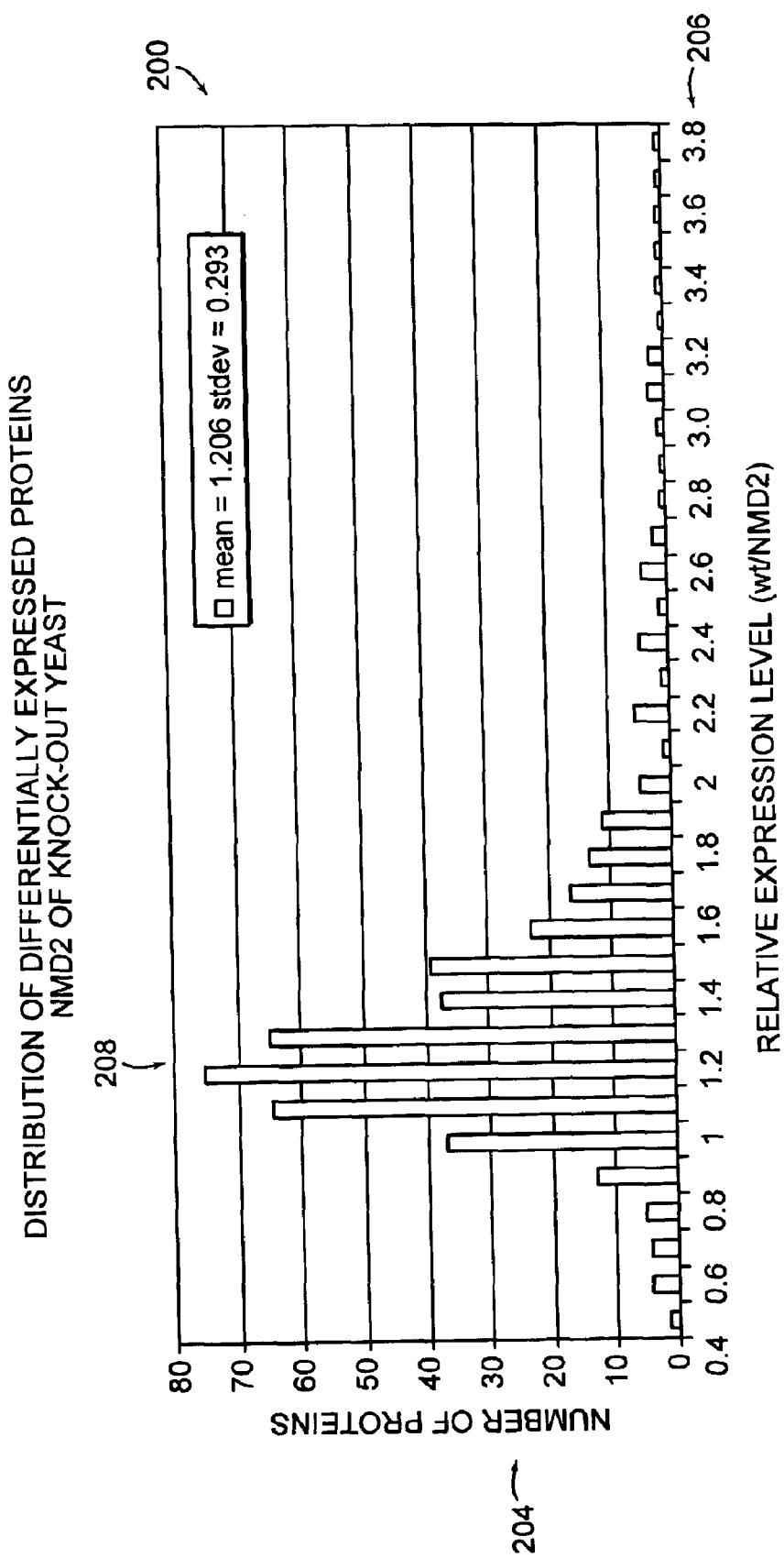
FIGS. 2A and 2B are charts illustrating various embodiments of expression dependent correction and selection.

For example, FIG. 2A charts a distribution of protein differential expression levels 200 in the wild type of *Saccharomyces cerevisiae* relative to the nonsense mediated mRNA decay (NMD) 2 knock-out strain, where nominally equal amounts of knock-out and wild type sample material are compared. FIG. 2A charts the number of proteins 204 having various relative expression level ratios 206 (wild type:NMD2). Notice that the expression level from the wild type and mutant samples are not exactly equal and that the mean of the distribution 208 is around 1.2 and the standard deviation is 0.293. The bias can be due, for example, to unequal amounts of starting material or sample handling errors. In various embodiments, the expression ratios can be corrected for bias by adjusting the expression ratios using the median expression ratio or the mean expression ratio.

Figure 2B:
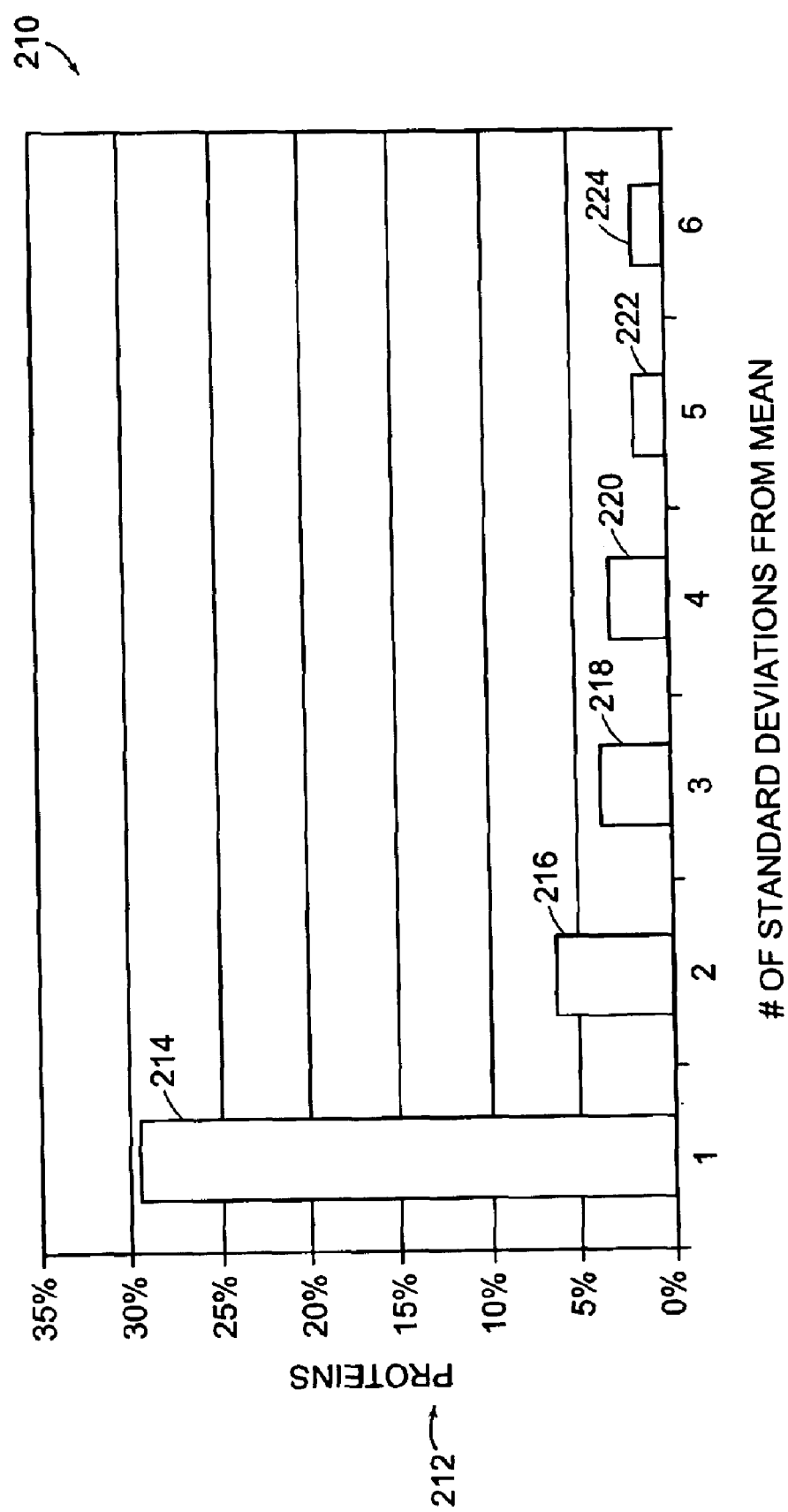

In various embodiments, further analysis using MS, MS/MS or $MS^n$ can be performed on peaks selected using a set of criteria (precursor selection criteria) based on the expression dependent data. In various embodiments, the expression based analysis selects only peaks which evidence expression changes above a two-fold threshold (e.g., expression level ratios below 0.5 or above 2.0), which evidence expression ratios a certain number of standard deviations ($\sigma$) from the mean, or both. For example, FIG. 2B charts the number of proteins falling within in various standard deviation bands about the center of the distribution 210 of FIG. 2A. FIG. 2a charts the number of proteins 212 falling within one standard deviation 214, between one and two standard deviations ($\sigma$) 216, between two and three $\sigma$ 218, between three and four $\sigma$ 220, between four and five $\sigma$ 222, and between five and six $\sigma$ 224. In FIGS. 2A and 2B, four standard deviations approximately correspond to a two-fold change in expression level.

In various embodiments, the expression based analysis selects mass-to-charge ratio ranges for further MS/MS or $MS^n$ analysis where one or more of the following criteria are met by a mass signal (of the one or more MS mass spectra) associated with the mass-to-charge ratio range: (1) the mass signal shows a greater than 2-fold change in expression level relative to it isotopic partner; (2) the expression level ratio of the mass signal and its isotopic partner is more than 2 standard deviations away from the mean expression level ratio distribution; (3) the mass signal expression level (e.g., signal intensity) is greater than a certain signal-to-noise (S/N) threshold; (4) the mass signal is the most intense peak of its isotope pair; (5) the mass signal is up-regulated; and (6) the mass signal is down-regulated.

Figure 3:
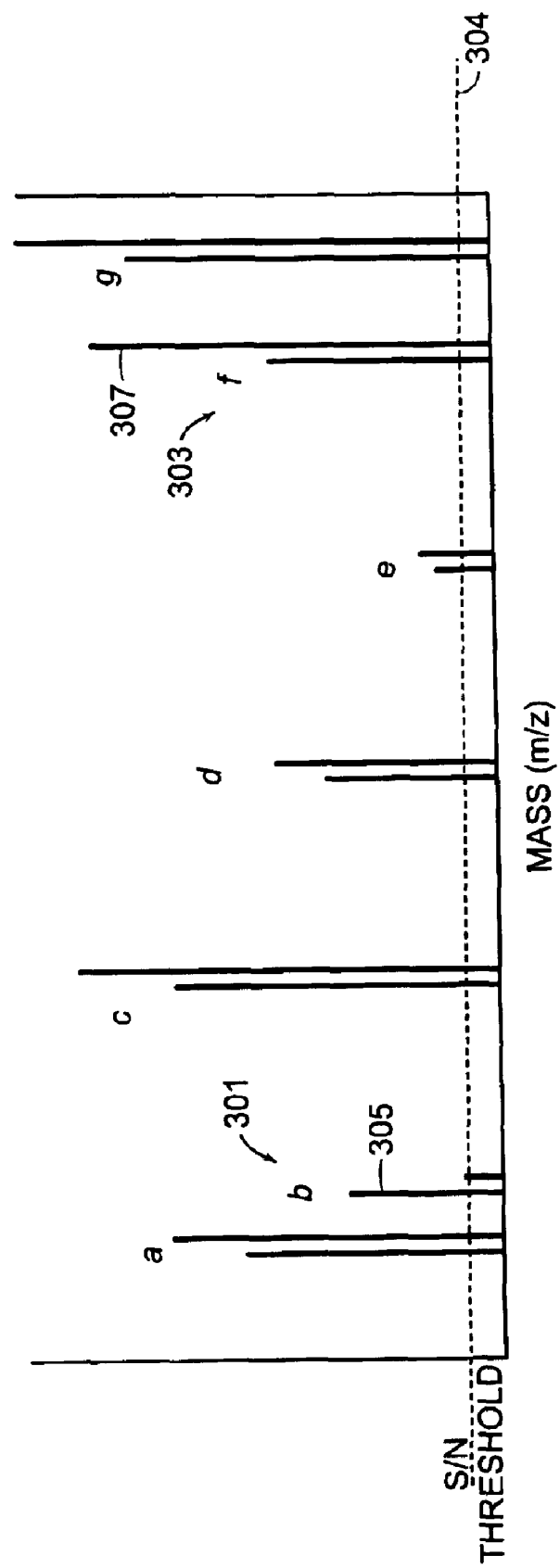
FIG. 3 is a schematic illustration of hypothetical mass spectra of an isotope coded affinity reactive reagent labeled sample.

Referring to FIG. 3, various embodiments for selection of peaks for further investigation by MS/MS or $MS^n$ using expression dependent data in an expression dependent analysis can be illustrated. FIG. 3 shows a series of hypothetical light/heavy isotope pairs (a–g). As illustrated, mass pair b 301 and mass pair f 303 have an isotope ratio that deviates more than 2 standard deviations from the average ratio, and mass pair b 301 is the only pair showing a greater than 2-fold change in expression level. In various embodiments using the precursor selection criteria of (1) in the immediately preceding paragraph, only the mass-to-charge ratio ranges associated with the mass signals of pair b 301 are selected for further MS/MS or $MS^n$ analysis. In various embodiments using the precursor selection criteria of (2) in the immediately preceding paragraph, only the mass-to-charge ratio ranges associated with the mass signals of pairs b 301 and f 303 are selected for further MS/MS or $MS^n$ analysis. In various embodiments using the precursor selection criteria of (3) in the immediately preceding paragraph, only the mass-to-charge ratio ranges associated with mass signals above the S/N threshold 304 are selected for further MS/MS or $MS^n$ analysis (here mass pairs a and c–g and the light isotope mass 305 of pair b). In various embodiments using the precursor selection criteria of (1) and (4) 301 in the immediately preceding paragraph, only the mass-to-charge ratio ranges associated with the more intense mass signal (light isotope) 305 of mass pair b 301 is selected for further MS/MS or $MS^n$ analysis. In various embodiments using the precursor selection criteria of (2) and (4) in the immediately preceding paragraph, only the mass-to-charge ratio ranges associated with the more intense mass signal (light isoptope) 305 of mass pair b 301 and the more intense signal (heavy isotope) 307 of mass pair f 303 are selected for further MS/MS or $MS^n$ analysis. In various embodiments using the precursor selection criteria of (1), (2) and (4) in the immediately preceding paragraph, only the mass-to-charge ratio ranges associated with the more intense mass signal (light isoptope) 305 of mass pair b 301 is selected for further MS/MS or $MS^n$ analysis.

Figure 4:
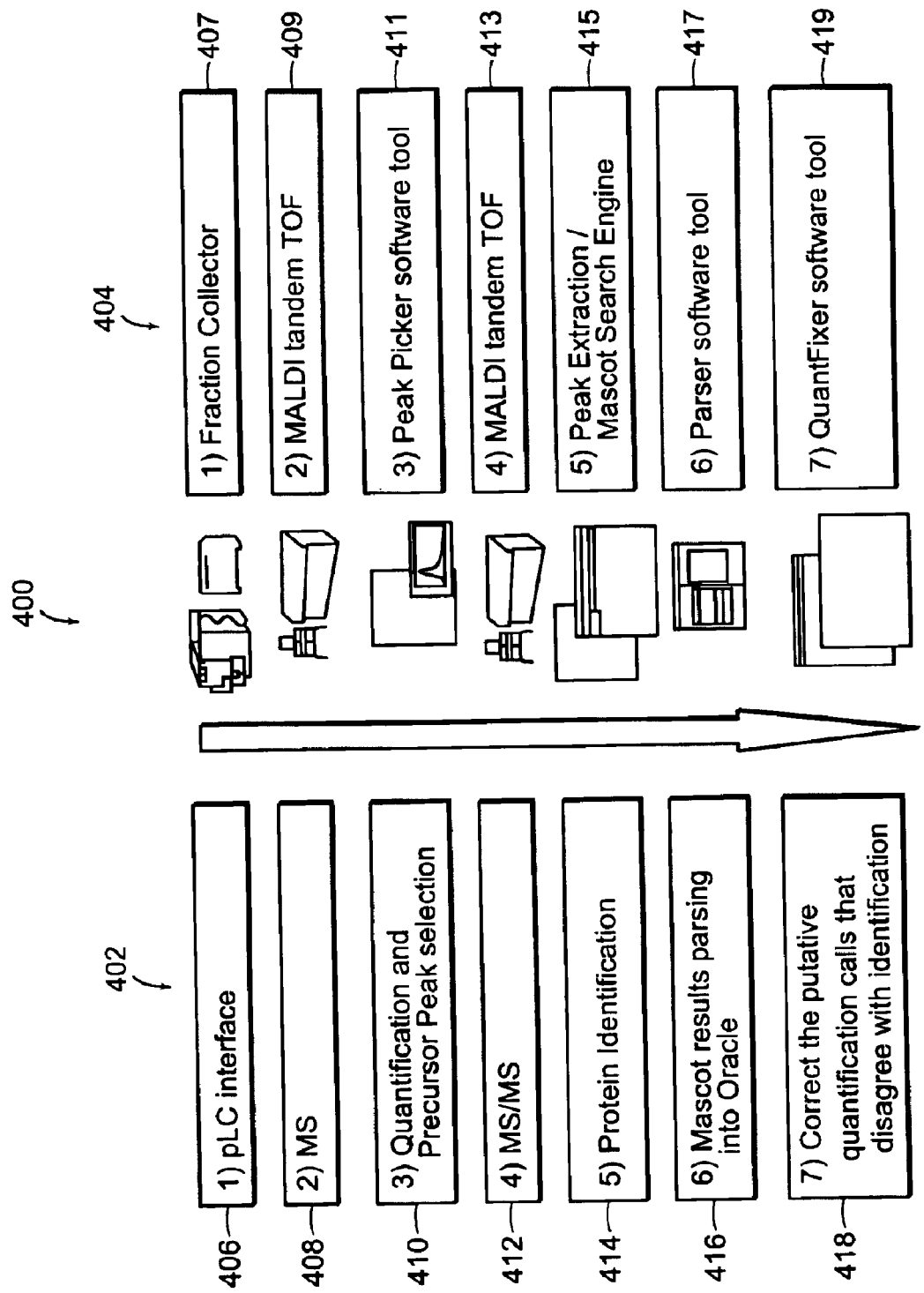
FIG. 4 is a flow diagram illustrating various embodiments utilizing an expression data dependent workflow.

Referring to FIG. 4, in various embodiments, methods for an expression data dependent workflow are shown in the flow diagram 400 where left hand column 402 illustrates a series of steps and the right hand column 404 non-limiting examples of tools for accomplishing the steps. The expression data dependent workflow in FIG. 4 presents various embodiments of the data processing steps and does not illustrate, for example, upstream sample preparation, sample labeling, sample pooling, sample digestion (e.g., with trypsin), fractionation by strong cation exchange (SCX), or affinity isolation and cleavage. FIG. 4 is discussed in the context of a sample containing proteins. Various software tools are discussed in the context of FIG. 4. Peak Picker™ (Applied Biosystems), Peak Extraction™, Parser™ and QuantFixer™ are software tools that can be used to quantify and organize the peptides and proteins identified by the Mascot sequence searching program, and link and store MS, MS/MS, quantitation and identification-related information in a relational database.

Referring to FIG. 4, in various embodiments, an expression data dependent workflow includes sample preparation using an ICAT reagent method; the peptide mixtures retained after the affinity isolation and cleavage can be further separated 406 by μLC and collected onto MALDI plates by the fraction collector 407. A MS analysis 408 can be then performed on the MALDI tandem TOF 409, operated in MS mode, to acquire one or more mass spectra. The number of laser shots and search pattern positions can be optimized in order to generate reproducible relative peak abundances for quantitation. The quantitation and expression based analysis of the MS data to select precursors for further MS/MS analysis 410 can be performed with the Peak Picker software tool 411.

TABLE 1

$$\bar{x}_{Protein} = e^{\bar{x}'_{Protein}}, sd_{Protein} = e^{(\bar{x}'_{Protein} + sd'_{Protein})} - e^{\bar{x}'_{Protein}}, \quad (1)$$
$$cf_{1sd_{Protein}} = \langle e^{\bar{x}'_{Protein} - sd'_{Protein}} \mid e^{\bar{x}'_{Protein} + sd'_{Protein}} \rangle$$

$$\bar{x}_{Peptide} = e^{\bar{x}'_{Peptide}}, sd_{Peptide} = e^{(\bar{x}'_{Peptide} + sd'_{Peptide})} - e^{\bar{x}'_{Peptide}}, \quad (2)$$
$$cf_{1sd_{Peptide}} = \langle e^{\bar{x}'_{Peptide} - sd'_{Peptide}} \mid e^{\bar{x}'_{Peptide} + sd'_{Peptide}} \rangle$$

where $$\bar{x}'_{Protein} = \frac{\sum_{i=1}^{N} \omega_i \times \ln(\bar{x}_{Peptide(i)})}{\sum_{i=1}^{N} \omega_i} \quad (1.1)$$

$$sd'_{Protein} = \sqrt{\frac{\sum_{i=1}^{N} \omega_i \times (\ln(\bar{x}_{Peptide(i)}) - \bar{x}'_{Protein})^2}{(N-1) \times \left(\sum_{i=1}^{N} \omega_i / N\right)}}$$

$$\bar{x}'_{Peptide} = \frac{\sum_{j=1}^{M} \upsilon_j \times \ln(x'_{Peptide(j)})}{\sum_{j=1}^{M} \upsilon_j} \quad (2.1)$$

$$sd'_{Peptide} = \sqrt{\frac{\sum_{j=1}^{M} \upsilon_j \times (\ln(x_{Peptide(j)}) - \bar{x}'_{Peptide})^2}{(M-1) \times \left(\sum_{j=1}^{M} \upsilon_j / M\right)}}$$

and
i: = 2 to N, N = # of associated Peptides with MS/MS ion search confidence greater threshold (e.g. >95%, p < 0.05)
j: = 2 to M, M = # of pairs along Peptide elusion Profile, where $I_{LIGHT}(j) + I_{HEAVY}(j) > 0$ $x_{Peptide(j)} = (I_{HEAVY(j)}/I_{LIGHT(j)})/\eta$
$\upsilon_j = I_{LIGHT(j)} * I_{HEAVY(j)}/(I_{LIGHT(j)} + I_{HEAVY(j)})$ or can be set constant = 1
$\omega_i$ = Max(MS/MS ion search score of light/heavy peptide pairs greater defined confidence threshold)
$I_{LIGHT(j)}$ = integrated isotopic cluster area of light peptide pair j
$I_{HEAVY(j)}$ = integrated isotopic cluster area of heavy peptide pair j
$\eta$ = normalization factor (e.g. median of all $I_{HEAVY}/I_{LIGHT}$ putative peptide ratios)
The contribution of a mass to the normalized ratio $x_{Peptide(j)}$ can be excluded from the calculation if the mass falls within a certain mass window of other peptides. This can remove potential interferences from overlapping peptide peaks from the final average results.

In various embodiments, the Peak Picker software tool can be used as follows. The ICAT reagent expression values can be calculated by taking the intensity weighted average of HL ratios from adjacent spots in which the HL pair is apparent using, for example, equations 2 and 2.1 of Table 1 where the $I_{HEAVY}$ represents the intensity of the heavy isotope mass and $I_{LIGHT}$ is the intensity of the light isotope mass of the HL pair. In various embodiments, the program searches the peak list for all combinations of HL pairs, that is, 9 amu HL pairs for peptides containing 1 cysteine (cys), 18 amu pairs for peptides containing 2 cys, etc. Systematic bias affecting the expression levels in a study that can be due to unequal amounts of starting material or sample handling errors can be corrected by normalization with the median expression ratio η. A symmetrically centered expression distribution of normalized pairs can be generated by taking the logarithm of the ratios using for example, equation 2.1 of Table 1. In various embodiments of expression based analysis only those mass signals that pass an expression threshold (e.g. 2 fold or greater change, expression ratio greater than 2 σ from mean or median) are considered as precursors. In addition, non-differentially expressed pairs or/and singleton peaks that meet one or more signal-to-noise, minimum peak area, mass range, exclusion and adduct filtering criteria can be included for further MS/MS or MS$^n$ analysis. For example, the most intense of the ICAT reagent HL pairs only, always the light or heavy one can be chosen as precursors for further MS/MS or MS$^n$ analysis.

In various embodiments, the Peak Picker software tool generates a list of precursor masses to be submitted for fragmentation, and determines a MALDI plate well spot from which to obtain a fragmentation spectrum (e.g., by MS/MS or MS$^n$ analysis) for each precursor mass. In various embodiments, to accomplish this, for each mass, it first dynamically generates a μLC elution profile by looking for peak masses within a specified tolerance window in successively deposited MALDI spots. For example, if the determined elution profile for a peptide is one minute and the fraction collector spots every 20 seconds, then the number of mass spectra in the considered retention time window is 3. A gap can also be defined that specifies the minimum number of consecutive spots that are allowed to lack the mass in question. Precursors can then be selected and prioritized, for example by the maximum cluster intensity within each elution profile. If the number of precursors per spot is restricted to, for example, four, then the method can use the algorithm to determine recursively the next most intense peak, considering simultaneously all previously selected precursors, until all precursors are evenly distributed across the plate with maximized intensities under the given constraint. In various embodiments, separate optimized acquisition and processing methods for the MS/MS analysis can be generated depending on the analysis goal; for example, on whether the goal is to identify all peptides, non-differentially expressed peptides only, or singletons.

Referring again to FIG. 4, fragmentation spectra of one or more of the selected precursor mass-to-charge ratio ranges are acquired 412 by MS/MS analysis using the MALDI tandem TOF in tandem MS mode 413. The quantitation information (i.e., the relative abundances of HL labeled peptide pairs) can be passed along with the MS/MS jobs that are submitted to the MALDI tandem TOF, where the MS/MS data can be acquired and processed. Special combinations of acquisition parameters can be used for differentially and non-differentially expressed components, and for singletons, which can represent peptides nonspecifically retained by the affinity selection step. In various embodiments, the MS/MS peak lists are extracted, ICAT reagent specific masses are removed and filtered peak lists are deposited into a Mascot generic file and proteins compared to a MS/MS ion and sequence database to assign potential protein and peptide identities 414 using, respectively, the Peak Extraction Program and a Mascot search engine 415. The quantitation information can be stored in comment lines at this time.

In various embodiments, at least a portion of the information obtained from the analysis of the sample containing biomolecules is associated with information in a relational database 416, such as for example, by parsing the Mascot results into an Oracle database using the Parser software tool 417. In various embodiments, the Parser software tool extracts qualitative (peptide and protein identities) and quantitative results from the comment lines from the Mascot search result file and puts them into a relational database.

In various embodiments, the quantitation information (i.e., the relative abundances of HL labeled peptide pairs) can be compared to the potential protein and peptide identities 418 to evaluate whether there are discrepancies with the search results using, for example, the QuantFixer software tool 419. In various embodiments, the QuantFixer software tool 419 can be used to correct quantitation information when there are discrepancies between the quatitation information and the search results that assign potential protein and peptide identities 414.

In various embodiments, quantitation can be performed at the MS level using, for example, the Peak Picker software tool. For example, more than one choice for an isotope partner peak can be possible in complex spectra. There can be a chance that the masses which constitute a HL pair have been incorrectly identified, due to, for example, low intensity, adduct ions and/or multiple overlapping peptide signals. In various embodiments, quantitation information that is collected at MS analysis stage can be putative in nature. In various embodiments, the QuantFixer software tool is used to record the number of tentative ICAT modifications on each peptide as well as whether the peak selected for MS/MS analysis appears to be heavy or light. After the peptides are assigned potential identities, both conclusions are reevaluated using, for example, the Quant-Fixer software tool. In various embodiments, when a putative HL pair assignment disagrees with the information provided by the peptide identification, the QuantFixer software tool is used extract the correct peak area information and corrects the expression level ratios. A corrected expression level ratio can be annotated in the database, indicating uncertainty about the true ratio, because of, for example, a possible second overlapping ICAT pair, which remains unidentified.

In various embodiments, the QuantFixer software tool is used to calculate for each protein the expression values by taking a search result score weighted average of each associated peptide using, for example, the equations of Table 1, which can be used for calculation and normalization of the averaged ratio, standard deviations and confidence intervals at the protein and peptide level.

In various embodiments, comparison of at least a portion of one or more of the one or more mass spectra generated by the MS analysis to known or predicted mass spectra can be used to provide search result dependent data for search result based analysis of mass spectra. For example, a peptide mass fingerprinting (PMF) technique can be used to provide putative identifications of biomolecules in sample.

Figure 5:
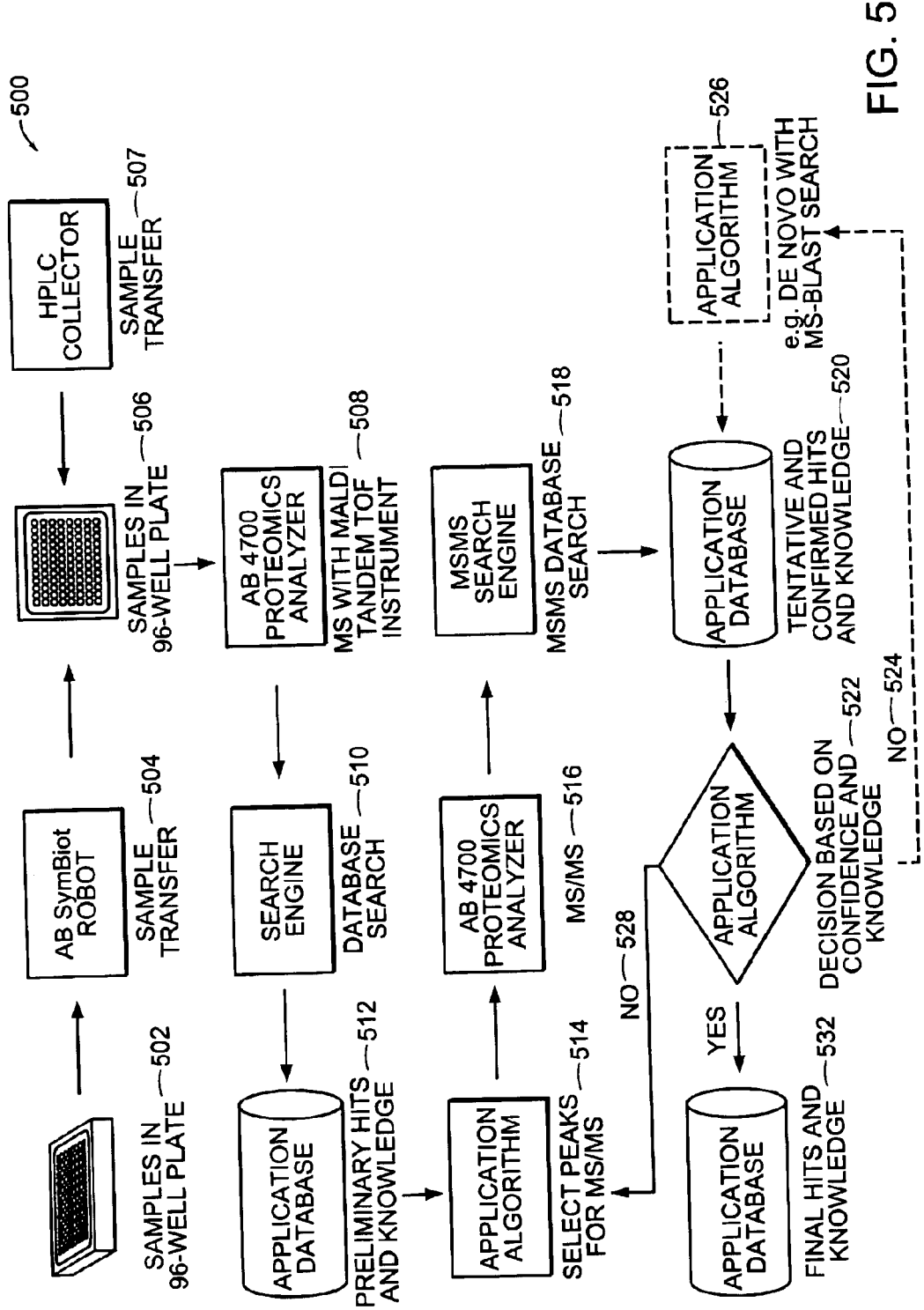
FIG. 5 is a flow diagram illustrating various embodiments utilizing a search results dependent workflow.

Referring to FIG. 5, a flow diagram 500 of various embodiments of methods for analysis of a sample containing biomolecules using a search result data dependent workflow are shown. Various embodiments of the various software tools discussed in the context of FIG. 4 can also be used. Peak Picker, Peak Extraction, Parser and QuantFixer are software tools that can be used to quantify and organize the peptides and proteins identified by the Mascot sequence searching program, and link and store MS, MS/MS, quantitation and identification-related information in a relational database or an object oriented database.

Sample portions for analysis by MS can be provided in any number of ways. In various embodiments, discrete samples are deposited in a multiwell plate 502 such as, e.g., a 96 well plate, in any manner known in the art (e.g., LC based workflows, 2D Gel based workflows). In various embodiments, a robotic sample transfer apparatus such as a Symbiot® robotic workstation (Applied Biosystems, Foster City, Calif.) can be utilized to transfer the samples 504 to and spot a MALDI plate 506 which can be positioned within a mass spectrometric system. In various embodiments, a fraction collector such as a Probot™ can be connected to an HPLC system and spot HPLC fractions directly 507 onto the MALDI plate 506.

One or more mass spectra are then acquired of one or more sample portions of one or more samples 508 using, for example an Applied Biosystems 4700 Proteomics Analyzer. One or more generated mass spectra, which can represent a spectrum of peptide mass peaks, are compared with known or theoretical mass spectra 510 to provide a putative identification for one or more biomolecules in the sample portion.

In various embodiments, comparison can be made by database searching using techniques such as, for example, peptide mass fingerprinting (PMF) techniques. Several searchable data bases are known in the art such as Protein Prospector™ (U. California San Francisco) or Mascot® (Matrix Sciences Ltd.) Various suitable PMF techniques are described in copending U.S. patent application Ser. No., 09/745,920, commonly assigned as the present application and whose disclosure is hereby incorporated in its entirety.

Referring again to FIG. 5, based upon the comparison 510, a preliminary list of mass signals with putative identifications can be generated 512. Mass-to-charge ratio ranges corresponding to one or more mass peaks (precursors) are selected for the further analysis by MS/MS or MS$^n$ based on the search results 514. In various embodiments, m/z ranges are selected which correspond to mass signal meeting one or more of the following criteria: (1) identified with a high level of confidence; (2) identified with a low level of confidence; (3) identified with two or more biomolecules with similar levels of confidence; (4) identified with one or more biomolecules of interest; and (5) not identified or matched with a biomolecule.

Referring again to FIG. 5, fragmentation spectra of one or more of the selected precursor m/z ranges are acquired 516. In various embodiments, MS/MS peak lists are generated from one or more fragmentation spectra and compared to a MS/MS ion and sequence database 518 to assign biomolecule identities to one or more mass signals 520. This information can be utilized to generate an improved list of proteins or peptides which are of interest in identifying or characterizing biomolecules of interest in the sample. In various embodiments assignments of biomolecule identifications for one or more mass signals may not be provided, uncertain or a higher confidence level may be desired. For example, the identification which is uncertain, not provided, or for which a higher confidence level is desired can be of the mass signal itself or of a source biomolecule. For example, where the mass signal is a peptide the identification which is uncertain, not provided or for which a higher confidence level is desired can be of the peptide itself of a parent protein of the peptide.

In various embodiments, if an identification of one or more mass signals is uncertain (e.g. matched to more than one biomolecules), not provided, or a higher confidence level is desired, ("NO" to Decision 522) one or more mass signals from one or more fragmentation spectra can be submitted to a sequence determiner 524, 526, (e.g., a de novo sequence determination algorithm followed by a MS-BLAST search to identify similar peptide and/or protein sequences). This sequence determiner approach 526 might be crucial in studies of incompletely characterized genomes where suitable reference protein sequence databases are not available. In various embodiments, if an identification of one or more mass signals is uncertain, not provided or a higher confidence level is desired, ("NO" to Decision 522) or one or more precursor m/z ranges are selected for further analysis by MS/MS or $MS^n$ 528. The process of additional searching and/or MS/MS analysis can be repeated. In various embodiments, if an identification of a mass signal is sufficiently certain, ("YES" to Decision 522) the mass signal with identification can be stored in a final list 532.

In various embodiments, the information obtained from the analysis of the sample containing biomolecules using one or more or of an expression based analysis, mass spectrometric based analysis, and search result based analysis, can be used to characterize one or more biomolecules, or combinations of biomolecules, in the sample by associating at least a portion of this information with a relational database or object oriented database. For example, based on the association with information in the relational database or object oriented database, one or more biomolecules, or combinations of biomolecules, could be characterized as, for example, a drug target, a toxic response and/or a biomarker for, e.g., screening a risk factor, diagnosis, and/or prognosis.

Figure 6:
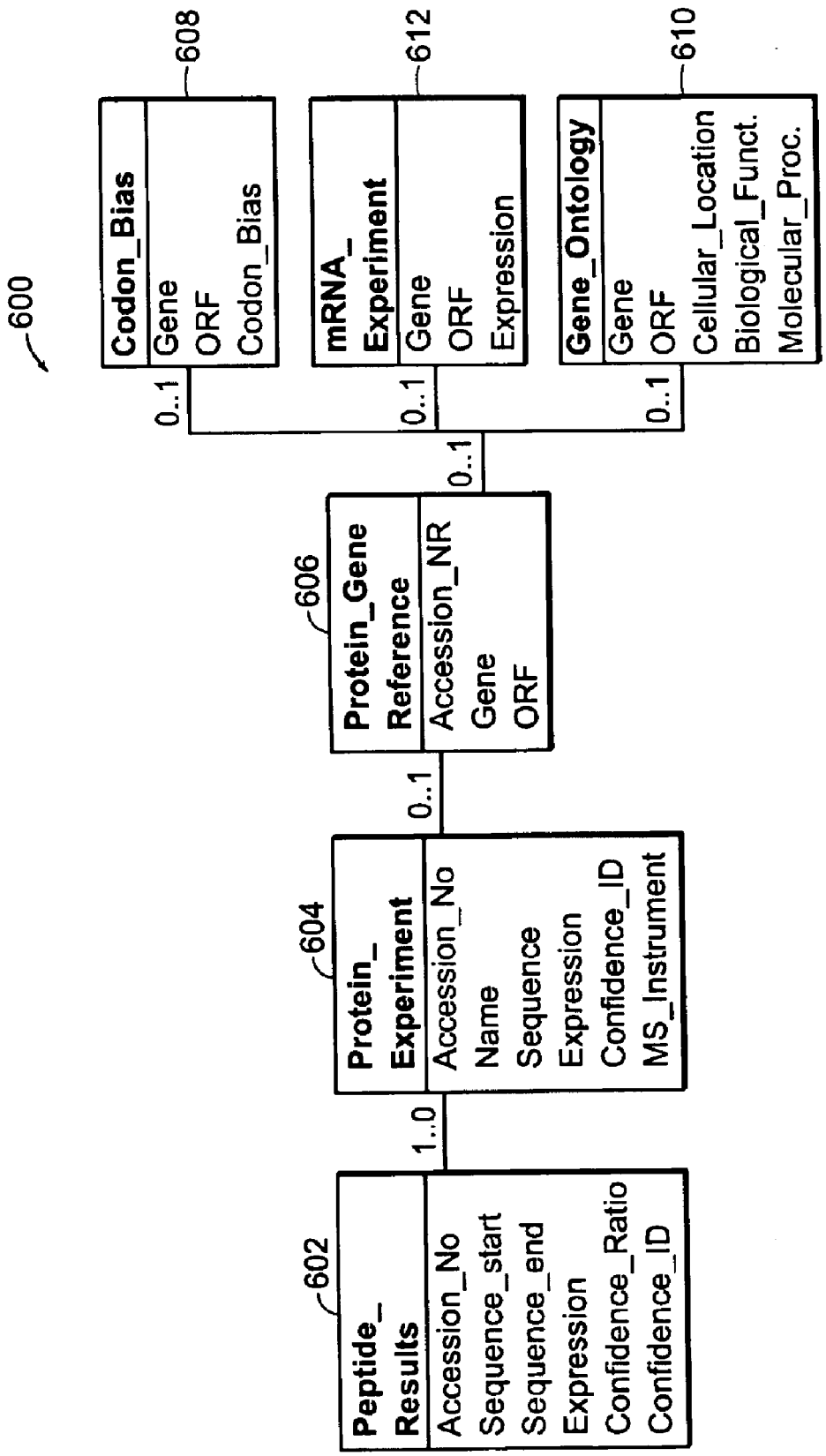
FIG. 6 is a block diagram of various embodiments of a relational database.

Referring to FIG. 6, in various embodiments the underlying MS, MS/MS, protein and mRNA related experimental results can be deposited into a relational database 600. Peptide results 602 can be linked to protein results 604. Protein results 604 can be linked through reference lists 606 with corresponding genes and open reading frames (ORFs), and associated to codon bias 608, gene ontology information 610, such as biological process, molecular function and subcellular location (available at MIPS: http://mips.gsf.de/ or SGD: http://genome-www.stanford.edu/Saccharomyces/), and mRNA data 612. The mRNA and protein ratios can made comparable by rescaling, e.g., dividing by the median of the respective ratios. FIG. 7 depicts various relationships 700 that can be used, for example, with FIG. 6.

A wide variety of mass spectrometers and mass spectrometer systems can be used to acquire mass spectra and fragmentation spectra suitable for use with the methods and articles of manufacture described herein. Suitable mass spectrometer systems for MS/MS or $MS^n$ include an ion fragmentor and two or more mass spectrometers. Suitable mass spectrometers for MS, MS/MS or $MS^n$, include, but are not limited to, time-of-flight (TOF) mass spectrometers, quadrupole mass spectrometers (QMS), and ion mobility spectrometers (IMS). Examples of suitable ion fragmentors include, but are not limited to, collision cells (in which ions are fragmented by causing them to collide with neutral gas molecules), photodissociation cells (in which ions are fragmented by irradiating them with a beam of photons), and surface dissociation fragmentors (in which ions are fragmented by colliding them with a solid or a liquid surface). Suitable mass spectrometer systems can also include ion reflectors.

Examples of suitable time-of-flight mass spectrometer systems and methods for obtaining mass spectra and fragmentation spectra are described, for example, in U.S. Pat. No. 6,348,688, filed Jan. 19, 1999, and issued Feb. 19, 2002; U.S. application Ser. No. 10/023,203 filed Dec. 17, 2001; U.S. application Ser. No. 10/198,371 filed Jul. 18, 2002; and U.S. application Ser. No. 10/327,971 filed Dec. 20, 2002; the entire contents of all of which are herein incorporated by reference. In various embodiments, delayed extraction is performed to provide time-lag focusing to correct for the initial sample ion velocity distribution of ions generated by MALDI, for example, as described in U.S. Pat. No. 5,625,184 filed May 19, 1995, and issued Apr. 29, 1997; U.S. Pat. No. 5,627,369, filed Jun. 7, 1995, and issued May 6, 1997; U.S. Pat. No. 6,002,127 filed Apr. 10, 1998, and issued Dec. 14, 1999; U.S. Pat. No. 6,541,765 filed May 29, 1998, and issued Apr. 1, 2003; U.S. Pat. No. 6,057,543, filed Jul. 13, 1999, and issued May 2, 2000; and U.S. Pat. No. 6,281,493 filed Mar. 16, 2000, and issued Aug. 28, 2001; and U.S. application Ser. No. 10/308,889 filed Dec. 3, 2002; the entire contents of all of which are herein incorporated by reference.

In various embodiments, the mass spectrometer system comprises a triple quadrupole mass spectrometer for selecting a primary ion and/or detecting and analyzing fragment ions thereof. In various embodiments, the first quadrupole selects the primary ion. The second quadrupole is maintained at a sufficiently high pressure and voltage so that multiple low energy collisions occur causing some of the ions to fragment. The third quadrupole is scanned to analyze the fragment ion spectrum.

In various embodiments, the mass spectrometer system comprises two quadrupole mass filters and a TOF mass spectrometer for selecting a primary ion and/or detecting and analyzing fragment ions thereof. In various embodiments, the first quadrupole selects the primary ion. The second quadrupole is maintained at a sufficiently high pressure and voltage so that multiple low energy collisions occur causing some of the ions to fragment, and the TOF mass spectrometer detects and analyzes the fragment ion spectrum.

In various embodiments, the mass spectrometer system comprises two TOF mass analyzers and an ion fragmentor (such as, for example, CID or SID). In various embodiments, the first TOF selects the primary ion for introduction in the ion fragmentor and the second TOF mass spectrometer detects and analyzes the fragment ion spectrum. The TOF analyzers can be linear or reflecting analyzers.

In various embodiments, the mass spectrometer system comprises a time-of-flight mass spectrometer and an ion reflector. The ion reflector is positioned at the end of a field-free drift region of the TOF and is used to compensate for the effects of the initial kinetic energy distribution by modifying the flight path of the ions. In various embodiments ion reflector consists of a series of rings biased with potentials that increase to a level slightly greater than an accelerating voltage. In operation, as the ions penetrate the reflector they are decelerated until their velocity in the direction of the field becomes zero. At the zero velocity point, the ions reverse direction and are accelerated back through the reflector. The ions exit the reflector with energies identical to their incoming energy but with velocities in the opposite direction. Ions with larger energies penetrate the reflector more deeply and consequently will remain in the reflector for a longer time. The potentials used in the reflector are selected to modify the flight paths of the ions such that ions of like mass and charge arrive at a detector at substantially the same time.

In various embodiments, the mass spectrometer system comprises a tandem MS—MS instrument comprising a first field-free drift region having a timed ion selector to select a primary sample ion of interest, a fragmentation chamber (or ion fragmentor) to produce sample ion fragments, a mass analyzer to analyze the fragment ions. In various embodiments, the timed ion selector comprises a pulsed ion deflector. In various embodiments, the second ion deflector can be used as a pulsed ion deflector in versions of this tandem MS/MS instrument. In various embodiments of operation, the pulsed ion deflector allows only those ions within a selected mass-to-charge ratio range to be transmitted to the ion fragmentation chamber. In various embodiments, the mass analyzer is a time-of-flight mass spectrometer. The mass analyzer can include an ion reflector. In various embodiments, the fragmentation chamber is a collision cell designed to cause fragmentation of ions and to delay extraction. In various embodiments, the fragmentation chamber can also serve as a delayed extraction ion source for the analysis of the fragment ions by time-of-flight mass spectrometry.

In various embodiments, the mass spectrometer system comprises a tandem TOF-MS having a first, a second, and a third TOF mass separator positioned along a path of the plurality of ions generated by the pulsed ion source. The first mass separator is positioned to receive the plurality of ions generated by the pulsed ion source. The first mass separator accelerates the plurality of ions generated by the pulsed ion source, separates the plurality of ions according to their mass-to-charge ratio, and selects a first group of ions based on their mass-to-charge ratio from the plurality of ions. The first mass separator also fragments at least a portion of the first group of ions. The second mass separator is positioned to receive the first group of ions and fragments thereof generated by the first mass separator. The second mass separator accelerates the first group of ions and fragments thereof, separates the first group of ions and fragments thereof according to their mass-to-charge ratio, and selects from the first group of ions and fragments thereof a second group of ions based on their mass-to-charge ratio. The second mass separator also fragments at least a portion of the second group of ions. The first and/or the second mass separator may also include an ion guide, an ion-focusing element, and/or an ion-steering element. In various embodiments, the second TOF mass separator decelerates the first group of ions and fragments thereof. In various embodiments, the second TOF mass separator includes a field-free region and an ion selector that selects ions having a mass-to-charge ratio that is substantially within a second predetermined range. In various embodiments, at least one of the first and the second TOF mass separator includes a timed-ion-selector that selects fragmented ions. In various embodiments, at least one of the first and the second mass separators includes an ion fragmentor. The third mass separator is positioned to receive the second group of ions and fragments thereof generated by the second mass separator. The third mass separator accelerates the second group of ions and fragments thereof and separates the second group of ions and fragments thereof according to their mass-to-charge ratio. In various embodiments, the third mass separator accelerates the second group of ions and fragments thereof using pulsed acceleration. In various embodiments, an ion detector positioned to receive the second group of ions and fragments thereof. In various embodiments, an ion reflector is positioned in a field-free region to correct the energy of at least one of the first or second group of ions and fragments thereof before they reach the ion detector.

In various embodiments, the mass spectrometer system comprises a TOF mass analyzer having multiple flight paths, multiple modes of operation that can be performed simultaneously in time, or both. This TOF mass analyzer includes a path selecting ion deflector that directs ions selected from a packet of sample ions entering the mass analyzer along either a first ion path, a second ion path, or a third ion path. In some embodiments, even more ion paths may be employed. In various embodiments, the second ion deflector can be used as a path selecting ion deflector. A time-dependent voltage is applied to the path selecting ion deflector to select among the available ion paths and to allow ions having a mass-to-charge ratio within a predetermined mass-to-charge ratio range to propagate along a selected ion path.

For example, in various embodiments of operation of a TOF mass analyzer having multiple flight paths, a first predetermined voltage is applied to the path selecting ion deflector for a first predetermined time interval that corresponds to a first predetermined mass-to-charge ratio range, thereby causing ions within first mass-to-charge ratio range to propagate along the first ion path. In various embodiments, this first predetermined voltage is zero allowing the ions to continue to propagate along the initial path. A second predetermined voltage is applied to the path selecting ion deflector for a second predetermined time range corresponding to a second predetermined mass-to-charge ratio range thereby causing ions within the second mass-to-charge ratio range to propagate along the second ion path. Additional time ranges and voltages including a third, fourth etc. can be employed to accommodate as many ion paths as are required for a particular measurement. The amplitude and polarity of the first predetermined voltage is chosen to deflect ions into the first ion path, and the amplitude and polarity of the second predetermined voltage is chosen to deflect ions into the second ion path. The first time interval is chosen to correspond to the time during which ions within the first predetermined mass-to-charge ratio range are propagating through the path selecting ion deflector and the second time interval is chosen to correspond to the time during which ions within the second predetermined mass-to-charge ratio range are propagating through the path selecting ion deflector. A first TOF mass separator is positioned to receive the packet of ions within the first mass-to-charge ratio range propagating along the first ion path. The first TOF mass separator separates ions within the first mass-to-charge ratio range according to their masses. A first detector is positioned to receive the first group of ions that are propagating along the first ion path. A second TOF mass separator is positioned to receive the portion of the packet of ions propagating along the second ion path. The second TOF mass separator separates ions within the second mass-to-charge ratio range according to their masses. A second detector is positioned to receive the second group of ions that are propagating along the second ion path. In some embodiments, additional mass separators and detectors including a third, fourth, etc. may be positioned to receive ions directed along the corresponding path. In one embodiment, a third ion path is employed that discards ions within the third predetermined mass range. The first and second mass separators can be any type of mass separator. For example, at least one of the first and the second mass separator can include a field-free drift region, an ion accelerator, an ion fragmentor, or a timed ion selector. The first and second mass separators can also include multiple mass separation devices. In various embodiments, an ion reflector is included and positioned to receive the first group of ions, whereby the ion reflector improves the resolving power of the TOF mass analyzer for the first group of ions. In various embodiments, an ion reflector is included and positioned to receive the second group of ions, whereby the ion reflector improves the resolving power of the TOF mass analyzer for the second group of ions.

Figure 8:
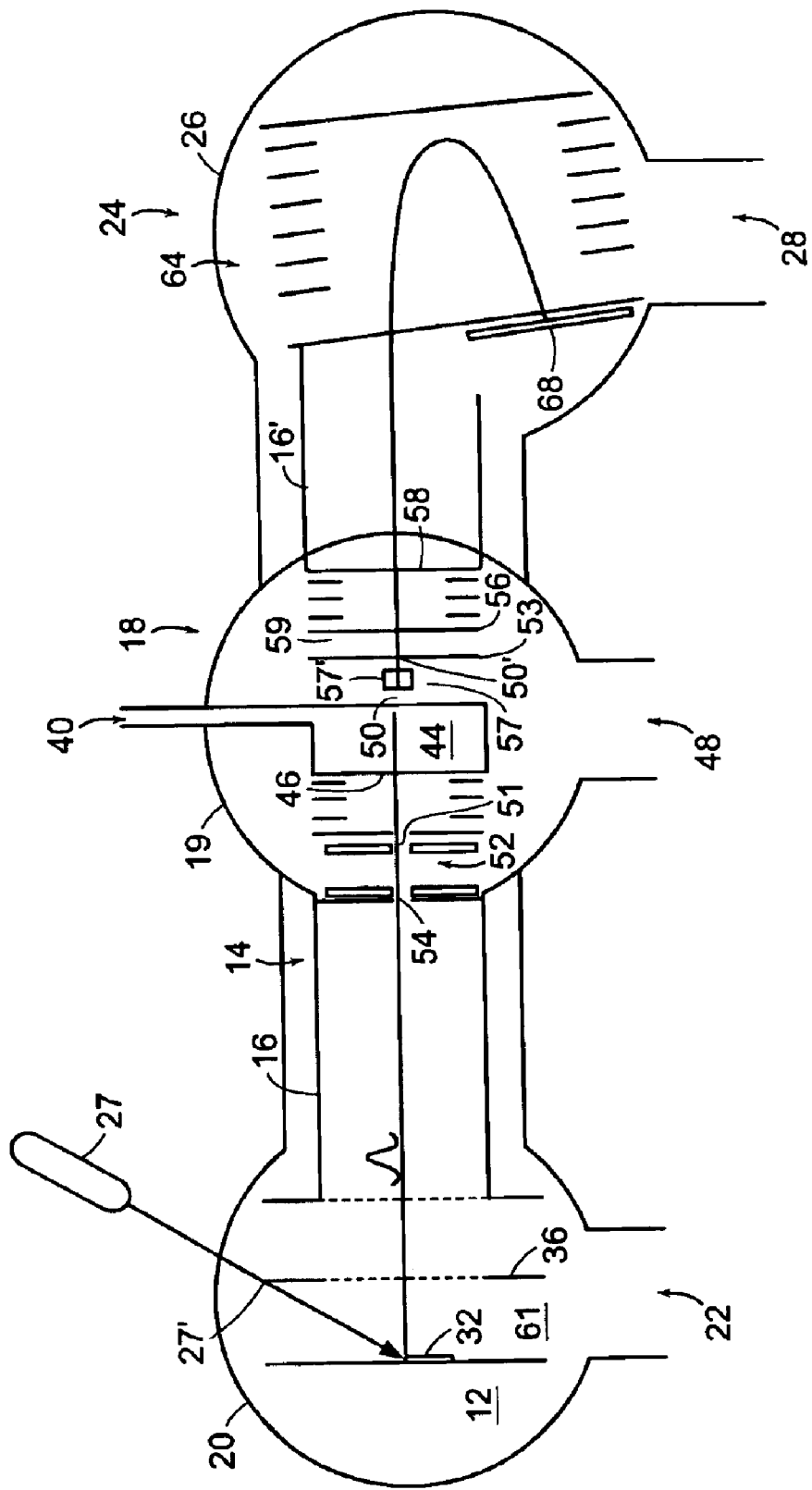
FIG. 8 is a schematic diagram of one embodiment of a TOF mass spectroscopy apparatus.

Referring to FIG. 8, in various embodiments, a tandem time-of-flight mass spectrometer system 10 using delayed extraction includes a pulsed ion generator 12. The pulsed ion generator 12 includes a laser 27 and a source extraction grid 36. A timed ion selector 14 can be in communication with the ion generator 12. The ion selector 14 comprises a field-free drift tube 16 and a pulsed ion deflector 52. The field-free drift tube 16 can include an ion guide.

An ion fragmentation chamber 18, can be in communication with ion selector 14. The ion fragmentation chamber shown in FIG. 4 includes a collision cell 44. However, the fragmentation chamber 18 can be any other type of fragmentation chamber known in the art such as a photodissociation chamber or a surface induced dissociation chamber. A small aperture 54 at the entrance to the pulsed ion deflector 52 allows free passage of the ion beam to the fragmentation chamber 18, but limits the flow of neutral gas. The fragmentation chamber 18 allows free passage of the ion beam, but limits the flow of neutral gas.

In one embodiment, a grid plate 53 can be positioned adjacent the collision cell 44 and biased to form a field free region 57. The field free region 57 can include an ion guide 57'. A fragmentor extraction grid 56 can be positioned adjacent the grid plate 53 to an entrance 58 to the analyzer 24. In another embodiment, fragmentor extraction grid 56 can be positioned directly adjacent to the exit aperture, eliminating the grid plate 53. This embodiment can be used for measurements are the fragmentation can be substantially completed in the collision cell 44. The analyzer 24 includes a second field-free drift tube 16' in communication with an ion mirror 64. The second-free drift tube 16' can include an ion guide. A detector 68 can be positioned to receive the reflected ions.

The pulsed ion generator 12 and drift tube 16 are enclosed in a vacuum housing 20, which can be connected to a vacuum pump (not shown) through a gas outlet 22. Also, the fragmentation chamber 18 and pulsed ion deflector 52 are enclosed in vacuum housing 19, which can be connected to a vacuum pump (not shown) through a gas outlet 48. Similarly, the analyzer 24 can be enclosed in a vacuum pump (not shown) through a gas outlet 28. Similarly, the analyzer 24 can be enclosed in a vacuum housing 26, which can be connected to a vacuum pump (not shown) through a gas outlet 28. The vacuum pump maintains the background pressure of neutral gas in the vacuum housing 20, 19 and 26 sufficiently low that collisions of ions with neutral gas in the vacuum housing 20, 19 and 26 sufficiently low that collisions of ions with neutral molecules are unlikely to occur.

In operation, a sample 32 to be analyzed can be ionized by the pulsed ion generator 12, which produces a pulse of ions. In one embodiment, the pulsed ion generator 12 employs MALDI. In this embodiment, a laser beam 27' impinges upon a sample plate having the sample 32 which has been mixed with a matrix capable of selectively absorbing the wavelength of the incident laser beam 28.

At a predetermined time after ionization, the ions are accelerated by applying an ejection potential between the sample 32 and the source extraction grid 36 and between the source extraction grid 36 and the drift tube 16. In one embodiment, the drift tube can be at ground potential. After this acceleration, the ions travel through the drift tube with velocities which are nearly proportional to the square root of their charge-to-mass ration; that is, heavier ion travel more slowly. Thus, within the drift tube 16, the ions separate according to their mass-to-charge ration with ions of higher mass traveling more slowly than those of lower mass.

The pulsed ion deflector 52 opens for a time window at a predetermined time after ionization. This permits only those ions with the selected mass-to-charge ratios, arriving at the pulsed ion deflector 52 within the predetermined time window during which the pulsed ion deflector 52 is permitting access to the collision cell 44, to be transmitted. Hence, only predetermined ions, those having the selected mass-to-charge ration, will be permitted to enter the collision cell 44 by the pulsed ion deflector 52. Other ions of higher or lower mass are rejected.

The selected ions entering the collision cell 44 collide with the neutral gas entering through inlet 40. The collisions cause the ions to fragment. The energy of the collisions is proportional to a difference in potential between the applied to the sample 32 and the collision cell 44. In one embodiment, the pressure of the neutral gas in the collision cell 44 is maintained at about 3–10 torr and the pressure in the space surrounding the collision cell 44 is about 5–10 torr. Gas diffusing from the collision cell 44 through an ion entrance aperture 46 and ion exit aperture 50 can be facilitated by a vacuum pump (not shown) connected to a gas outlet 48. In another embodiment, a high-speed pulsed value (not shown) can be positioned in gas inlet 40 so as to produce a high pressure pulse of neutral gas during the time when ions arrive at the fragmentation chamber 18, and, for the remainder of the time, the fragmentation chamber 18 is maintained as a vacuum. The neutral gas can be any neutral gas such as helium, nitrogen, argon, krypton or xenon.

In one embodiment, the grid plate 53 and the fragmentor extraction grid 56 are biased at substantially the same potential as the collision cell 44 until the fragment ions pass through an aperture 50' in grid plate 53 and enter the nearly field-free region 59 between the grid plate 53 and the extraction grid 56. At a predetermined time after the ions pass grid plate 53, the potential on grid plate 53 is rapidly switched to a high voltage thereby causing the ions to be accelerated. The accelerated ions pass through the entrance 58 to the analyzer 24, into a second field-free drift tube 16', into the ion mirror 64, and to the detector 68, which is positioned to receive the reflected ions.

The time of flight of the ion fragments, starting from the time that the potential on the grid plate 53 is switched and ending with the ion detection by the detector 68, is measured. The mass-to-charge ratio of the ion fragments is determined from the measured time. The mass-to-charge ratio can be determined with very high resolution by properly choosing the operating parameters so that the fragmentation chamber 18 functions as a delayed extraction source of ion fragments. The operating parameters include: (1) the delay between the passing of the fragment ions through the aperture 50' in grid plate 53 and the application of the accelerating potential to the grid plate 53; and (2) the magnitude of the extraction field between the grid plate 53 and the fragmentor extraction grid 56.

In another embodiment, grid 53 is not used or does not exist. This embodiment can be used for measurements where the fragmentation is substantially completed in the collision cell 44. In this embodiment, the fragmentor extraction grid 56 is biased at substantially the same potential as the collision cell 44. At a predetermined time after the ions exit the collision cell 44, the high voltage connection to the collision cell 44 is rapidly switched to a second high voltage supply (not shown) thereby causing the ions to be accelerated. The accelerated ions pass through the entrance 58 to the analyzer 24, into a second field-free drift tube 16', into the ion mirror 64, and to the detector 68, which is positioned to receive the reflected ions.

The time of flight of the ion fragments, starting from the time that the potential on the collision cell 44 is switched and ending with ion detection by the detector 68, is measured. The mass-to-charge ratio of the ion fragments is determined from the measured time. The mass-to-charge ratio can be determined with very high resolution by properly choosing the operating parameters so that the fragmentation chamber 18 functions as a delayed extraction source of ion fragments. The operating parameters include: (1) the predetermined time after the ions exit the collision cell 44 before the high voltage is rapidly switched to the second high voltage; and (2) the magnitude of the extraction field between the collision cell 44 and the fragmentor extraction grid 56.

EXAMPLES

The following examples are illustrative and are not intended to limit the present invention. In Examples 1–4 biological samples were prepared for analysis substantially as follows. Two strains of yeast (*Saccharomyces cerevisiae*) were used in Examples 1–4. The strain we describe herein as "wild-type" has been designated HFY1200 (He and Jacobson, 2001); it has mutations in ade2, his3, leu2, trp1 and can1, which come in to play when the yeast is grown in restricted media. The UPF1 knockout strain has been designated HFY871 (He and Jacobson, 2001). It has the same genetic background as HFY1200, but has the His3 gene inserted in place of the Upf1 gene. Yeast samples (both wild type and Upf1 mutant strains) were grown to mid-log phase (e.g., $OD_{600}$=0.7) in 2 liters of YPD medium at 30° C. in a fermentor and were harvested when the optical density at 600 nm ($OD_{600}$) was between 0.5–0.7. Subsequent procedures were performed at 4° C. Yeast cells were collected by centrifugation at 4,000 g for 5 min and were washed with 200 mL of water and then 200 mL of 50 mM Tris-Cl, pH 7.5 (buffer A). The yeast extracts were prepared using the liquid nitrogen (LN2) grinding method. The cell pellets were re-suspended in 1/10 volume of buffer A and then carefully mixed into LN2 to form beads. The beads were crushed and grinded to fine powder in LN2 using a pre-chilled mortar and pestle. The fine powder was stored at −70° C. The soluble fraction of the yeast extracts was prepared by thawing the fine powder on ice for 15 min and then collecting the supernatant by centrifugation at 14,000 rpm for 5 min using a microcentrifuge. The protein concentration of the soluble fraction was determined using a Bradford assay. Each 2 liter culture yields about 4 g of cell pellet and the estimated yield for each soluble fraction is about 400 mg.

Prepared soluble portions of the samples were labeled with an acid cleavable ICAT™ reagent Where the wild type was labeled with the light isotope and the mutant with the heavy isotope. The reagent featured 13C heavy isotope to facilitate co-migration of the peptide pairs in the HPLC. Two 500 μg aliquots from each strain were resuspended in 6 M Guanidine-HCl, 1% Triton X-100, 50 mM Tris HCl pH 8.5 (Buffer B). The proteins were then reduced by the addition of 10 μl of 50 mM tricarboxyethylphosphine and boiled at 100° C. for 10 min. After cooling for 5 min to room temperature, 1 mg of the ICAT light reagent, dissolved in acetonitrile, was added to the wild type, whereas 1 mg of the ICAT heavy reagent was added to the Upf1 knockout sample. After incubation for 2 h at 37° C., the two aliquots were combined and precipitated with acetone (6:1 volume of acetone:volume of sample). The precipitated proteins were centrifuged for 10 min at 13,000 g, the acetone was decanted, and the pellet was resuspended in 100 μl of acetonitrile. The sample was then diluted with 900 μl of 50 mM Tris pH 8.5, 10 mM CaCl2, 20% acetonitrile. 12 μg of porcine trypsin (Promega) was added, the sample was incubated for 2 h at 37° C., then another 12 μg of porcine trypsin was added, followed by overnight digestion.

In Examples 3 and 4, 1 milligram (mg) of wild type and 1 mg of Upf1 mutant were used; in Examples 1 and 2, 100 micrograms of both the wild type and mutant were used. Labeled wild type and mutant samples were combined and digested with trypsin. In Examples 3 and 4 the digest mixture was then fractionated with strong cation exchange into 20 fractions and the fractions were collected on a Vision™ Biochromatography Workstation, (Applied Biosystems, Inc., Foster City, Calif.); in Examples 1 and 2 the digest mixture was then fractionated with strong cation exchange into 35 fractions.

In examples 1–4 the ion exchange chromatography was performed substantially as follows. The sample (1 mL) was diluted to 10 ml with 10 mM K3PO4, 25% ACN, pH ~2.5 (Buffer C). In two batches, the sample was injected onto a 4.6×100 mm polysulfoethyl A cation exchange column at a flow rate of 1 ml/min. The high salt buffer contained 350 mM KCl, 10 mM K3PO4, 25% ACN, pH ~2.5 (Buffer D). Peptides were separated over four linear gradient segments using an Applied Biosystems Vision Workstation in order to separate the peptides as efficiently as possible: 2 min to 10% Buffer D, 15 min to 20% Buffer D, 3 min to 45% Buffer D, and 10 min to 100% Buffer D. Fractions consisting of 1.5 mL were collected typically beginning 4 min into the gradient. Prior to affinity chromatography, 250 μl of 100 mM Na3PO4 1500 mM NaCl pH 10 was added to each fraction, to bring the pH to ~7.2.

Affinity selection chromatography was performed to select cysteine containing peptides. Cysteine containing peptides were labeled with a biotin affinity group derivatized with a sulfhydryl-specific containing moiety. The labeled cysteine containing peptides were then isolated on an avidin column for purification. Ion exchange fraction was separately purified using the monomeric avidin beads supplied with the ICAT reagent kit (Applied Biosystems), and purified according to instructions. The peptides were then cleaved substantially according to the instructions of the ICAT reagent kit. Each eluate was dried completely using reduced pressure. A 200 μl aliquot of ICAT cleaving reagent from the ICAT reagent kit was added, followed by incubation at 37° C. for 2 h. Once again the sample was dried under reduced pressure until time for reversed phase separation. At that time, each sample was resuspended in 100 μl of 2% acetonitrile, 0.1% TFA.

The peptide mixtures retained on the avidin column were then further separated by microbore HPLC and collected onto the sample plates of an AB 4700 Proteomics Analyzer mass spectrometer system by a Probot™ fraction collector (Dionex Corporation™, Sunnyvale, Calif.). The effluent from capillary RP-HPLC was mixed with matrix and spotted onto a MALDI target plate. In Examples 1, 3 and 4, fractions were collected every 20 seconds, in Example 2 fractions were collected every 5 seconds. In Examples 3 and 4, fractions 4–19 were subjected to reverse phase chromatography (RPC) using 0.1×150 mm 5 micron 200 Angstrom Magic C18 column (Michrom Bioresources, Auburn, Calif.) on an Ultimate™ System (Dionex Corporation™, Sunnyvale, Calif.)

MS and MS/MS were performed by MALDI using a 4700 Proteomics Analyzer (Applied Biosystems, Inc., Foster City, Calif.) equipped with GPS Explorer version 1.0 and by ESI using a QStar® Pulsar I System (Applied Biosystems, Inc., Foster City, Calif.). Pro ICAT (Applied Biosystems, Inc., Foster City, Calif.) software was utilized to initially identify and quantify peptide signals for the ESI experiments and the database used was SwissProt release 36. The Mascot® sequence-searching program (Matrix Science Ltd, London, UK) and the database used was MSDB from the Jun. 1, 2003 release, containing 9722 *Saccharomyces Cerevisiae* sequences was used for MALDI and also for ESI peptide and protein identification in order to provide a basis for data consolidation.

Analysis of transcript expression levels was also performed by mRNA array analysis with a S98 array corresponding to the *S. cerevisiae* yeast genome (Affymetrix, Santa Clara, Calif.).

Example 1

Mass Spectrometric Data Based Precursor Selection

Figure 9:
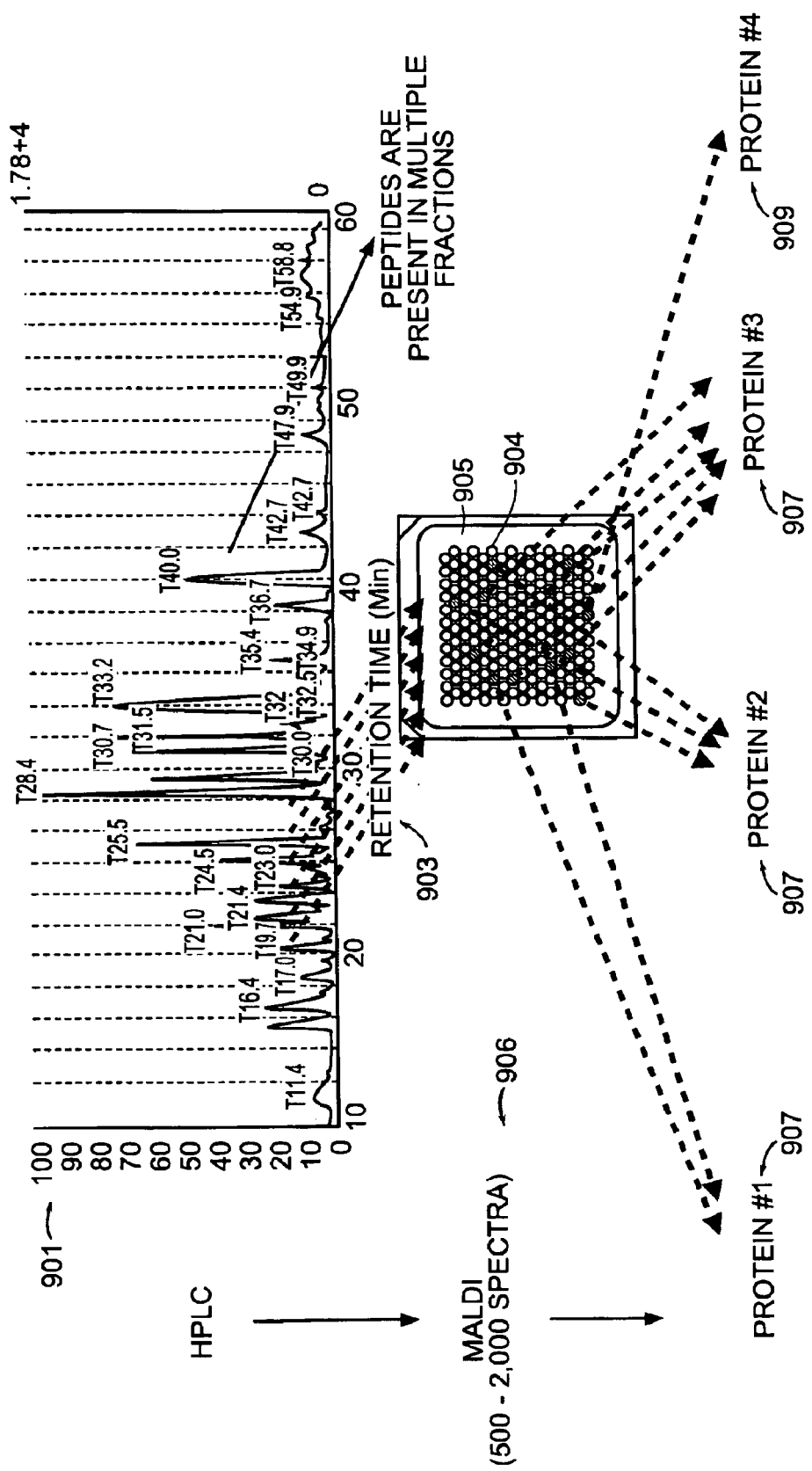
FIG. 9 is a schematic illustration of various embodiments of a retention time dependent precursor selection.
Figure 10A:
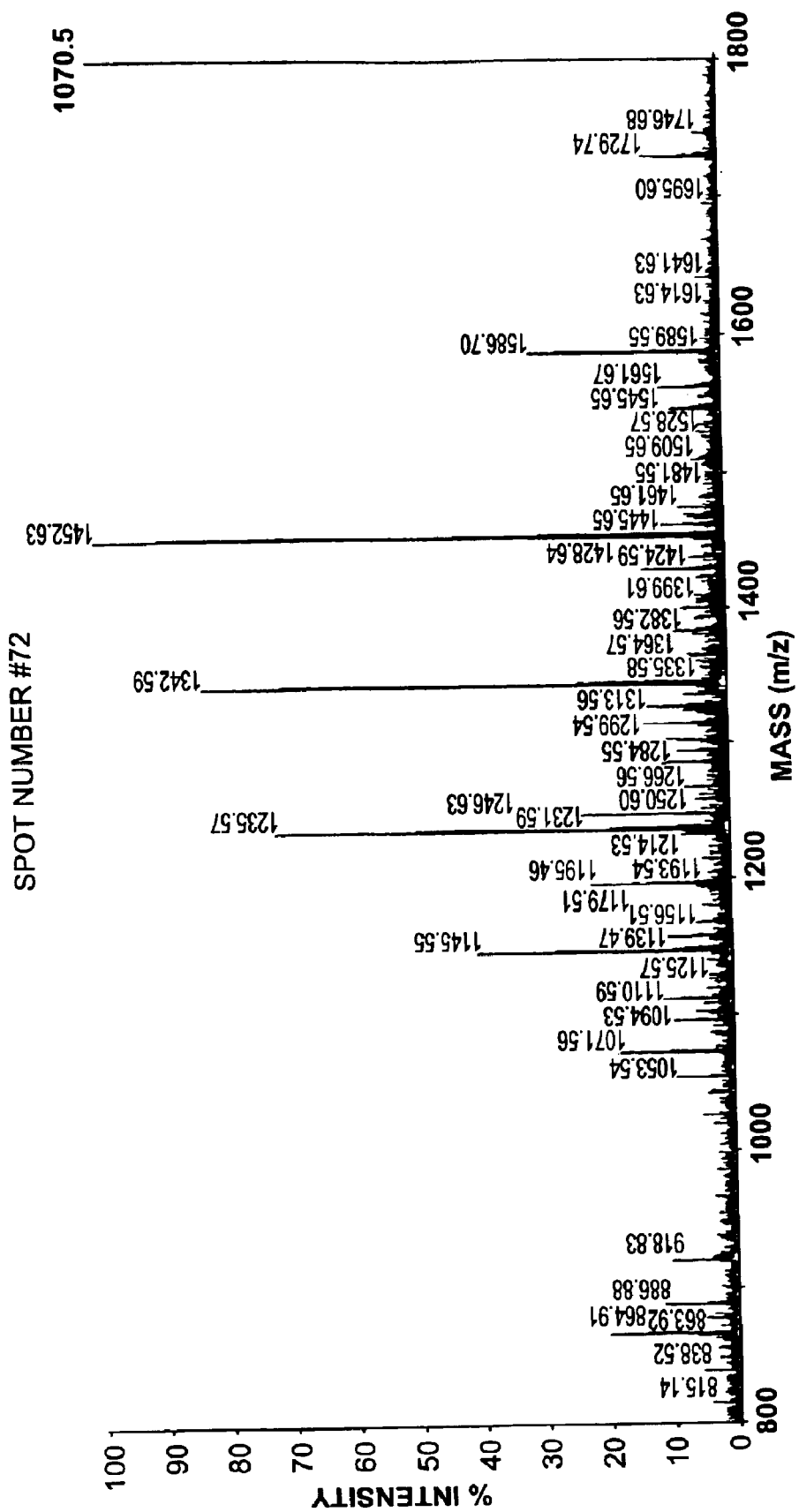
Figure 10B:
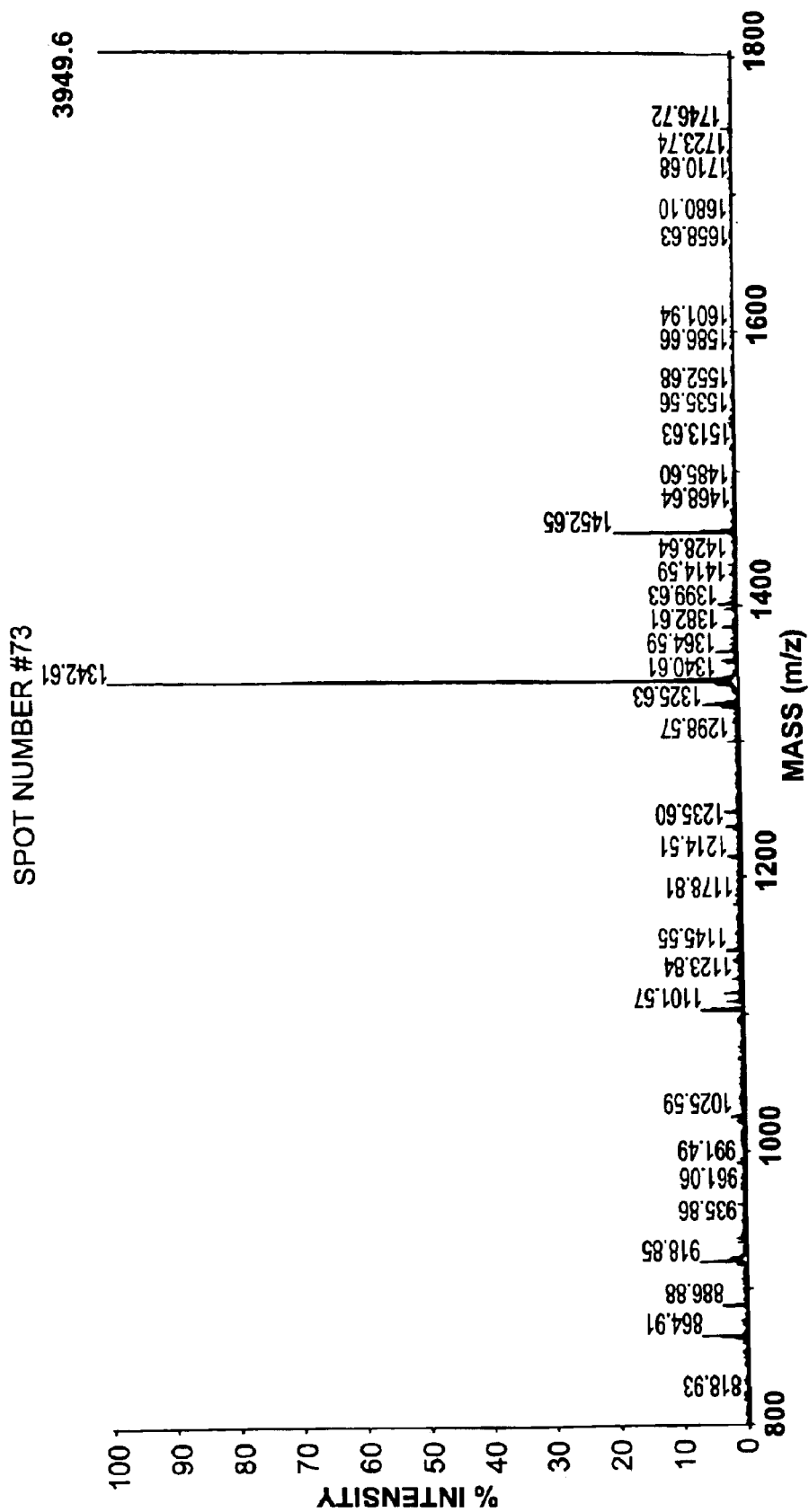
Figure 10C:
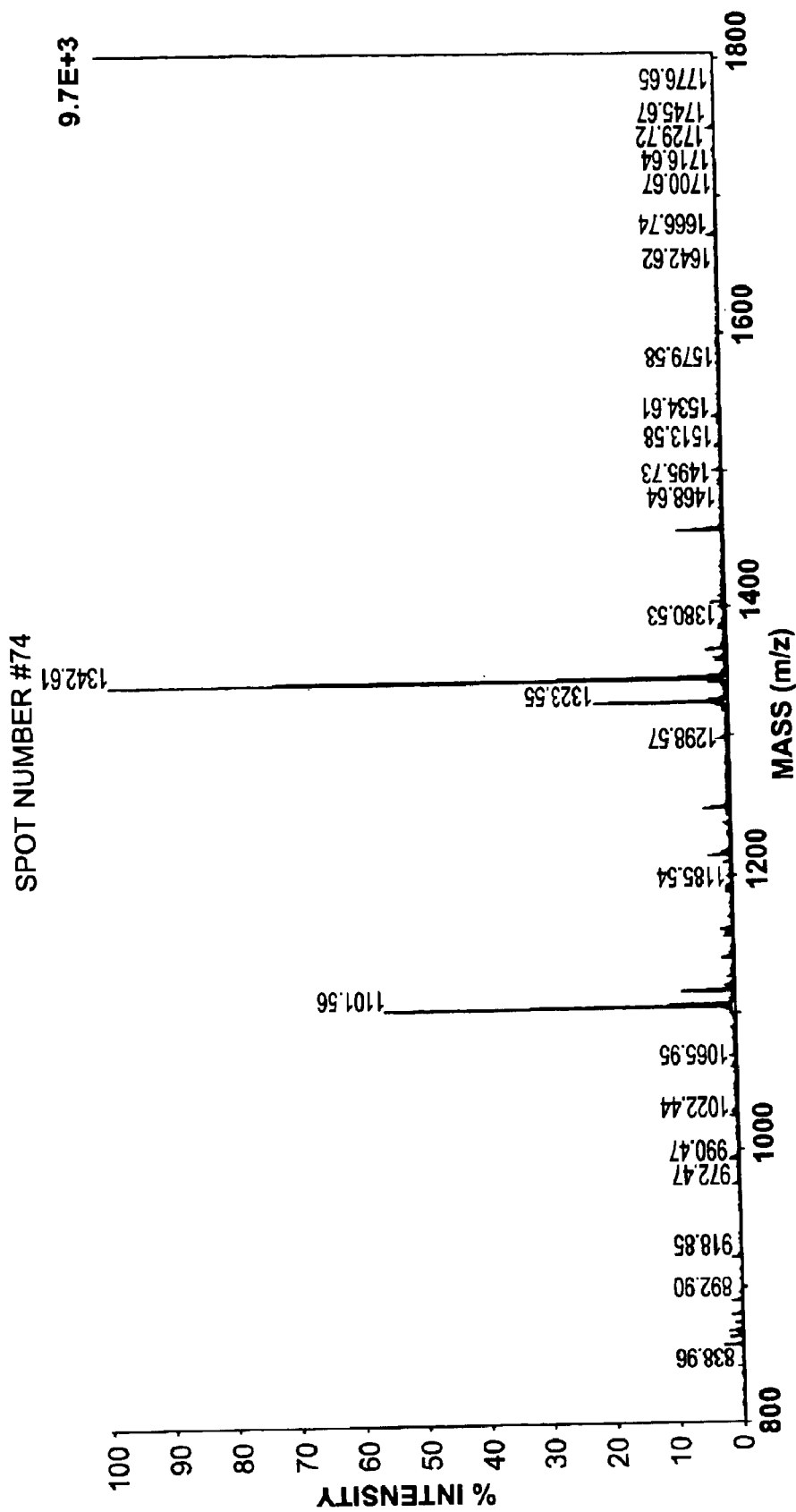
Figure 10E:
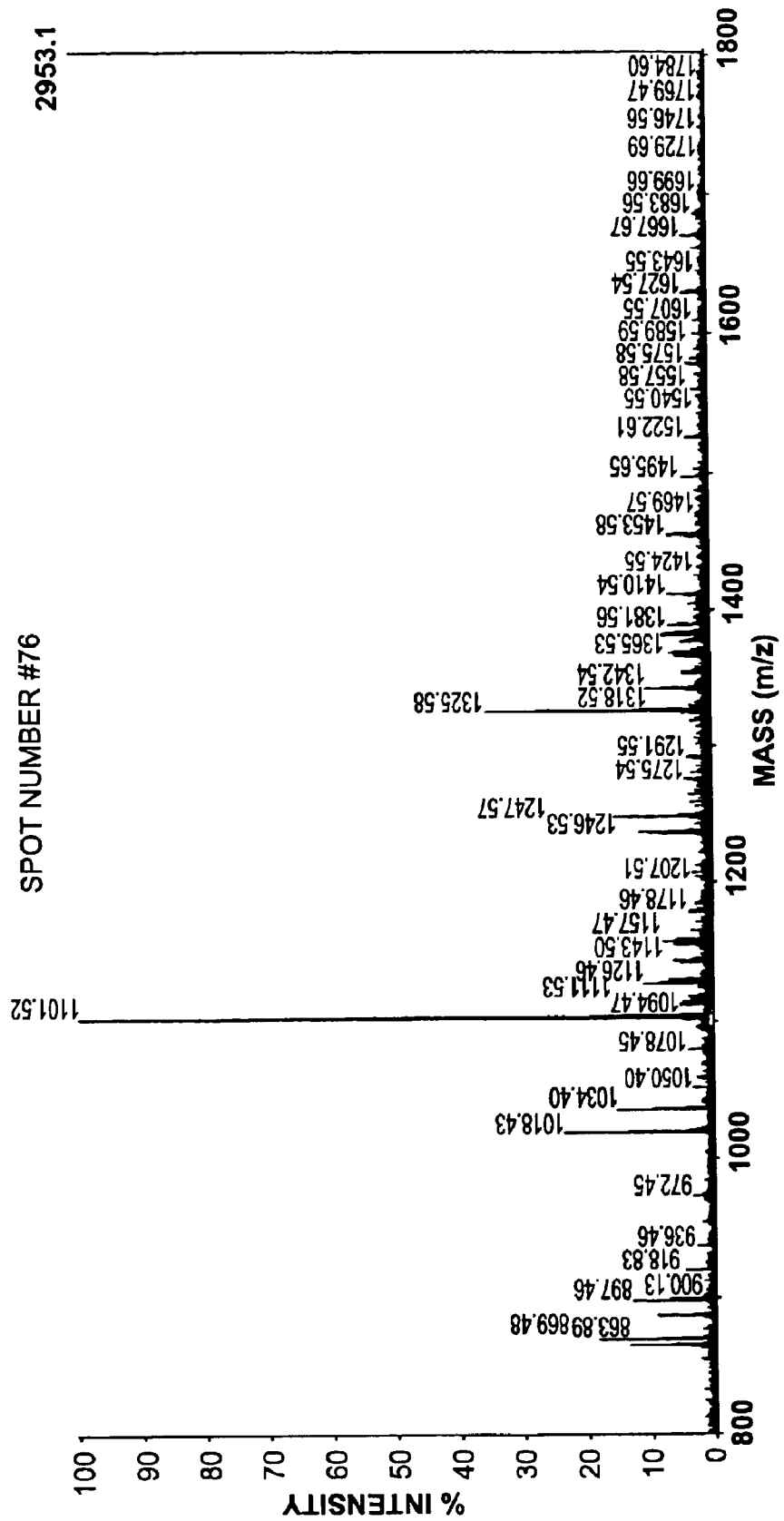
Figure 10F:
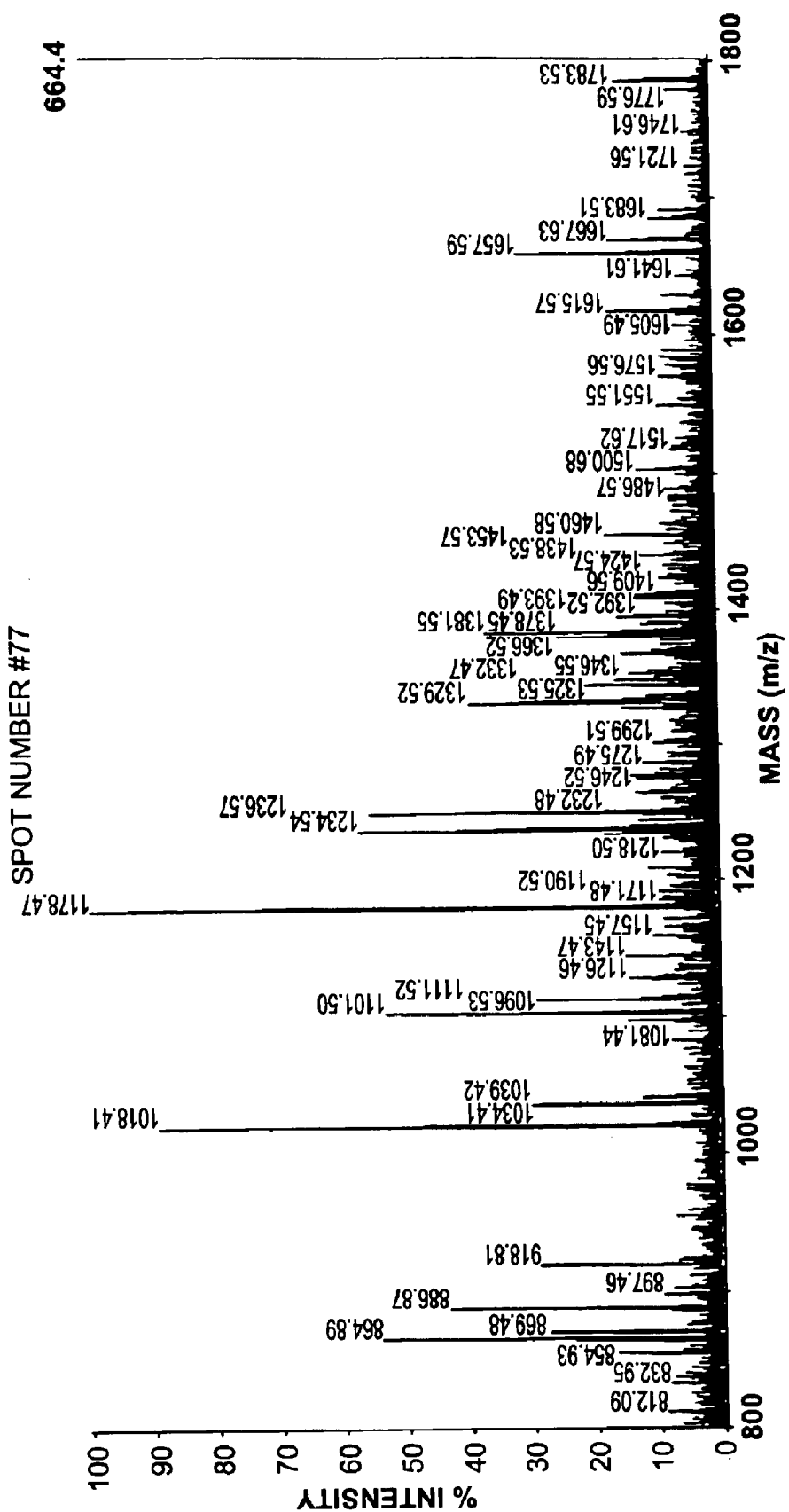
Figure 11A:
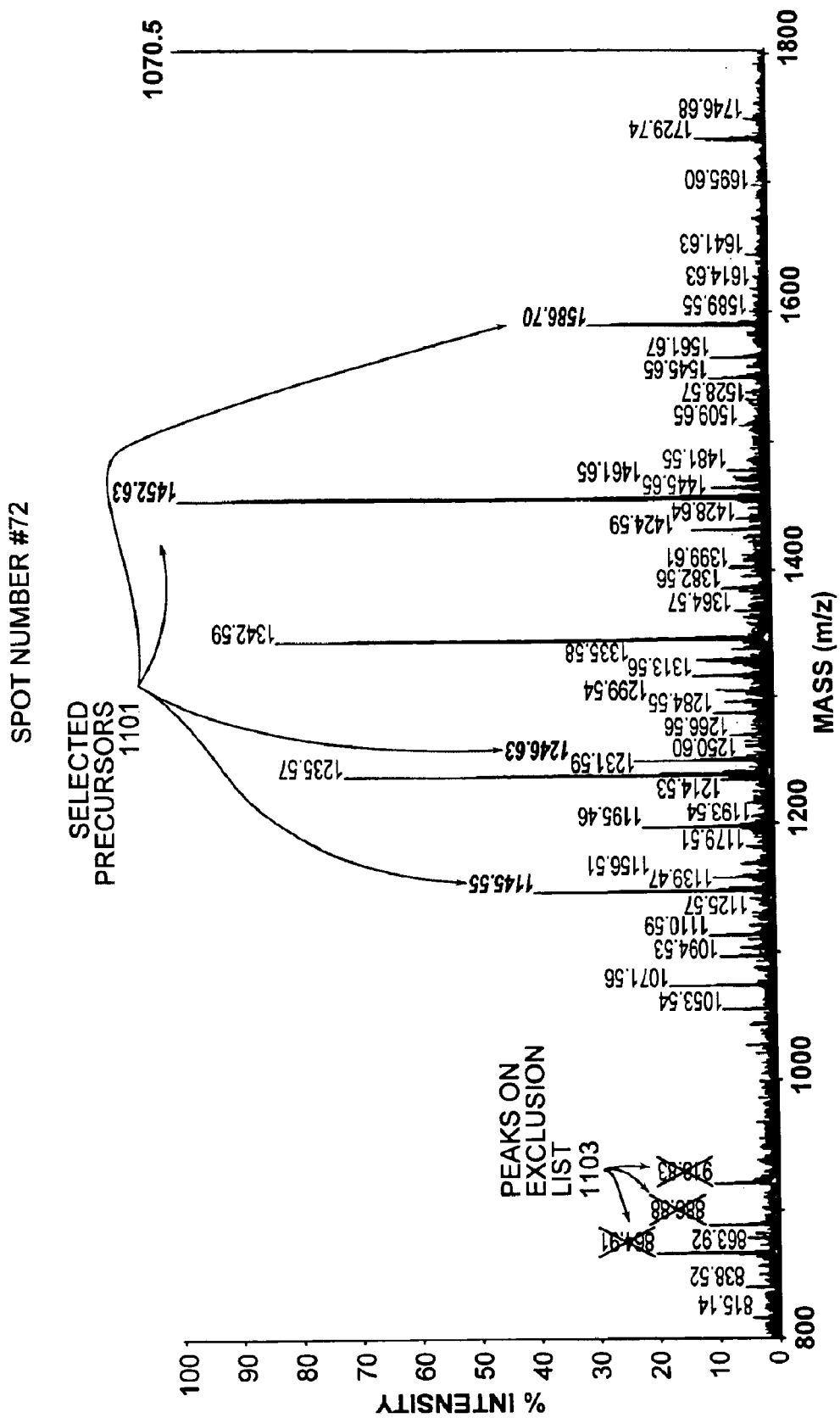
FIGS. 11A–11F are examples of peak selection for further MS analysis in Example 1.
Figure 11B:
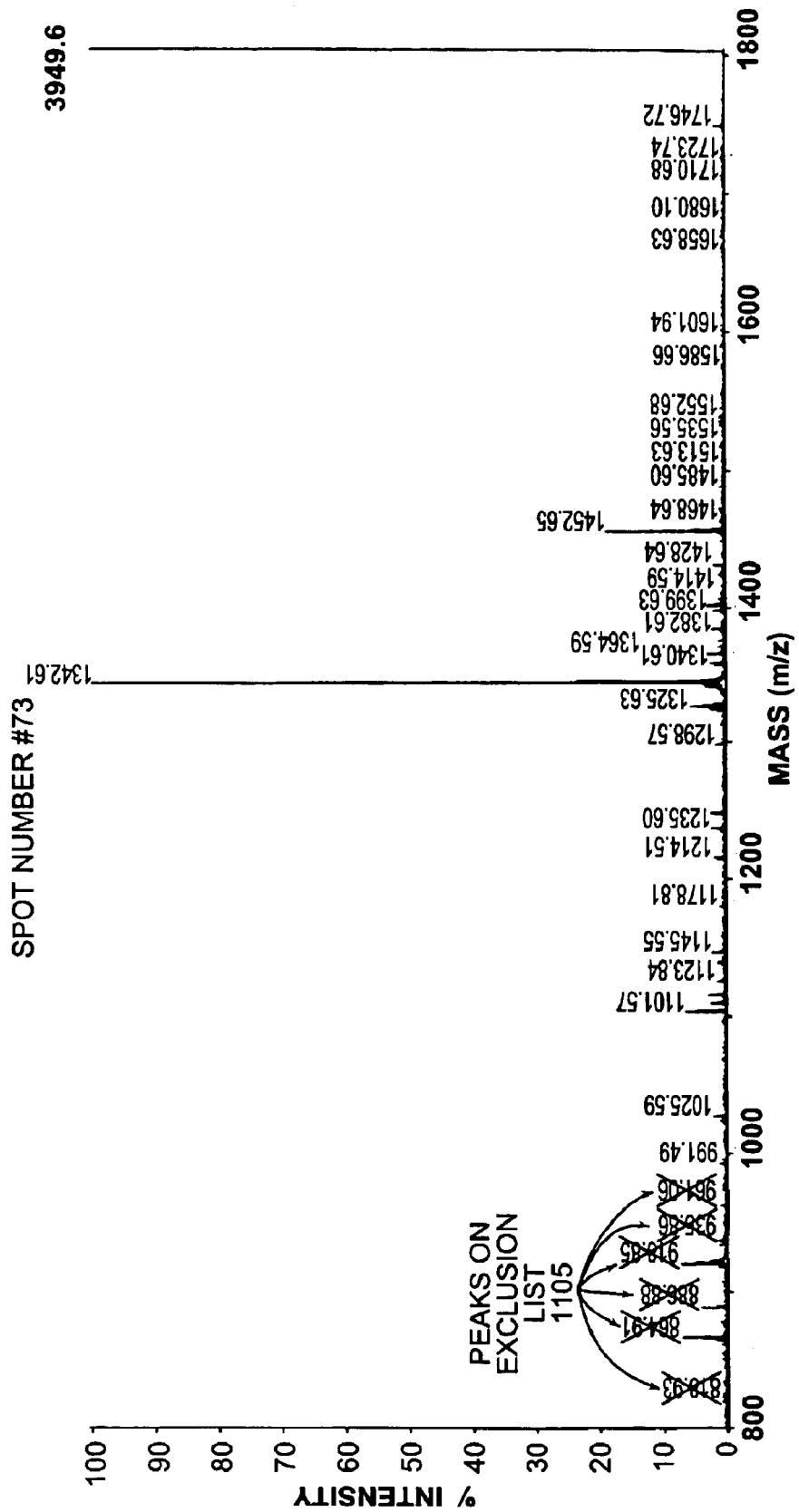
Figure 11C:
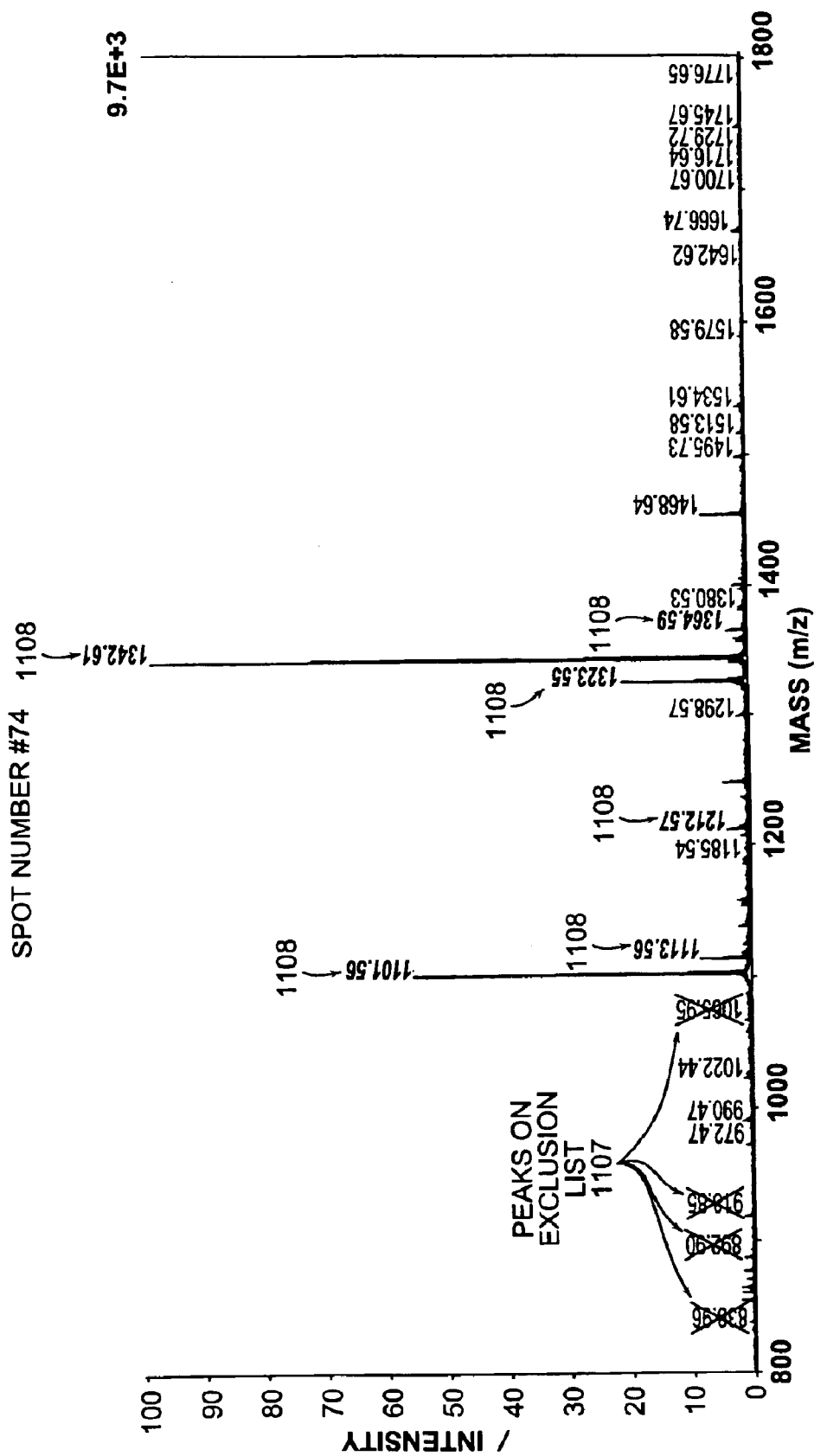
Figure 11D:
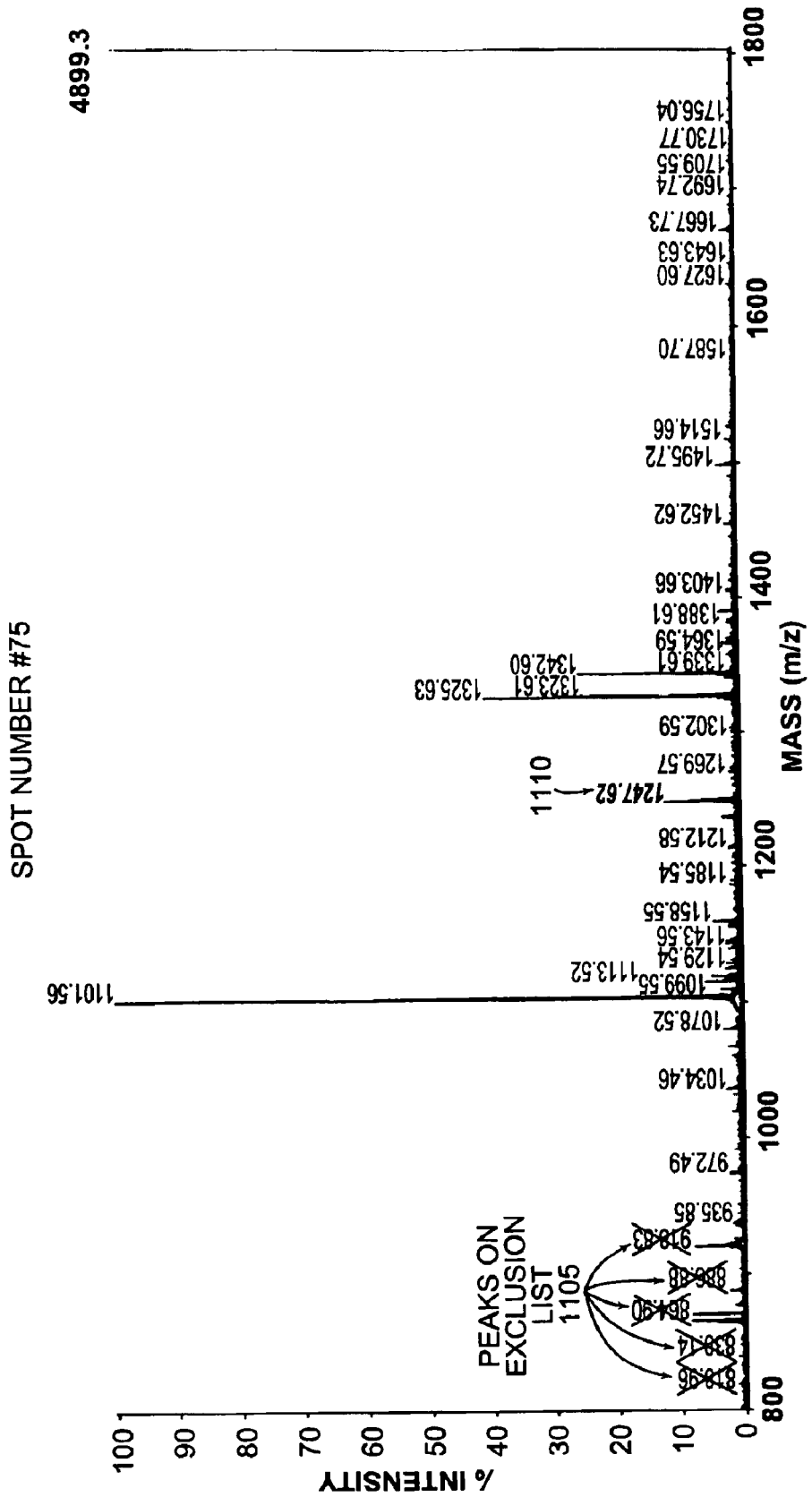
Figure 11E:
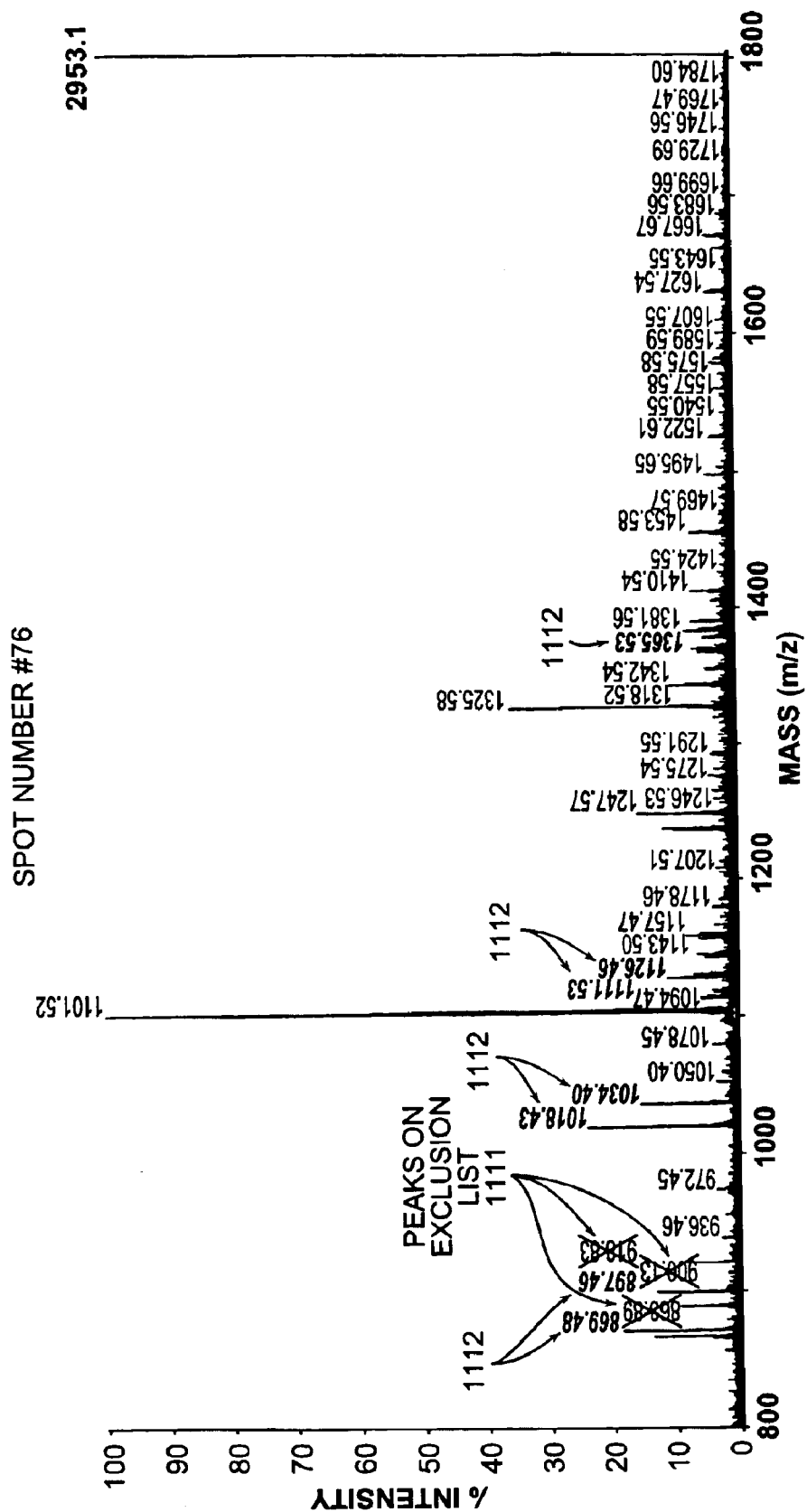
Figure 11F:
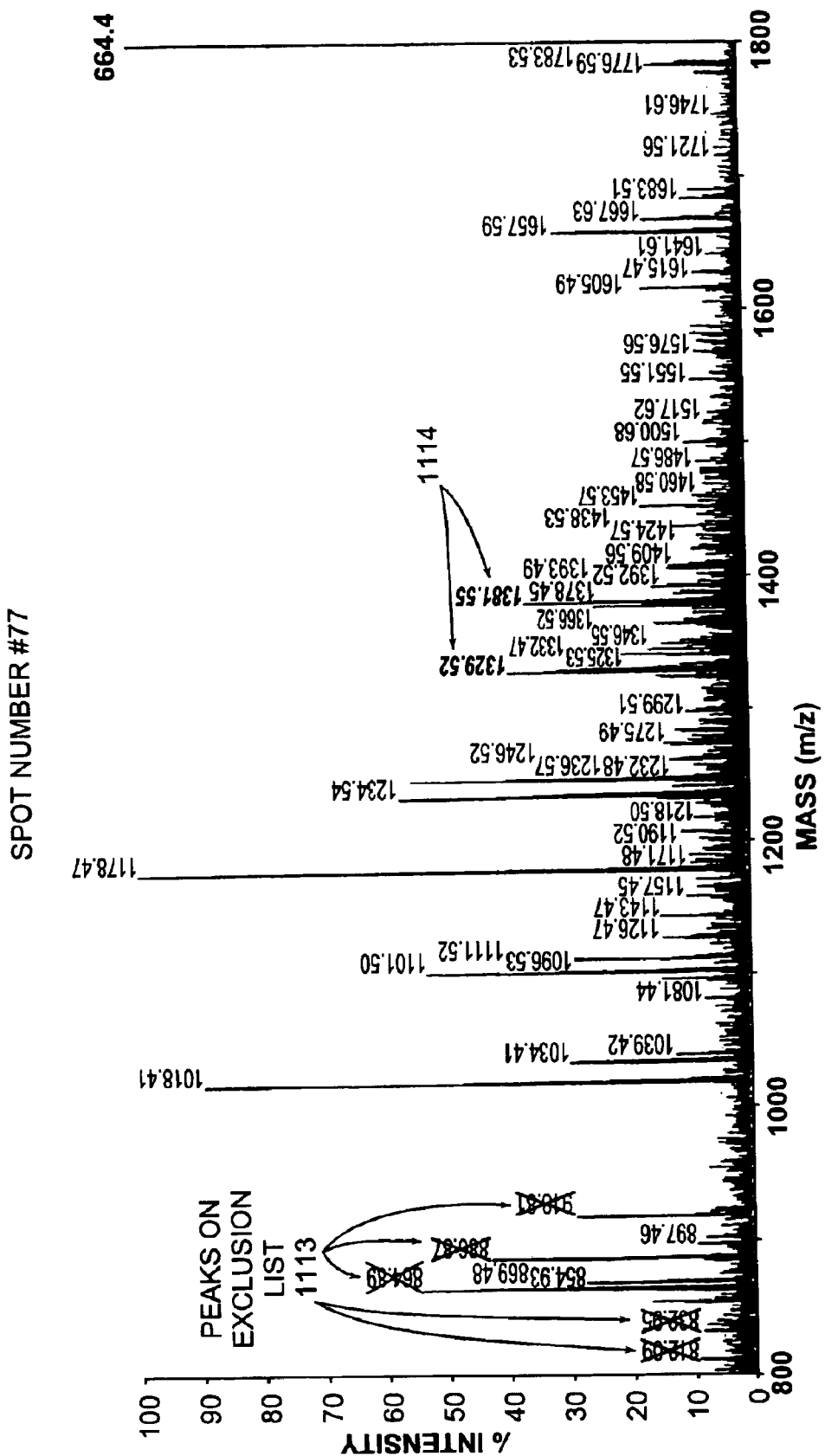

FIG. 9 depicts a microbore HPLC chromatograph 901 showing various eluent fractions, were it is understood that several biomolecules, can be in a single fraction and that a given biomolecule can be present in multiple fractions. In various embodiments, as the fractions elute they can be spotted 903 onto a MALDI sample plate 905. A single fraction, depending on the length of elution and the sampling rate, can be spotted as multiple spots 904 on the MALDI sample plate 903 and mass spectra acquired using, for example, MALDI and TOF mass spectrometry 906. Proteins can be identified in the biological sample from mass spectra of a plurality of eluents from various retention times (here multiple spots) 907 or a single retention time can suffice to identify a protein 909.

Examples of the resultant mass spectra are shown, respectively, for spot numbers 72–77 in FIGS. 10A–10F. In this example, peaks were selected for further analysis based on the intensity of the peak cluster area over a series of mass spectra determined by the elution profile of the corresponding peak. For example, the series of mass spectra for spot numbers 72–77 (FIGS. 10A–10F) correspond to a sequence of eluents form the HPLC column, i.e., here the sample of spot 72 eluted before that of spot 73, which eluted before that of spot 74, etc. In this example, the number of mass spectra that relate to the elution profile of a peptide was determined dynamically for each peak mass that is within a specified tolerance. Precursors were then selected based on the maximum cluster intensity within each elution profile. For example, if the determined elution profile for a peptide was a minute and the fraction collector spotted every 20 seconds, then the number of mass spectra in the considered time window was 3. Similarly, if the number of mass spectra a peptide could be (e.g., due to elution rate, sampling rate, etc.) was ten, the number of cluster intensities used to select a further analysis run was 10.

FIGS. 11A–11F illustrate the peaks selected 1101, 1108, 1110, 1112, 1114 for further MS analysis (e.g., select precursors) where the selection criteria selected only the most intense peaks (based on cluster intensity) with a signal-to-noise above 10 and a cluster area above 1000 that can be considered to be different within a certain retention time and mass tolerance window. Also illustrated are masses specifically excluded for further consideration 1103, 1105, 1107, 1109, 1111, 1113 based, for example, mass ranges not of interest, a mass cut-off masses associated with known contaminants, etc. The mass selected, are then subject to further MS analysis to identify the peptide associated with the mass peak. A plurality of peptide identifications were then used to identify proteins present in the biological sample.

Example 2

Expression Based Analysis Precursor Selection

Figure 12:
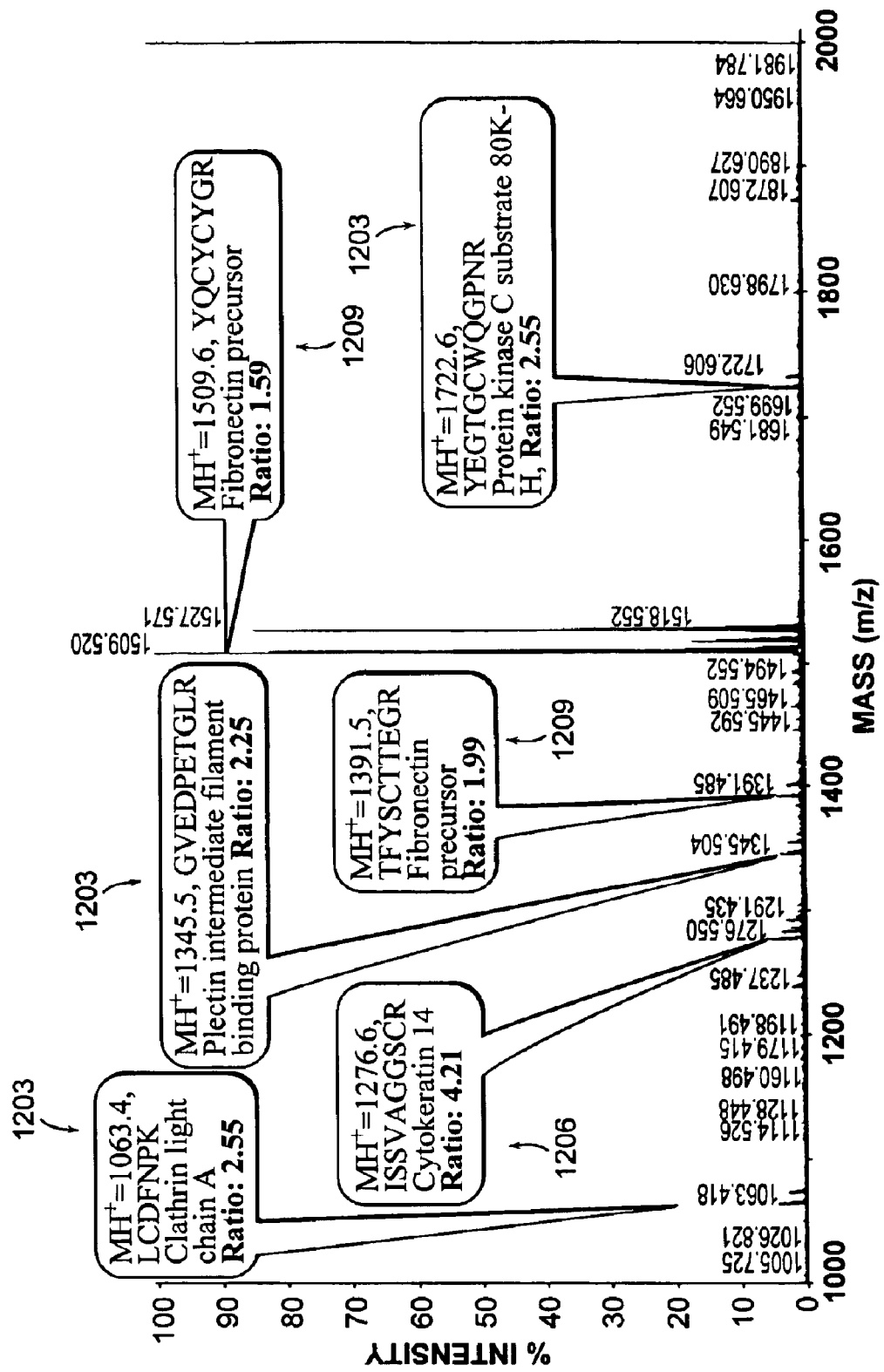
FIG. 12 is a example of a mass spectra obtained in Example 2.

FIG. 12, shows another example of selection based on expression dependence using ICAT quantification. The results are for HS stimulated fibroblast cell nuclei. The average median light:heavy ratio was about 2.5 In this example, peptides with an average light:heavy ratio are not substantially regulated 1203, whereas peptides with a high light:heavy ratio are upregulated 1206, and those with a low light:heavy ratio are downregulated 1209. Peaks are then selected for further analysis based on the observed regulation. For example, further MS analysis can be conducted only on upregulated masses, downregulated masses, non-regulated masses, or combinations thereof. In addition, peaks for further analysis can be selected not only on the qualitative nature of the regulation but on a quantitative basis as well.

Figure 13:
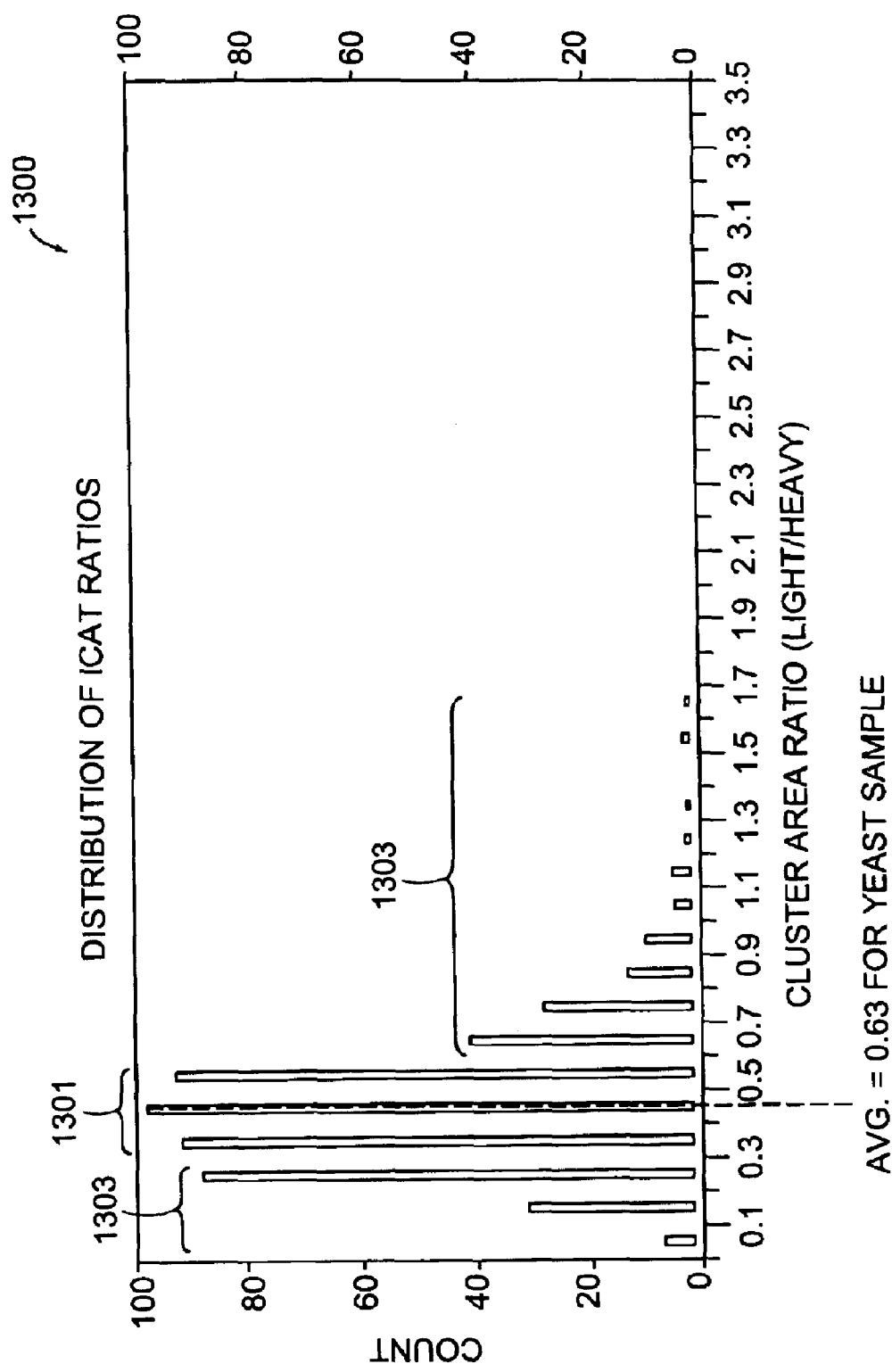
FIG. 13 is a schematic illustration of various embodiments of an expression dependent precursor selection.
Figure 14A:
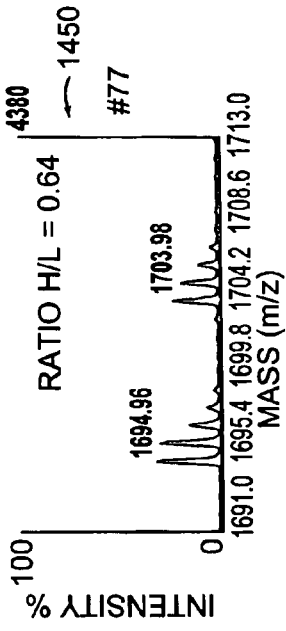
FIGS. 14A–14F illustrate examples of the mass spectra of non-differential expressed pairs that co-eluted.
Figure 14B:
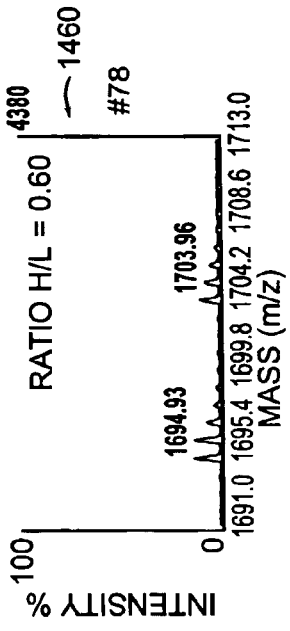
Figure 14C:
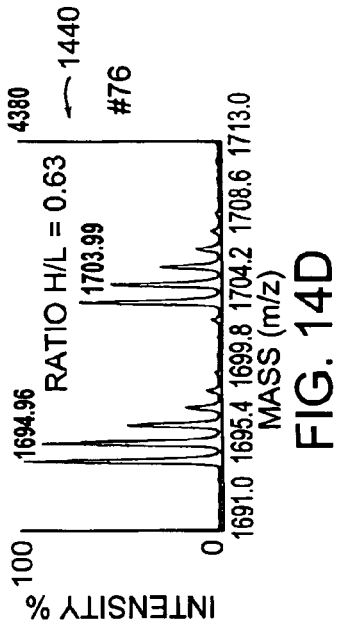
Figure 14D:
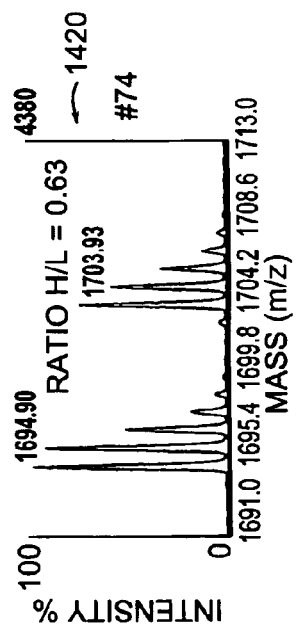
Figure 14E:
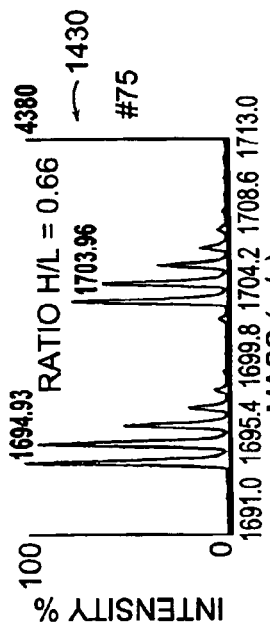
Figure 14F:
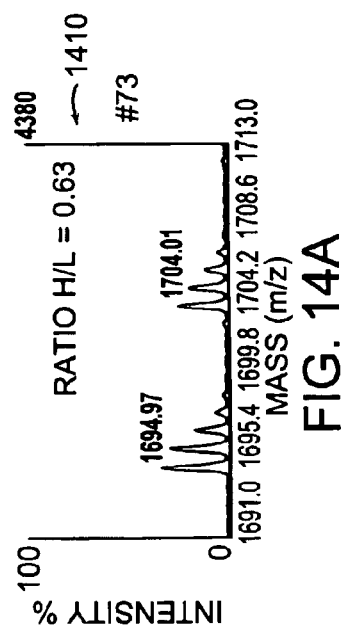

Referring to FIG. 13, a distribution of ICAT ratios 1300 can be used to determine peaks for further analysis. Peaks can be selected, for example, based on whether evidence of nondifferential expression 1301 or differential expression 1303. Further, for example, peaks can be selected based on whether they are a certain number of standard deviations from the mean or median of the distribution 1300. In FIG. 13, the average expression level ratio was 0.63.

Figure 15:
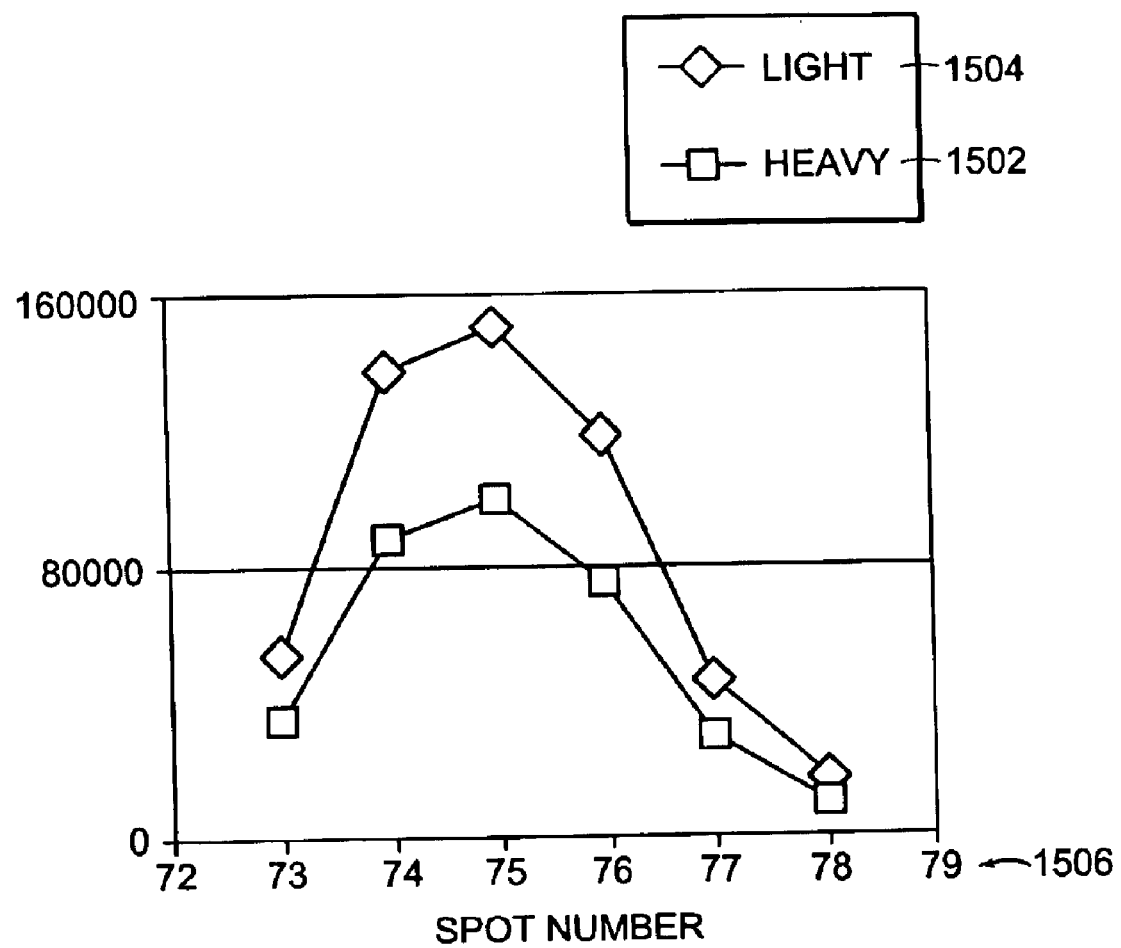
FIG. 15 is a plot of the signal of the high mass clusters and low mass clusters for the mass spectra shown in FIG. 11.

In addition, referring to FIGS. 14A–14F and 15, isotope ratio information can be combined with retention time based information. As illustrated in FIG. 14, a series of mass spectra 1410, 1420, 1430, 1440, 1450, 1460 (here spot numbers 73–78, which do not correspond to the spot numbers of FIGS. 10A–10F and 11A–11F) showing the co-elution of a non-differentially expressed pair with a low mass peak cluster at approximately 1695 and a high mass cluster at approximately 1704. If the low or/and high mass peak of the pair are selected for further analysis, then the mass with the highest cluster intensity in spot number 75 will be selected within the shown elution profile for further analysis. In FIG. 14, the average expression level ratio was 0.63 with a standard deviation of 0.02. FIG. 15 illustrates the similarity of the elution profiles of the peptides with the heavy 1502 and light 1504 labels. The variation of the peak ratios across these six 5 second HPLC fractions is less than 3% in this example. Under these conditions, the quantification of proteins reduces to the measurement of relative ion abundances in MS spectra. Change in isotope signal is shown in FIG. 15 for light cluster signals 1504, represented by diamonds, and heavy cluster signals 1502, represented by squares, as a function of spot number 1506 (i.e., retention time).

Example 3

Correction of Putative Expression Values

Figure 16:
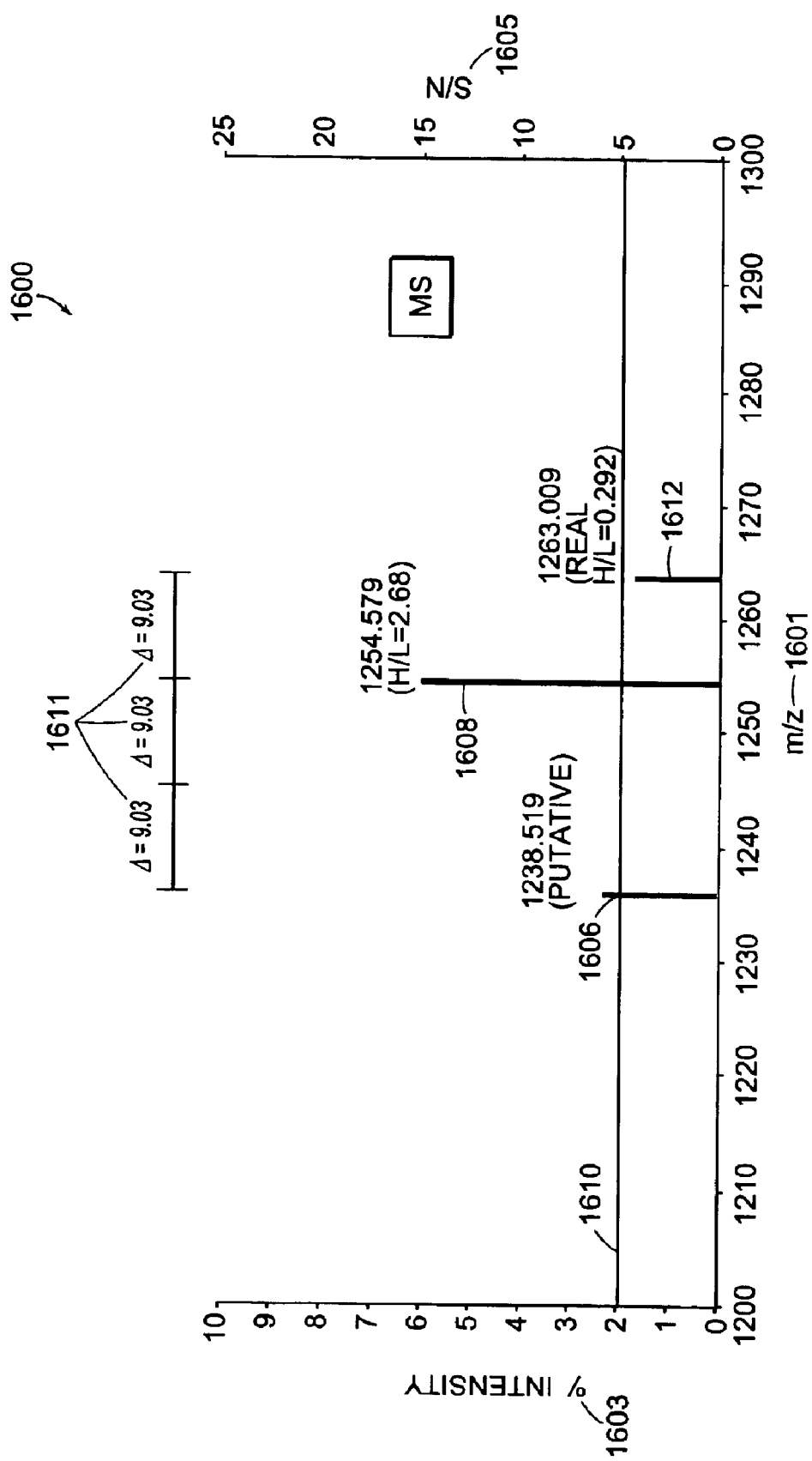
FIG. 16 illustrates various embodiments of correction of putative expression values.

FIG. 16 illustrates various embodiments of correction of putative expression values where peak quantitation was inconsistent with peptide identification. FIG. 16 is a diagram of a MS spectrum 1600 where mass is in units of m/z 1601, and mass signal intensity is given in both % intensity 1603 and as S/N ratio 1605. This mass spectrum contains two peaks 1606, 1608 above the initial peak detection threshold 1610 of SIN ration greater than 5.

The MS spectrum shows an ICAT pair and a singleton peak. At first the peak 1608 at mass 1254.579 was erroneously assigned as the heavy form of the peak at 1236.519, 1606, which would require two cys, and the peak at 1263.609, 1612 was below the threshold for peak detection. In the first pass, this ICAT pair has a ratio of 2.68, which signifies up-regulation, considering the median ratio was 0.5 (heavy/light). Database searching identified the peak at 1254.579 as the $^{12}C$ light form of the peptide YLATCADDR, which contains only one cys. When the peak at 1254 amu 1608 was matched to a peptide containing one $^{12}C$ cys residue, instead of two $^{13}C$ cys residues, the intensity threshold was lowered, resulting in detection of a new peak at 1263, 1612 and recalculation of the ICAT reagent ratio. With this new information, the QuantFixer program identified the peak at 1263.608, and calculates a heavy/light ratio of 0.292, which signifies down-regulation. The corrected expression level ratio will be annotated in the database indicating uncertainty about the true ratio because of a possible second overlapping ICAT pair (as evidenced by the singleton) which remains unidentified.

Example 4

Expression Based Analysis and Expression Data Dependent Workflow

An expression data dependent workflow has been exploited as part of a hypothesis-driven systems biology study to identify potential transcriptional and translational control elements involved in nonsense mediated mRNA decay (NMD) in *Saccharomyces cerevisiae*. NMD is an important biological process responsible for the rapid turnover of mRNAs containing premature stop codons, unspliced premRNAs that enter the cytoplasm, RNAs with upstream ORFs, transcripts with extended 3' untranslated regions and transcripts with a poor translation initiation context. A mutant strain of *S. cerevisiae* containing a knockout of Upf1, a factor known to be involved in the regulation of the NMD process was compared to a wild type strain at both the message and protein levels.

To better understand the complexity of cellular processes such as NMD, complementary techniques can provide the necessary specifics to unravel the mechanism of interactions, pathways of signal transduction and networks of regulation. In this example the two MS ionization techniques ESI and MALDI were utilized to expand the depth of protein coverage in order to allow a comparison with transcript expression levels, gained by mRNA arrays analysis.

Non-differentially expressed, differentially expressed and singletons were selected for MALDI MS/MS analysis in order to investigate expression differences at the protein and mRNA level at a wide scale.

This example investigates NMD in *Saccharomyces cerevisiae* and examines quantitatively the expression profile of the cell at multiple levels, e.g., at both the transcriptome and proteome level. Protein expression is usually poorly correlated with mRNA abundance, presumably because mRNA degradation, alternative splicing, co- and post-translational modification, and post-transcriptional regulation of gene expression make it difficult to extrapolate from mRNA to protein profiles and cellular function. Thus, differentially expressed proteins may not be co-induced or co-repressed at the mRNA level.

This example reveals that, CPA1 (P07258), which is involved in the GO biological process of arginine biosynthesis, is up-regulated at the message and protein level in the Upf1 knockout strain.

The Peak Picker software tool reported about 8% of the observed ICAT reagent labeled mass signals changing by more than 2 σ from the median expression level ratio. After peptide identification by MS/MS analysis and MS/MS ion and sequence database searching, and correction step of putative expression values with the Quantfixer software tool only about 4% of the peptides were confirmed of being differentially expressed by more than 2 σ.

The difference of these representative percentages can be influenced by a number of factors, such as sample complexity, level of fractionation, quality of MS and MS/MS spectra, peak detection, peptide identification and the completeness of reference databases. The chances of missing an ICAT reagent-modified peptide can be lowered by setting a low signal to noise filter threshold (lower false negative rate), but at the cost of increasing HL pair signals that are not identifiable (e.g. some of the newly enumerated HL pairs are explainable by random matches to noise signals, signals too weak for MS/MS identification), or overlapping peaks that cannot be successfully de-convoluted, especially in complex samples or upon insufficient fractionation. HL pair assignments to noise signals and to overlapping peaks can result in extreme HL ratios that cannot be confirmed or may not be interpretable by the Quantfixer software tool. In the second case, quantitation values have to be flagged as not reliable. An expression dependent workflow can be more efficient by considerably reducing the number of MS/MS spectra (466 out of 5850 signal ratios change by more than 2 σ). False positive non-peptide precursor signals can be filtered out at the MS/MS ion search identification level. A threshold based on σ may not be appropriate when the ratios are wide spread. Then ratio fold changes can be more meaningful.

The underlying MS, MS/MS, protein and mRNA related experimental results were deposited into a relational database. The mRNA ratios and protein ratios were made comparable by dividing by the median of the respective ratio. Proteins were linked through reference lists with corresponding genes and open reading frames (ORFs), and associated to codon bias and gene ontology information, such as biological process, molecular function and subcellular location (available at MIPS: http://mips.gsf.de/ or SGD: http://genome-www.stanford.edu/*Saccharomyces*/).

FIG. 6 outlines tables that have been used to facilitate generating FIGS. 19A–21B. FIG. 7 outlines various relationships used with the tables of FIG. 6. The included SQL example extracts the Protein Accession Nr, ORF, Protein and mRNA expression values and Codon Bias for all Proteins with biological function involved in Arginine Biosynthesis.

Figure 17:
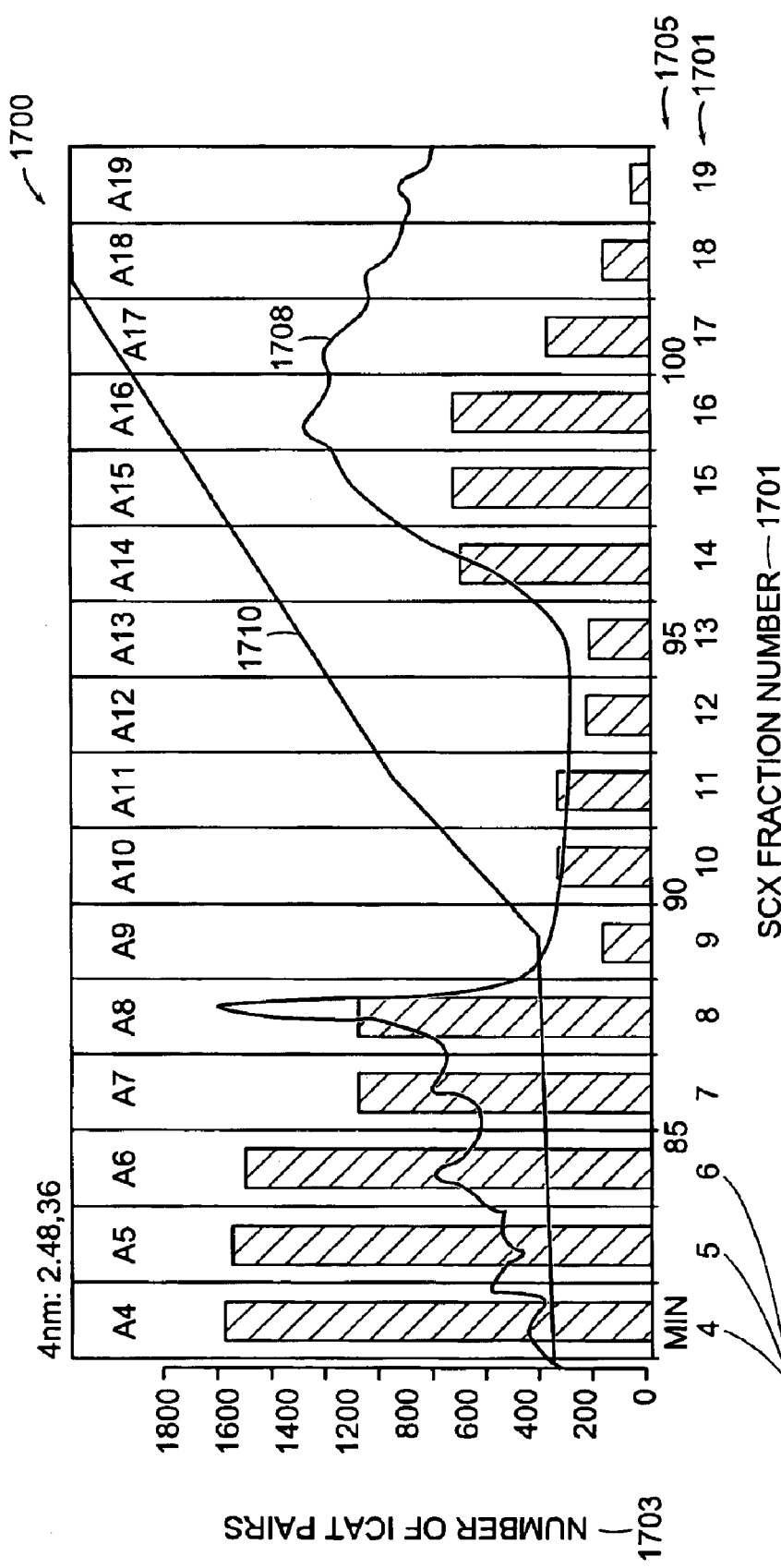
FIG. 17 is a chart depicting the number of ICAT reagent pairs per SCX fraction for the yeast study of Example 4.

FIG. 17 is a chart 1700 depicting the number of ICAT reagent pairs 1703 per SCX fraction 1701 in the yeast NMD system biology study. The histogram illustrates the ICAT reagent pairs observed by MALDI as a function of SCX fraction number 1701 and time 1705. There were 10,801 pairs observed in total, almost 1600 in each of three early fractions 1706. Overlaid on top of the histogram is the UV trace 1708 for the SCX run. One can see that the UV signal (280 nm) coincides with the location of the majority of the ICAT reagent pairs.

The dynamic-exclusion algorithm of the Peak Picker software program reduced the 10,801 putative ICAT reagent pairs observed to 5,850 pairs. The 10,801 ICAT reagent pairs have a median ratio near 1 (0.972) and σ of 0.229. This highlights that most observed ICAT reagent pairs do not change between the Upf1 mutant and wild type strains. This tight distribution also reflects the high precision of the technique. In this example, ~8% of the observed signals change by more than 2 σ (~40% up- or down regulated). After a quantitation correction step with QuantFixer only 41 out of 1121 unique identified peptides (~4% with expression greater than 2 σ) are considered reliable.

Figure 18:
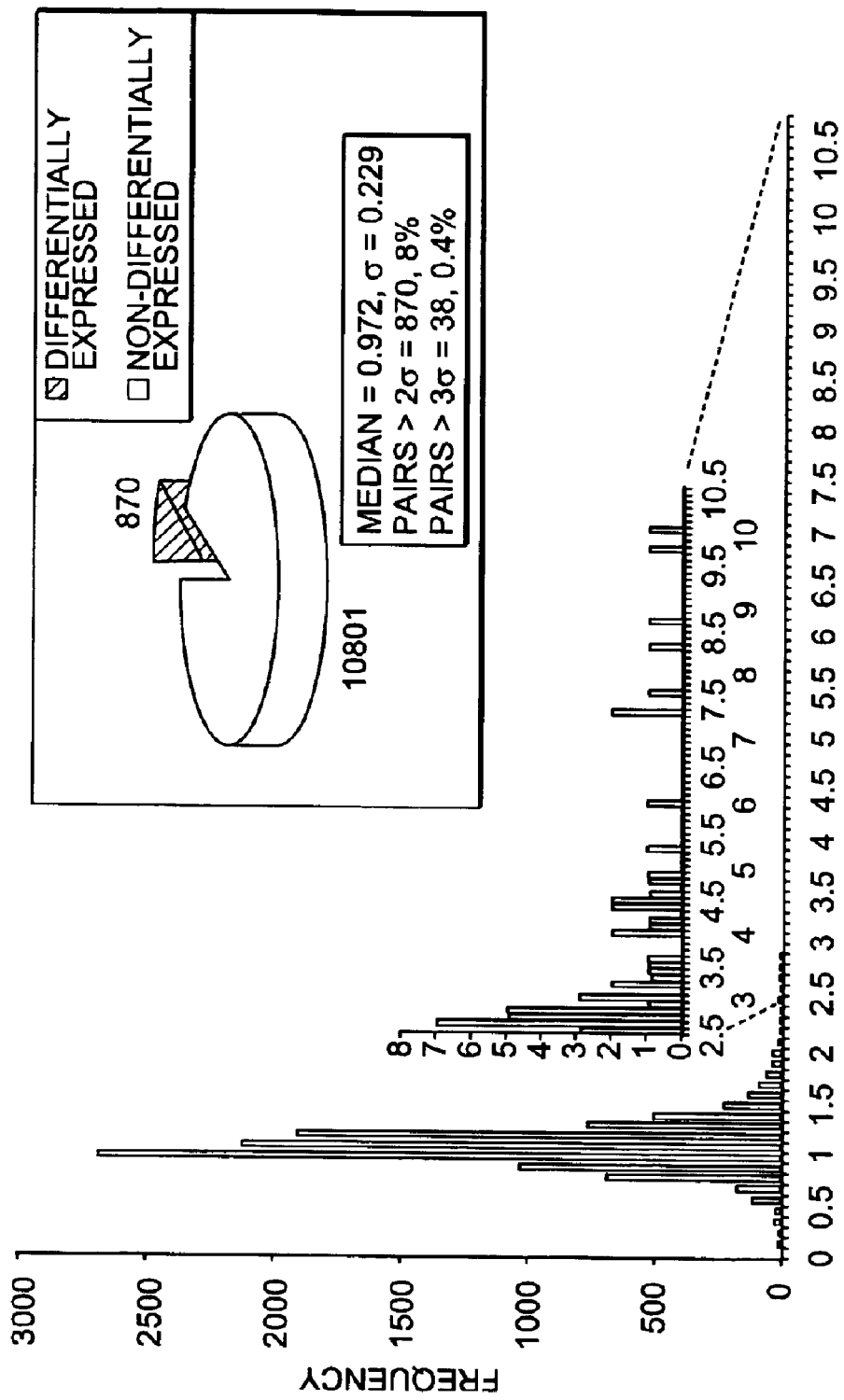
FIG. 18 depicts a histogram of HL ratios for the yeast study of Example 4.

FIG. 18 depicts a histogram of heavy/light ratios in yeast NMD system biology study and pie-chart showing the fraction of differential expression 1800. The 10,801 ICAT reagent pairs have a median ratio near 1 (0.972) and σ of 0.229 (~20%). In this MALDI analysis, 92% of the observed signals are changing by less than 2 σ (~40% up- or down regulated). In total, 898 unique proteins were identified and quantified by MALDI and ESI see FIGS. 19A and 19B. The overlap between the proteins identified by both ionization techniques was 51.7% demonstrating that many more proteins can be identified and quantified when both ionization techniques are used.

Figure 20A:
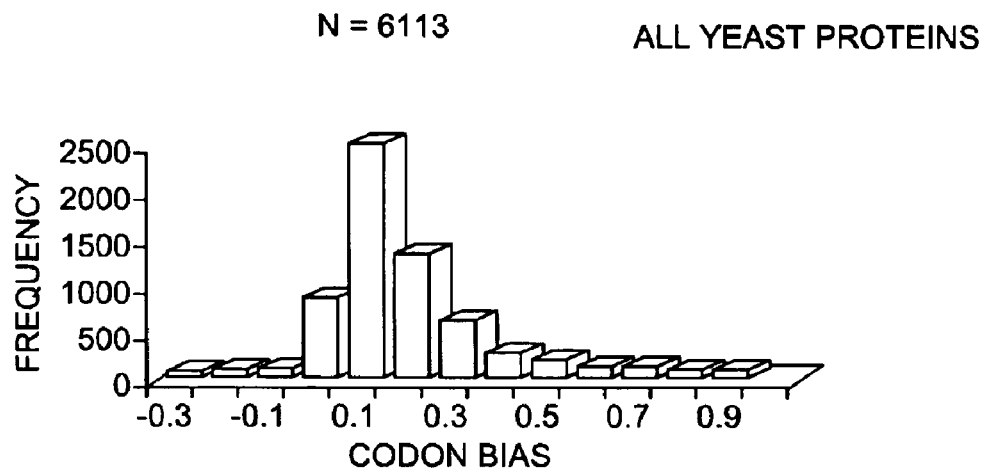
FIGS. 20A and 20C show a codon bias comparison of reported and experimentally observed yeast proteins of Example 4.
Figure 20B:
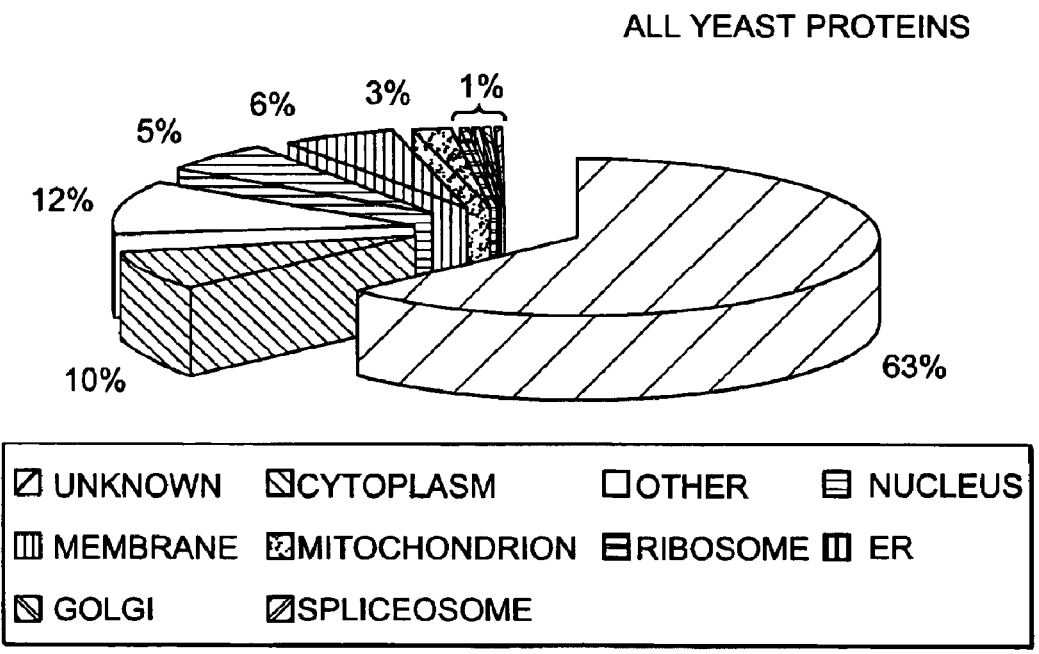
FIGS. 20B and 20D illustrate the sub-cellular location of reported and experimentally observed yeast proteins of Example 4.

Codon bias is a measure of the expected protein abundance, 167 proteins seem to be of low abundance (<0.1) by considering the codon bias values (see FIGS. 20A–20B). However, the 898 proteins that have been identified presumably represent proteins that are most easily identifiable. Thus, the technique of this example can detect some low abundance proteins because of favorable peptide properties. Alternatively, the good correlation of the codon bias with protein abundance may extend only to the most abundant two hundred proteins or so.

Figure 19A:
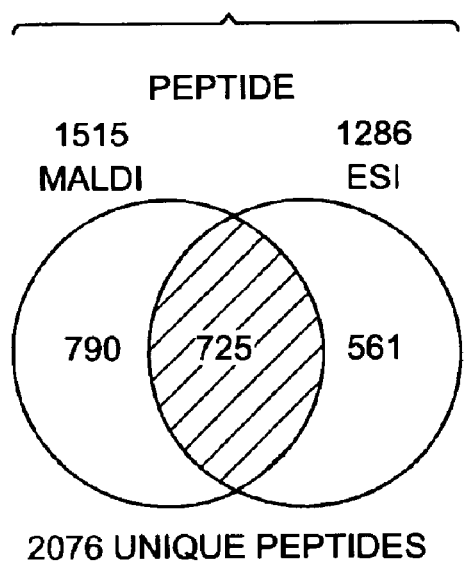
FIGS. 19A and 19B, illustrate, respectively, the peptides and the proteins. identified in the yeast study of Example 4.
Figure 19B:
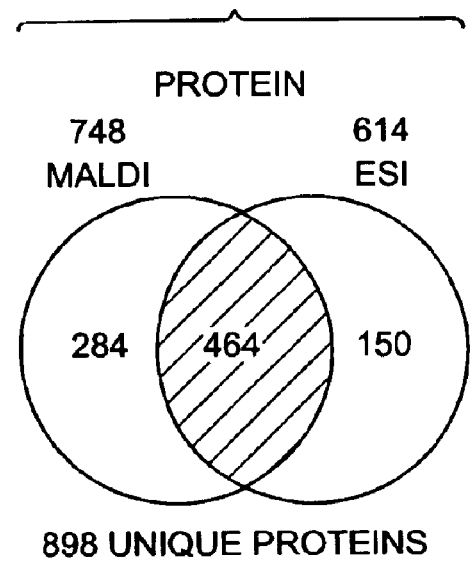

FIGS. 19A and 19B, illustrate, respectively, the peptides and the proteins. identified in the yeast NMD system biology study. 898 MALDI and ESI proteins, and 2076 peptides were quantified and identified by MASCOT (p<0.05, i.e. ion score>20, Swiss-Prot Database (v02.13.2003)). Proteins were considered, if they contained at least one significant identified peptide.

Figure 20C:
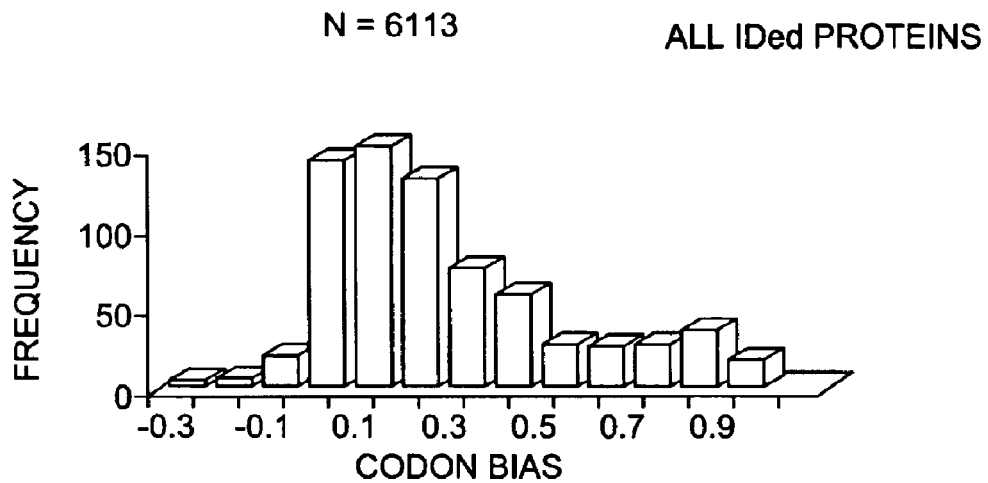

FIGS. 20A and 20C show a codon bias comparison of reported and experimentally observed yeast proteins. Each bin in FIGS. 20A and 20C consists of 0.1 units along the codon bias scale. As expected, the identified proteins tend to have higher-than-usual codon biases. However, some proteins with codon bias <0.1 were identified.

Figure 20D:
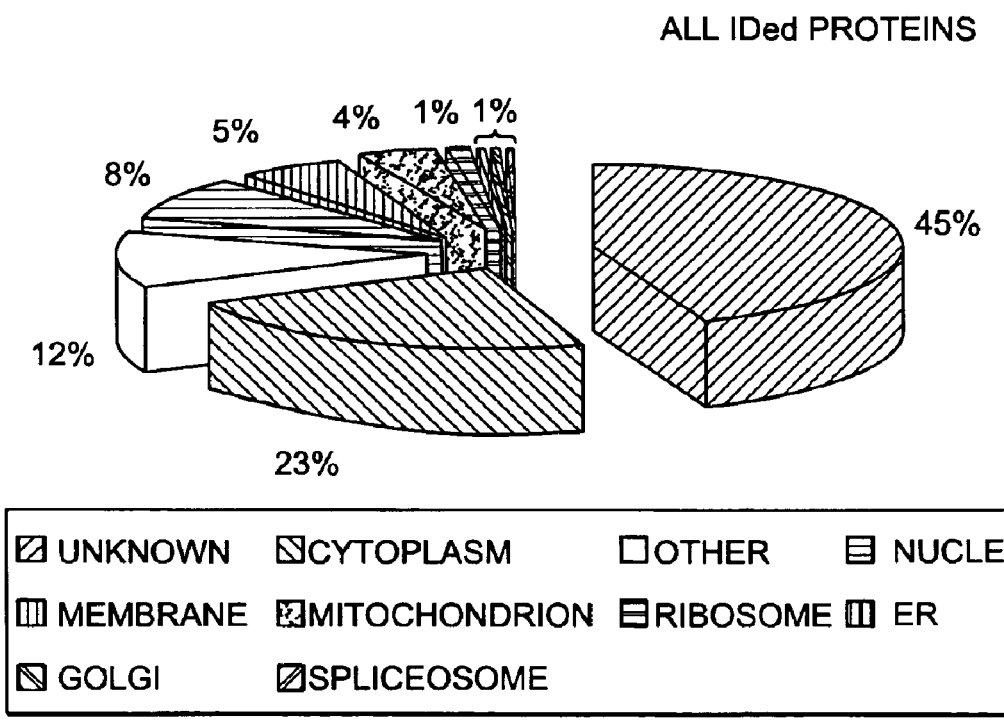

FIGS. 20B and 20D illustrate the sub-cellular location of reported and experimentally observed yeast proteins. All reported yeast proteins at MIPS and SGD were classified by sub-cellular location in this example. FIGS. 20B and 20D show the distribution of the proteins identified in this study, as compared to all yeast proteins. This illustrates that the expression data dependent technique of this example detects proteins from all classes, including membrane proteins, which are difficult to detect using 2D gels.

Generally speaking, few proteins changed in expression level upon knock-out of the UPF1 gene. The Upf1 protein itself was at the borderline of detection, and was indeed lower in the knock-out. Unfortunately, in this example the absolute level of expression of Upf1 was so low that it only could be determined that the Upf1 protein was down-regulated by at least 5-fold, because of background signals in the position of the heavy form of the Upf1 peptide. Upon knock-out it should be completely absent. Most of the other significant quantitative changes that were observed are in proteins that seem to bear no obvious functional relationship to one another, whether proteins are categorized by biological process, molecular function, or cellular compartment, using the GO gene ontology system. This may be because less than one sixth of all proteins (predicted from 6,113 genes) have been measured.

Figure 21A:
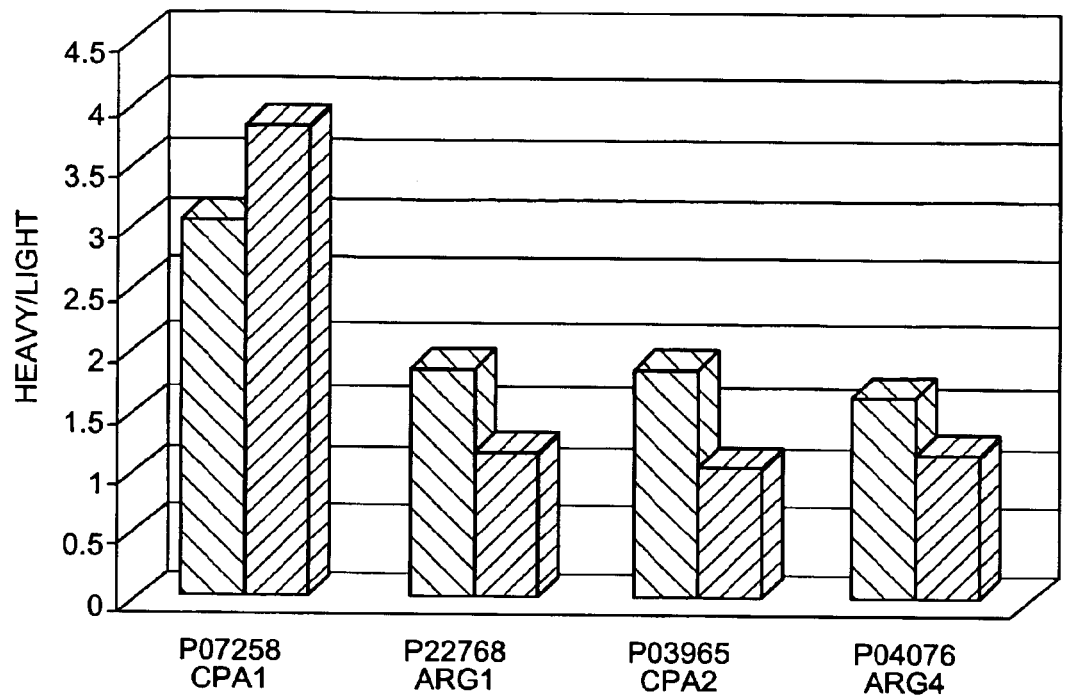
FIG. 21A illustrates ICAT reagent and mRNA ratios of arginine biosynthesis enzymes.
Figure 21B:
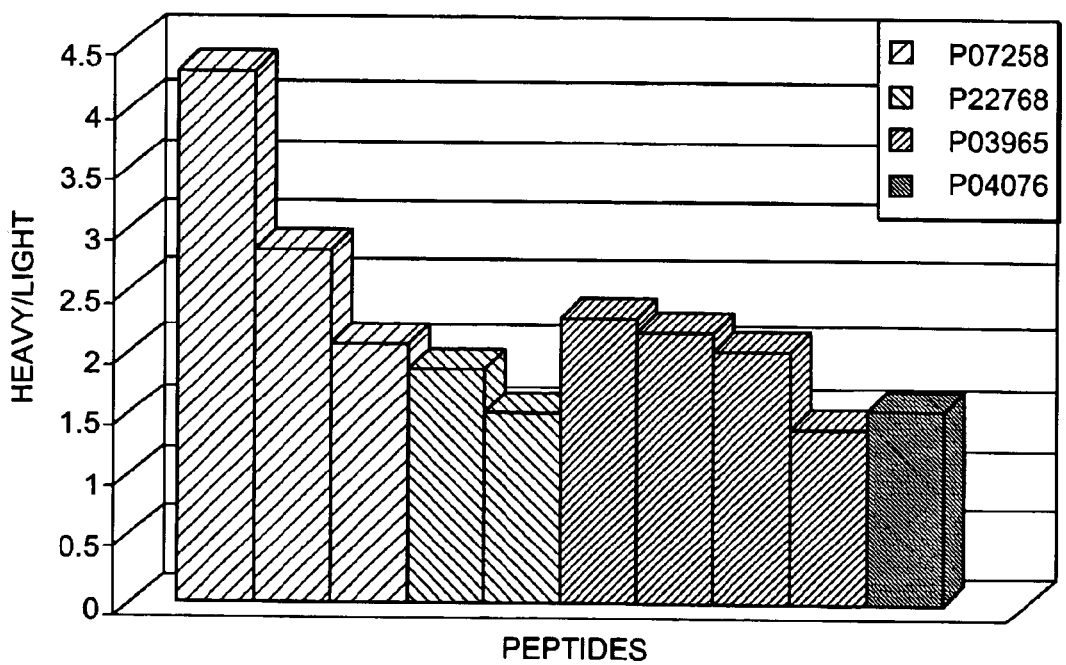
FIG. 21B illustrates ICAT reagent and mRNA ratios of arginine biosynthesis enzymes peptides.

FIG. 21A illustrates ICAT reagent and mRNA ratios of arginine biosynthesis enzymes. CPA1, ARG1, CPA2 and ARG4 show a co-up-regulation in both message and protein level. FIG. 21B illustrates ICAT reagent and mRNA ratios of arginine biosynthesis enzymes peptides. All peptides from 4 different arginine biosynthesis enzymes have an ICAT Ratio of >1.4. A ratio of 1 indicates no differential expression. An exception to this generalization is in the GO biological process of arginine biosynthesis, where 4 out of 5 proteins listed were observed. All 4 had increased expression in the Upf1 knockout strain. For these 4 proteins, there were no discordant measurements below an ICAT reagent ratio of 1.4. One of these proteins, CPA1 (P07258), which encodes the small subunit of carbamoyl phosphate synthetase, increases in expression upon mutation of the Upf1 gene in concordance with our data. Our data also indicate that expression at the protein level of the large subunit of carbamoyl phosphate synthetase (CPA2) is also increased in the UPF1 knockout strain. Both subunits of carbamoyl phosphate synthetase have been shown to be co-regulated in *Saccharomyces*.

Table 2 lists the peptide and protein ICAT reagent expression ratios of arginine biosynthesis enzymes observed with MALDI and ESI, the ratios are listed together with normalized mRNA ratios.

TABLE 2

| SWISS-Prot Accession | Protein Name | H/L MS[a] Ratio | Stdv[a] | N | Gene | ORF | H/L mRNA Ratio |
|---|---|---|---|---|---|---|---|
| P07258 | CARBAMOYL-PHOSPHATE SYNTHASE, ARGININE-SPECIFIC, SMALL CHAIN (EC 6.3.5.5) | 3.06 | 0.45 | 3 | CPA1 | YOR303W | 3.83 |
| P22768 | ARGININOSUCCINATE SYNTHASE (EC 6.3.4.5) | 1.84 | 0.04 | 3 | ARG1 | YOL058W | 1.11 |
| P03965 | CARBAMOYL-PHOSPHATE SYNTHASE, ARGININE-SPECIFIC | 1.85 | 0.13 | 4 | CPA2 | YJR109C | 1.06 |
| P04076 | ARGININOSUCCINATE LYASE (EC 4.3.2.1) | 1.65 | | 1 | ARG4 | YHR018C | 1.13 |

| SWISS-Prot Accession | Peptide Sequence | H/L Ratio[b] | Stdv[c] | N[d] identified | N[d] with H/L | Max (Ion Score)[b] | p < 0.05 |
|---|---|---|---|---|---|---|---|
| P07258 | ANVALIDCGVKENIIR | 4.86 | | 2 | 1 | 64 | * |
|  | ANVALIDCGVKENIIR | 3.52 | | 1 | 1 | 37 | * |
|  | ANVALIDCGVK | 2.52 | | 1 | 1 | 35 | * |

TABLE 2-continued

| | | | | | | | |
|---|---|---|---|---|---|---|---|
| | ANVALIDCGVK | 3.29 | | 3 | 1 | 36 | * |
| | ATFCIQNGPSFEGISFGANK | 2.21 | | 1 | 1 | 3 | |
| | ATFCIQNGPSFEGISFGANK | | | 2 | 0 | 65 | * |
| P22768 | FVCVDCR | 1.76 | | 5 | 0 | 7 | |
| | FVCVDCR | 2.01 | | 3 | 1 | 28 | * |
| | GCYEQAPLTVLR | | | 2 | 0 | 45 | * |
| | GCYEQAPLTVLR | 1.62 | | 2 | 1 | 11 | |
| | QEGCFAVSHGCTGK | 1.81 | | 1 | 1 | 14 | |
| P03965 | HLGVIGECNVQYALQPDGLDYR | 2.38 | 0.1 | 2 | 2 | 21 | * |
| | LYDNGCNIMGTNPNDIDRAENR | 2.27 | | 1 | 1 | 28 | * |
| | LYDNGCNIMGTNPNDIDR | 2.12 | 0.3 | 11 | 5 | 72 | * |
| | IGSSVEFDWCAVNTAK | 1.53 | | 1 | 0 | 7 | |
| | VIECNIR | 1.76 | 0.1 | 3 | 3 | 10 | |
| | DINIPIAESFACETVDEALEAAER | | | 1 | 0 | 33 | * |
| | CMNIVNIYK | 1.48 | | 4 | 1 | 50 | * |
| P04076 | ETHHISGECVATAER | 1.65 | 0.2 | 2 | 2 | 61 | * |
| | ETHHISGECVATAER | | | 1 | 0 | 11 | |

| SWISS-Prot Accession | Protein Name | Stdv | N | Biological Process (GO) |
|---|---|---|---|---|
| P07258 | CARBAMOYL-PHOSPHATE SYNTHASE, ARGININE-SPECIFIC, SMALL CHAIN (EC 6.3.5.5) | 0.18 | 4 | arginine biosynthesis |
| P22768 | ARGININOSUCCINATE SYNTHASE (EC 6.3.4.5) | 0.16 | 4 | arginine biosynthesis |
| P03965 | CARBAMOYL-PHOSPHATE SYNTHASE, ARGININE-SPECIFIC | 0.16 | 4 | arginine biosynthesis |
| P04076 | ARGININOSUCCINATE LYASE (EC 4.3.2.1) | 0.17 | 4 | arginine biosynthesis |

| SWISS-Prot Accession | Peptide Sequence | Min(Error) [ppm] | missed cleavage | Platform |
|---|---|---|---|---|
| P07258 | ANVALIDCGVENIIR | 0 | 1 | MALDI |
| | ANVALIDCGVENIIR | 15 | 1 | ESI |
| | ANVALIDCGVK | 0 | 0 | MALDI |
| | ANVALIDCGVK | 15 | 0 | ESI |
| | ATFCIQNGPSFEGISFGANK | 4 | 0 | MALDI |
| | ATFCIQNGPSFEGISFGANK | 47 | 0 | ESI |
| P22768 | FVCVDCR | 0 | 0 | MALDI |
| | FVCVDCR | 23 | 0 | ESI |
| | GCYEQAPLTVLR | 6 | 0 | ESI |
| | GCYEQAPLTVLR | 30 | 0 | MALDI |
| | QEGCFAVSHGCTGK | 85 | 0 | MALDI |
| P03965 | HKGVIGECNVQYALQPDGLDYR | 4 | 0 | MALDI |
| | LYDNGCNIMGTNPNDIDRAENR | 15 | 1 | MALDI |
| | LYDNGCNIMGTNPNDIDR | 0 | 0 | MALDI |
| | IGSSVEFDWCAVNTAK | 10 | 0 | MALDI |
| | VIECNIR | 9 | 0 | MALDI |
| | DINIPIAESFACETVDEALEAAER | 14 | 0 | ESI |
| | CMNIVNIYK | 8 | 0 | ESI |
| P04076 | ETHHISGECVATAER | 5 | 0 | MALDI |
| | ETHHISGECVATAER | 91 | 0 | ESI |

Where the superscripts in Table 2 indicate as follows:
[a]H/L protein ratios and standard deviation were calculated according to formula (1) in Peptides were only considered that had at least once been significantly identified by Mascot ($p < 0.05$, i.e. threshold of ion score >20, Swiss-Prot Database (v02.13.2003)). Maximum ion score and an ion score - weighted mean of ratios were taken to consolidate ion scores and H/L ratios of peptides identified by MALDI and ESI;
[b]MALDI H/L peptide ratios were calculated applying formula (2) Table 1 with weighting $v_j = 1$, ESI H/L peptide ratios were determined by Pro ICAT software;
[c]Standard deviation based on multiple peptide-quantitation values identified by MALDI or ESI; and
[d]In some instances, peptides were identified, but the ratios were not determined because of low intensity.

Example 5

Search Result Based Analysis, Dependent Workflow and Recalibration

Figure 22:
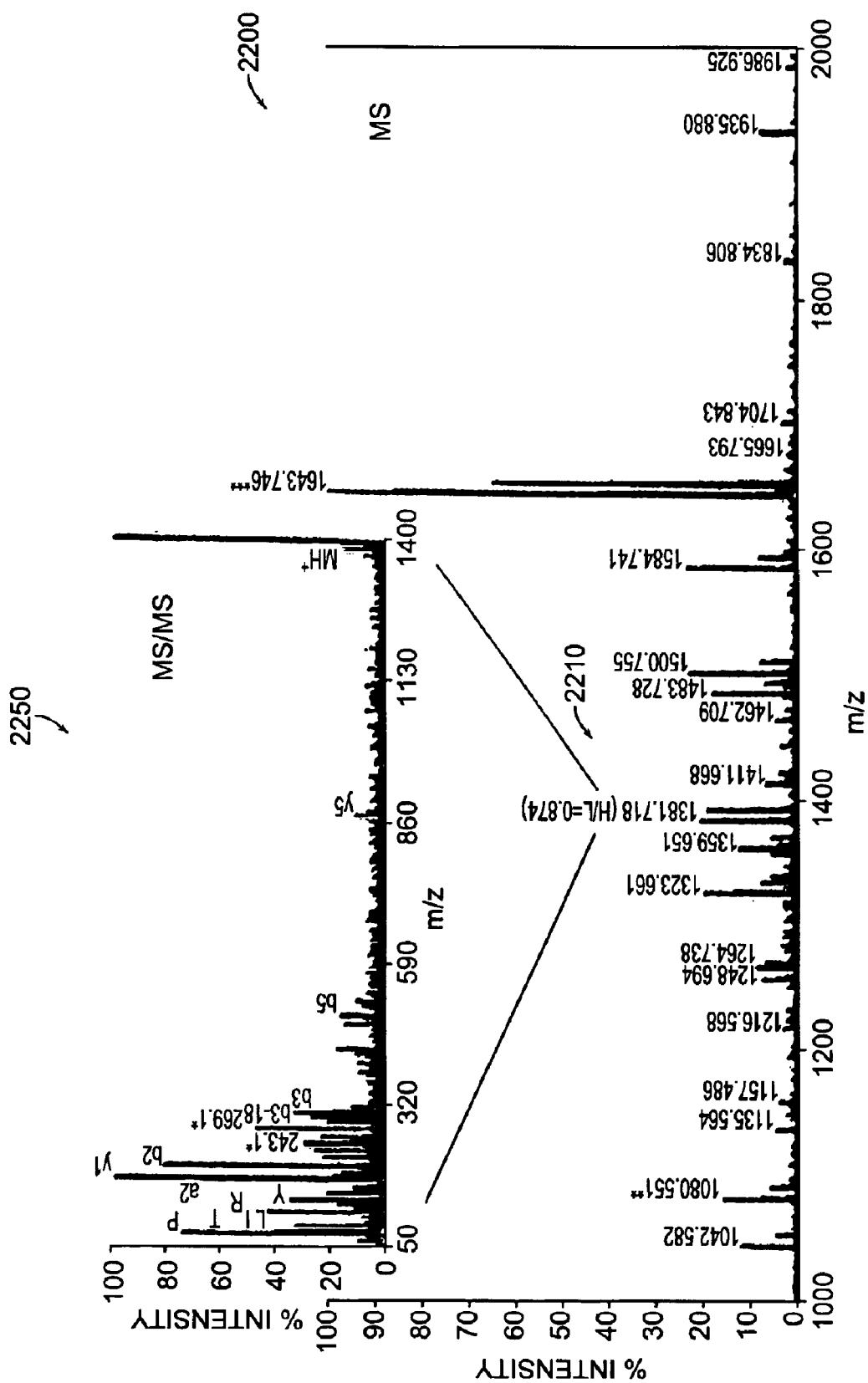
FIG. 22 illustrates a search result dependent calibration, quantitation and identification of probable transcription factor PML (P29590) with peptide sequence TPTLTSIYCR.
Figure 23:
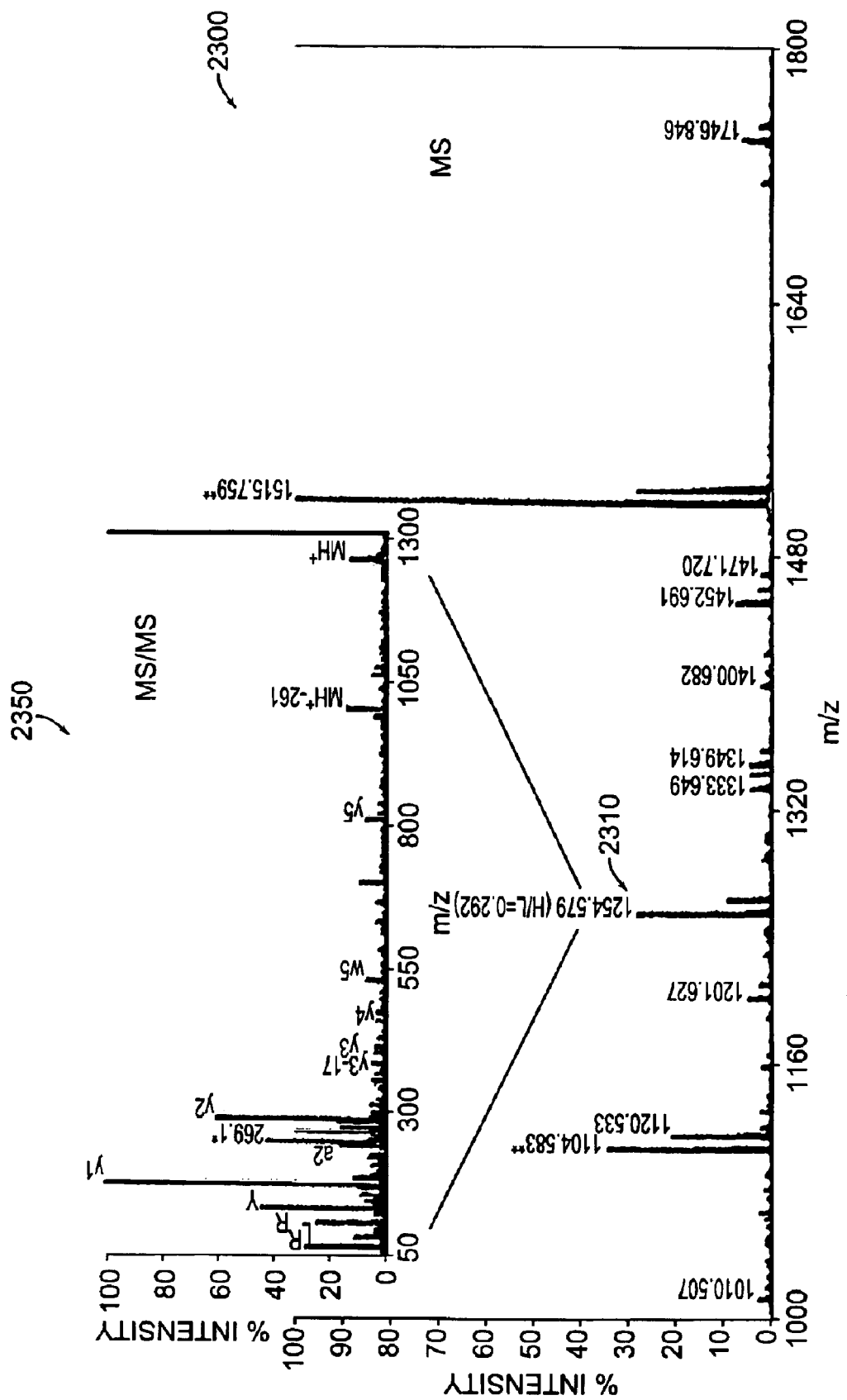
FIG. 23 illustrates a search result dependent calibration, quantitation and identification of transducin beta-like 2 protein (Q9Y4P3) with peptide sequence YLATCADDR.

In various embodiments, the theoretical masses of biomolecules (e.g., peptides) that are identified with high confidence in the first rounds of MS/MS or MS$^n$ acquisition and analysis can be used to recalibrate the MS data. In various embodiments, the number of reference masses for recalibration across MALDI plate wells can be increased, for each theoretical mass, by identifying peak masses within a specified tolerance window in successively deposited MALDI spots along the $\mu$LC peptide elution profile. The fragment spectrum search can be repeated by setting tighter search tolerances for recalibrated precursors and by retaining the original search tolerance for the non-recalibrated ones, to facilitate obtaining additional or higher confidence hits, but also fewer false positive identifications. FIGS. 22 and 23 are examples, where the number of significant protein hits ($p<0.05$) could be increased by 50%, are used to illustrate the idea and principles of such an approach.

FIG. 22 illustrates a search result dependent calibration, quantitation and identification of probable transcription factor PML (P29590) with peptide sequence TPTLTSIYCR.

The MS spectrum 2200 represents a 20 sec fraction collected from a C18 RP-LC gradient run of one strong cation exchange fraction and shows multiple HL pairs. The m/z values are displayed for the light variants only. The mass difference between the components of an HL pair containing a single-cysteine is about 9.03 Da. The median ratio of the components from the experimental sample (labeled with the heavy reagent) to the control sample (labeled with the light reagent) is around 0.5 with a standard deviation of 0.14 (as determined from all ~1000 pairs in the SCX fraction). After normalization to the median, the pair at 1381/1390, 2210, stands out as differentially regulated. The MS/MS spectrum 2250 of precursor 1381.7 is shown in the inset. The Mascot score of 23 associated with this spectrum 2250 is below significance (threshold of 25 determined by Mascot, $p<0.05$), although some features in the MS/MS spectrum— namely the unusually abundant threonine immonium ion, suggesting the presence of multiple threonine residues, strong y1, a2 and b2 fragments—give added credibility to this identification. Fragments with * are derived from the ICAT reagent labeled cysteine residue itself. Database searching with Mascot was initially performed using 200 ppm tolerance on the mass of the precursor. Masses corresponding to high-confidence identifications (four theoretically known masses if both heavy and light labeled components are considered) marked by  in the MS spectrum 2200** were then utilized for recalibration, enabling a second search with a decreased mass tolerance of precursor masses of 10 ppm tolerance. The mass labels in the Fig. correspond to the values after internal calibration. The theoretical mass of the light-ICAT labeled TPTLTSIYCR sequence is 1381.715 Da (as MH+): the experimentally determined one is 1381.718 (2 ppm error). The Swiss-Prot Database (v02.13.2003) contains 20 tryptic peptides from human proteins within a +/−5 ppm mass window around 1381.718 Da, of which only 4 unique sequences contain a single cysteine residue. The high mass accuracy constraint of the precursor mass reduced the search space of the peptides within +/−5 ppm tolerance window and lowered the threshold of the Mascot ion score to 13 resulting in a significant hit ($p<0.01$.)

FIG. 23 illustrates a search result dependent calibration, quantitation and identification of transducin beta-like 2 protein (Q9Y4P3) with peptide sequence YLATCADDR. The MS spectrum 2300 represents another 20 sec fraction collected from a C18RP-LC gradient run of one strong cation exchange fraction. M/Z values in the MS spectrum 2300 are only displayed for the light labeled peptides. In the experiment, the median ICAT ratio is around 0.5 (defined as heavy/light). The protein "transducin betalike 2" is identified by the peptide at m/z 1254.579, 2310, and has a heavy/light ratio of 0.292, which is significantly below the mean, representing therefore, a down-regulation of this protein. The inset shows the MS/MS spectrum 2350. The Mascot score of 22 is below the significance threshold (ion scores >24 indicate identity at $p<0.05$), if 200 ppm tolerance on the precursor mass is used. The components in the same MS spectrum identified with high confidence (as indicated by **) help to improve the significance of other identifications by virtue of accurate mass measurement. Using four masses (two pairs) as internal references, the experimental and theoretical masses for the component of m/z 1254.6 are consistent with the sequence assignment above within 1 ppm. The mass labels in the MS trace reflect the values following the internal calibration. The only tryptic peptide from human proteins in Swiss-Prot Database (v02.13.2003) within +/−5 ppm tolerance that is compatible with the MS/MS spectrum is YLATCADDR—even without restricting the considerations to cysteine containing peptides and allowing for one missed tryptic cleavage. The high mass accuracy constraint of the precursor mass reduced the search space of the peptides within +/−5 ppm tolerance window and lowered the threshold of the Mascot ion score to 13 resulting in a significant hit ($p<0.01$.)

Example 6

Graphical Overview

Figure 24:
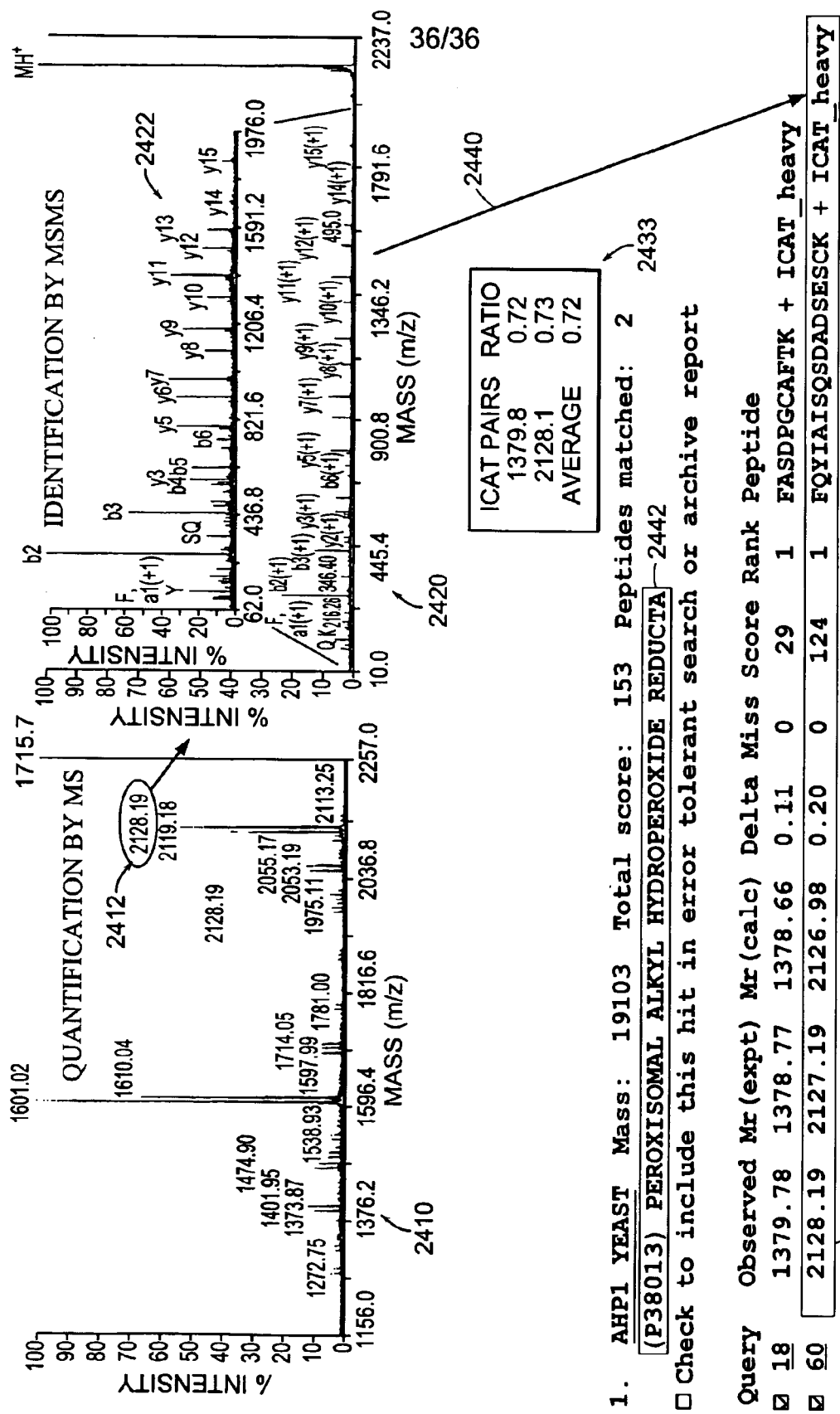
FIG. 24 is a schematic illustration of an example of quantification and identification.

Referring to FIG. 24, an overview of various embodiments and illustrative examples of mass spectra, fragmentation spectra and analysis are shown. As illustrated in this example, the m/z range associated with a peak 2412 of a mass spectra is selected for further analysis. A fragmentation spectrum of this selected peak is obtained 2420 of which a portion has been enlarged with various peaks identified therein 2422. In this example, ICAT ratios are also determined 2433 and the ICAT light and heavy modifications of the Cys 2440 are then utilized to identify the peptide 2444 associated with the mass spectra 2422. A plurality (two or more) of peptide identifications are then used to determine an associated protein 2442.

In another aspect, the functionality of one or more of the methods described above may be implemented as computer-readable instructions on a general purpose computer. The computer may be separate from, detachable from, or integrated into a mass spectrometry system. The computer-readable instructions may be written in any one of a number of high-level languages, such as, for example, FORTRAN, PASCAL, C, C++, or BASIC. Further, the computer-readable instructions may be written in a script, macro, or functionality embedded in commercially available software, such as EXCEL or VISUAL BASIC. Additionally, the computer-readable instructions could be implemented in an assembly language directed to a microprocessor resident on a computer. For example, the computer-readable instructions could be implemented in Intel 80×86 assembly language if it were configured to run on an IBM PC or PC clone. In one embodiment, the computer-readable instructions can be embedded on an article of manufacture including, but not limited to, a computer-readable program medium such as, for example, a floppy disk, a hard disk, an optical disk, a magnetic tape, a PROM, an EPROM, or CD-ROM.

The claims should not be read as limited to the described order or elements unless stated to that effect. While the invention has been particularly shown and described with reference to specific illustrative embodiments, it should be understood that various changes in form and detail may be made without departing from the spirit and scope of the invention as defined by the appended claims. By way of example, any of the disclosed features may be combined with any of the other disclosed features to analyze a sample containing biomolecules. Therefore, all embodiments that come within the scope and spirit of the following claims and equivalents thereto are claimed.

What is claimed is:

1. A method for analyzing a sample containing biomolecules comprising the steps of providing a plurality of sample portions of a sample containing biomolecules;

acquiring one or more mass spectra of at least one of the sample portions;

analyzing the one or more mass spectra using at least one of an expression dependent based analysis, and a search results based analysis;

selecting one or more mass-to-charge ratio ranges based on the analysis of at least one of the expression dependent based analysis and the search results based analysis of the one or more mass spectra;

acquiring a fragmentation spectrum of at least one of the sample portions at one or more of the selected one or more mass-to-charge ratio ranges;

comparing the fragmentation spectrum of at least one of the selected one or more mass-to-charge ratio ranges to a database of known or predicted fragmentation mass spectra; and determining whether a biomolecule is present in the sample based on the comparison.

2. The method of claim 1, wherein the biomolecules comprise at least one of proteins and peptides.

3. The method of claim 1, wherein the step of acquiring one or more mass spectra comprises:

ionizing at least a portion of the biomolecules in a sample portion using matrix assisted laser desorption ionization; and acquiring one or more mass spectra using a mass spectrometer.

4. The method of claim 3, wherein the mass spectrometer comprises a time-of-flight mass spectrometer.

5. The method of claim 1, wherein the step of analyzing the one or more mass spectra comprises determining an expression level ratio between one or more differentially labeled biomolecules in the sample portion.

6. The method of claim 5, wherein the step of selecting one or more mass-to-charge ratio ranges comprises selecting one or more mass-to-charge ratio ranges based on the expression level ratios of a mass signal in the one or more mass spectra.

7. The method of claim 5, further comprising a step of compensating for sample bias in one or more expression level ratios.

8. The method of claim 1, wherein the step of analyzing the one or more mass spectra comprises determining a signal intensity and a signal-to-noise ratio for the one or more mass signals in one or more mass spectra.

9. The method of claim 8, wherein the step of selecting one or more mass-to-charge ratio ranges comprises selecting one or more mass-to-charge ratio ranges based on the signal intensity and a signal-to-noise ratio for one or more mass signals in the one or more mass spectra.

10. The method of claim 1, wherein the step of analyzing the one or more mass spectra comprises comparing of at least a portion of one or more of the one or more mass spectra to one or more known or predicted mass spectra to assign one or more biomolecules as potential identifications of one or mass signals in the one or more mass spectra.

11. The method of claim 10, wherein the step of selecting one or more mass-to-charge ratio ranges comprises selecting one or more mass-to-charge ratio ranges based on a confidence level associated with the one or more biomolecules assigned as potential identifications of one or mass signals in the one or more mass spectra.

12. The method of claim 10, wherein the step of analyzing the one or more mass spectra comprises comparing of at least a portion of one or more of the one or more mass spectra to one or more known or predicted mass spectra to assign one or more biomolecules as potential identifications of one or mass signals in the one or more mass spectra using a peptide mass fingerprinting technique.

13. The method of claim 1, wherein the step of acquiring a fragmentation spectrum comprises:

ionizing at least a portion of the biomolecules in a sample portion using matrix assisted laser desorption ionization to produce sample ions;

separating sample ions using a first mass spectrometer;

fragmenting at least a portion of the sample ions in the selected one or more mass-to-charge ratio ranges; and acquiring a fragmentation spectrum using a second mass spectrometer.

14. The method of claim 13, wherein the first mass spectrometer and second mass spectrometer comprises a tandem time-of-flight mass spectrometer system.

15. An article of manufacture comprising a computer-readable media with computer-readable instructions embodied thereon for performing the method of claim 1.

16. A method for analyzing a sample containing proteins comprising the steps of providing a plurality of sample portions each comprising a first sample containing at least one of peptides and proteins and a second sample containing at least one of peptides and proteins, at least a portion of the biomolecules in the first sample and the second sample being differentially labeled with an isotope coded reagent;

acquiring one or more mass spectra of at least one of the sample portions;

determining an expression level ratio between one or more differentially labeled biomolecules in the sample portion;

selecting one or more mass-to-charge ratio ranges based on the expression level ratios of a mass signal in the one or more mass spectra;

acquiring a fragmentation spectrum of at least one of the sample portions at one or more of the selected one or more mass-to-charge ratio ranges;

comparing the fragmentation spectrum of at least one of the selected one or more mass-to-charge ratio ranges to a database of known or predicted fragmentation mass spectra; and determining whether a biomolecule is present in the sample based on the comparison.

17. The method of claim 16, wherein the step of acquiring one or more mass spectra comprises:

ionizing at least a portion of the biomolecules in a sample portion using matrix assisted laser desorption ionization; and acquiring one or more mass spectra using a mass spectrometer.

18. The method of claim 17, wherein the mass spectrometer comprises a time-of-flight mass spectrometer.

19. The method of claim 16, further comprising a step of compensating for sample bias in one or more expression level ratios.

20. The method of claim 16, further comprising the step of determining a signal intensity and a signal-to-noise ratio for one or more mass signals in the one or more mass spectra.

21. The method of claim 20, wherein the step of selecting one or more mass-to-charge ratio ranges further comprises selecting one or more mass-to-charge ratio ranges based on the signal intensity and a signal-to-noise ratio for one or more mass signals in the mass spectrum.

22. The method of claim 16, further comprising the step of comparing of at least a portion of one or more of the one or more mass spectra to one or more known or predicted mass spectra to assign one or more biomolecules as potential identifications of one or mass signals in the one or more mass spectra.

23. The method of claim 22, wherein the step of selecting one or more mass-to-charge ratio ranges further comprises selecting one or more mass-to-charge ratio ranges based on a confidence level associated with the one or more biomolecules assigned as potential identifications of one or mass signals in the one or more mass spectra.

24. The method of claim 22, wherein the step of analyzing the one or more mass spectra comprises comparing of at least a portion of one or more of the one or more mass spectra to one or more known or predicted mass spectra to assign one or more biomolecules as potential identifications of one or mass signals in the one or more mass spectra using a peptide mass fingerprinting technique.

25. The method of claim 16, wherein the step of acquiring a fragmentation spectrum comprises:

ionizing at least a portion of the biomolecules in a sample portion using matrix assisted laser desorption ionization to produce sample ions;

separating sample ions using a first mass spectrometer;

fragmenting at least a portion of the sample ions in the selected one or more mass-to-charge ratio ranges; and acquiring a fragmentation spectrum using a second mass spectrometer.

26. The method of claim 25, wherein the first mass spectrometer and second mass spectrometer comprises a tandem time-of-flight mass spectrometer system.

27. An article of manufacture comprising a computer-readable media with computer-readable instructions embodied thereon for performing the method of claim 16.

28. A method for analyzing a sample for at least one biomolecule comprising the steps of depositing at least one sample portion on a solid support;

vaporizing at least a portion of the sample portion by matrix assisted laser desorption ionization to form a first vaporized ionized sample;

processing at least a portion of the first vaporized ionized sample with a mass spectrometry apparatus to determine a first data set comprising a list of ion abundances as a function of ion mass-to-charge ratio of the first vaporized ionized sample;

comparing the first data set with at least one of a second data set which identifies biomolecules by ion abundance as a function of ion mass-to-charge ratio;

selecting one or more ion mass-to-charge ratio ranges for further analysis based on the comparison;

vaporizing at least another portion of the biological sample by matrix assisted laser desorption ionization to form a second vaporized ionized sample;

processing at least a portion of the second vaporized ionized sample with a mass spectrometry apparatus adjusted based on the first data set thereby to determine a third data set comprising a list of ion abundance as a function of ion mass-to-charge ratio of the second vaporized ionized sample; and performing at least one of the steps of:

comparing the third data set with a fourth data set which identifies biomolecules by ion abundance as a function of ion mass-to-charge ratio, and using the identified biomolecules data and the first data set to obtain quantitative information on the one or more biomolecules in the sample.

29. The method of any one of claims 28, wherein at least one first vaporized biomolecule having a low concentration in the sample is processed as a second vaporized ionized sample prior to processing a biomolecule having a higher concentration in the sample than the first vaporized biomolecule.

30. An article of manufacture comprising a computer-readable media with computer-readable instructions embodied thereon for performing the method of claim 28.

* * * * *